United States Patent
Hendler et al.

(10) Patent No.: US 9,636,019 B2
(45) Date of Patent: May 2, 2017

(54) DEVICE FOR USE IN ELECTRO-BIOLOGICAL SIGNAL MEASUREMENT IN THE PRESENCE OF A MAGNETIC FIELD

(75) Inventors: Talma Hendler, Tel Aviv (IL); Mordekhay Medvedovsky, Beer-Sheva (IL); Andrey Zhdanov, Helsinki (FI); Ilana Klovatch, Petah Tikva (IL); Firas Fahoum, Tel Aviv (IL)

(73) Assignee: THE MEDICAL RESEARCH, INFRASTRUCTURE, AND HEALTH SERVICES FUND OF THE TEL-AVIV MEDICAL CENTER, Tel Aviv (IL)

(*) Notice: Subject to any disclaimer, the term of this patent is extended or adjusted under 35 U.S.C. 154(b) by 693 days.

(21) Appl. No.: 13/878,297

(22) PCT Filed: Oct. 6, 2011

(86) PCT No.: PCT/IL2011/000785
§ 371 (c)(1),
(2), (4) Date: Apr. 8, 2013

(87) PCT Pub. No.: WO2012/046237
PCT Pub. Date: Apr. 12, 2012

(65) Prior Publication Data
US 2013/0204122 A1      Aug. 8, 2013

Related U.S. Application Data

(60) Provisional application No. 61/390,722, filed on Oct. 7, 2010, provisional application No. 61/445,080, filed on Feb. 22, 2011.

(51) Int. Cl.
*A61B 5/05* (2006.01)
*A61B 5/00* (2006.01)
(Continued)

(52) U.S. Cl.
CPC .......... *A61B 5/0055* (2013.01); *A61B 5/0476* (2013.01); *A61B 5/0478* (2013.01); *A61B 2562/222* (2013.01)

(58) Field of Classification Search
CPC ............ A61B 2562/222; A61B 5/0055; A61B 5/0476; A61B 5/0478
See application file for complete search history.

(56) References Cited

U.S. PATENT DOCUMENTS 3,998,213 A * 12/1976 Price .................... A61B 5/0424
600/383
5,479,934 A * 1/1996 Imran .................. A61B 5/0017
600/390

(Continued)

FOREIGN PATENT DOCUMENTS

WO        99/22642 A1     5/1999

OTHER PUBLICATIONS

Srivastava et al. "ICA-based procedures for removing ballistocardiogram artifacts from EEG data acquired in the MRI scanner." NeuroImage 24 (2005), 50-60.*

(Continued)

*Primary Examiner* — Jonathan Cwern
*Assistant Examiner* — Amelie R Gillman
(74) *Attorney, Agent, or Firm* — Browdy and Neimark, PLLC

(57) ABSTRACT

A device is presented for use in an EEG measurement performed in the presence of a magnetic field. The device includes a wiring array for connecting an electrodes arrangement to an electroencephalogram (EEG) monitoring device. The wiring array includes sampling lines arranged to form first and second groups of sampling lines, arranged in a spaced-apart substantially parallel relationship extending along first and second axes respectively, at least some of the (Continued)

sampling lines being wire bundles including a plurality of wires for connecting to a corresponding plurality of electrodes of the EEG electrodes arrangement; the first and second groups of sampling lines intersect with each other to form a net structure when placed on area of measurement. The wiring array thereby enable generation of EEG data characterized by reduced motion artifact and/or reduced gradient artifact associated with the presence of the magnetic field during the EEG measurement.

30 Claims, 29 Drawing Sheets

(51) Int. Cl.
 *A61B 5/0476* (2006.01)
 *A61B 5/0478* (2006.01)

(56) References Cited

U.S. PATENT DOCUMENTS

| | | | | |
|---|---|---|---|---|
| 5,687,724 | A * | 11/1997 | Jewett | G06K 9/0057 324/244 |
| 6,510,340 | B1 * | 1/2003 | Jordan | A61B 5/0478 600/383 |
| 6,708,051 | B1 | 3/2004 | Durousseau | |
| 2008/0004537 | A1 * | 1/2008 | Uutela | A61B 5/0428 600/509 |
| 2008/0306397 | A1 | 12/2008 | Bonmassar et al. | |
| 2009/0099473 | A1 | 4/2009 | Dunseath et al. | |
| 2010/0022907 | A1 * | 1/2010 | Perez-Velazquez | A61B 5/4076 600/544 |
| 2010/0036275 | A1 * | 2/2010 | Alkire | A61B 5/6814 600/544 |
| 2010/0286549 | A1 * | 11/2010 | John | A61B 5/0476 600/544 |

OTHER PUBLICATIONS

P. J. Allen et al., "Identification of EEG events in the MRI scanner: the problem of pulse artifact and method for its subtraction", NeuroImage 8 (3), 229-239 (1998)—Abstract.

R. I. Goldman et al., "Acquiring simultaneous EEG and functional MRI", J Clin Neurophysiol. 111, 1974-1980 (2002)—Abstract.

R.K. Niazy et al., NeuroImage 28, 720-737 (2005)—Abstract.

G. Bonmassar et al., "Motion and balistocardiogram artifact removal for interleaved recording of EEG and EPs during MRI", NeuroImage 16(4), 1127-1141 (2002)—Abstract.

C. Benar et al., "Quality of EEG in simultaneous EEG-fMRI for epilepsy", Clin. Neurophysiol. 114(3), 569-580 (2003)—Abstract.

G. Srivastabva et al., "ICA-based procedures for removing ballistocardiogram artifacts from EEG data acquired in the MRI scanner", NeuroImage 24(1), 50-60 (2005)—Abstract.

Masterton et al., "Measurement and reduction of motion and ballistocardiogram artifacts from simultaneous EEG and fMRI recordings", NeuroImage 37(1), 202-211 (2007)—Abstract.

International Search Report of PCT/IL2011/000785 mailed Mar. 5, 2013.

* cited by examiner

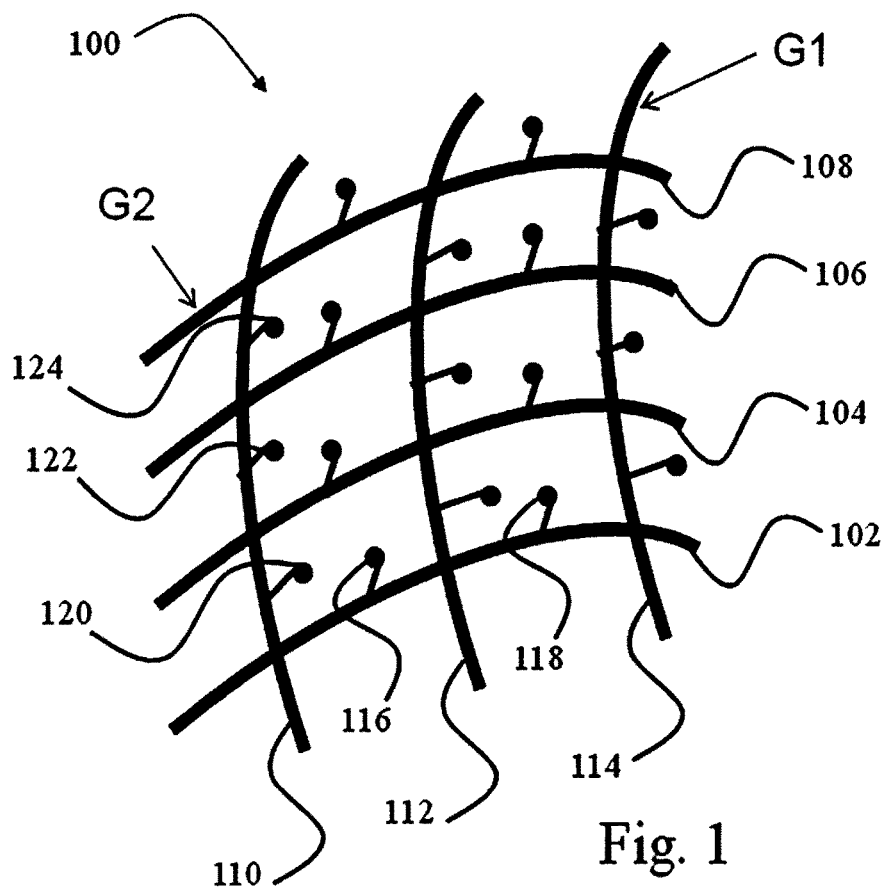
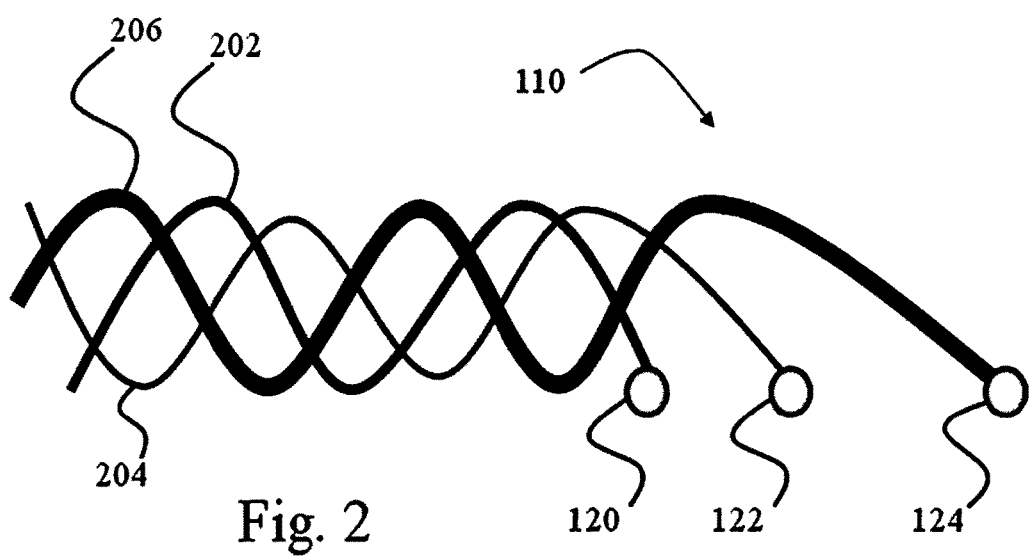

DEVICE FOR USE IN ELECTRO-BIOLOGICAL SIGNAL MEASUREMENT IN THE PRESENCE OF A MAGNETIC FIELD

FIELD OF THE INVENTION

The present invention is in the field of medical devices, and relates to a device for use in combined measurements/monitoring of electro-biological signal in presence of a magnetic field. Particularly, some embodiments of the present invention relate to, but are not restricted to, electroencephalogram (EEG) during magnetic resonance imaging (MRI), particularly functional MRI (fMRI), or during Transcranial Magnetic Stimulation (TMS).

BACKGROUND OF THE INVENTION

In the medical field, activity of human and animal brains has been scanned in various ways. Two of the more common ways of scanning brain activity are EEG and fMRI.

EEG technique involves measurements of electrical signals generated by the brain's neurons, via a multitude of electrodes placed on a patient's scalp. The neural signals are transmitted by wires to an EEG monitoring system that records the neural signals, and generates data about the signal variation in time, which data can be further analyzed and possibly also displayed. EEG enables high temporal resolution, in the order of milliseconds, and is therefore useful for detecting quick changes in the electrical activity of the brain. EEG, however, has undesirably low spatial resolution.

MRI is a noninvasive medical imaging technique used in radiology to visualize detailed internal structure and limited function of the body. In MRI, a magnetic field is used to align the nuclear magnetization of predetermined materials in fluids of a body. Radio frequency (RF) fields are used to systematically alter the alignment of this magnetization. This causes the materials to produce a rotating magnetic field detectable by a scanner. This signal can be manipulated/affected by additional magnetic fields to build up enough information to construct an image of the body. Different types of MRI generally used for brain scan are, for example, fMRI and magnetic resonance spectroscopy (MRS).

fMRI technique has been used since the 1990s to study the hemodynamic response (change in blood flow) related to neural activity in the brain. In fMRI, levels of deoxyhemoglobin in the brain are detected. Deoxyhemoglobin levels change in areas of the brain in response to changes in neural activity of the specific areas. Because deoxyhemoglobin is paramagnetic, when a patient's brain is subjected to a high magnetic field, deoxyhemoglobin aligns with the magnetic field. Radio frequency fields are then applied to the patient's brain, to rotate the aligned deoxyhemoglobin. As the paramagnetic deoxyhemoglobin rotates back and forth under the influence of the RF fields, a rotating magnetic field is produced, detected by an appropriate detector, and converted into an image of the brain. fMRI is characterized by high spatial resolution of measurements, as different levels of deoxyhemoglobin in specific regions of the brain indicate different levels of neural activity in those specific regions. fMRI is, however, characterized by relatively low temporal resolution, as blood flow response to neural activity peaks approximately 5 seconds after the firing of the neurons.

MRS technique utilizes the principles of MRI and focuses on receiving rotating magnetic fields produced by nuclei such as hydrogen, phosphorus, carbon, sodium, and fluorine, in order to detect biochemical materials of interest, such as, for example, choline containing compounds, creatine, inositol, glucose, N-acetyl aspartate, alanine, and lactate. Elevated concentrations of some of these biochemical materials may indicate the presence of a number of brain diseases, for example cancer, epilepsy, Alzheimer's Disease, Parkinson's disease, and Huntington's Chorea.

To combine the high temporal resolution of EEG and the high spatial resolution of fMRI, medical personnel have been increasingly performing simultaneous EEG and fMRI scans. Similarly, other kinds of MRI scans, such as MRS, may be performed in simultaneously with EEG measurements. This may be done, for example, for the purpose of saving time. The combination of EEG and fMRI scans, otherwise known as EEG/fMRI, however has brought about new problems associated with the fact that EEG measurements are affected by noise artifacts, when performed in the presence of a magnetic field. Therefore, noise artifacts have appeared in EEG measurements performed in conjunction with fMRI scans. Similarly, when using MRS measurements simultaneously with EEG measurements, EEG scans are also affected by noise artifacts caused by the presence of a magnetic field.

Noise can also be introduced into the EEG signals during EEG recording within an MRI scanner. Specifically, noise may be introduced by motion within the MRI environment during the recording of the EEG signals. This type of noise is called a motion artifact. Motion artifacts may be, for example, associated with a ballistocardiogram motion, and/or a movement of the patient during the EEG recording, and/or a movement of EEG equipment during the recording. The amplitude of the noise may be approximately of the same magnitude as the EEG signal.

Some motion artifacts are present as a direct result of an electromagnetic induction in the magnetic field. In EEG scans, as motion causes EEG wires to move within the MRI scanner's magnetic field, the size of the loops created by two wires connected to the electrodes varies, affecting the magnetic flux through the loops, and therefore introducing an induced current through the loops.

Another technique used in conjunction with EEG is Transcranial Magnetic Stimulation (TMS). In TMS, a changing magnetic field is used to induce weak electric currents in the brain; this can cause activity in specific or general parts of the brain, allowing the functioning and interconnections of the brain to be studied. Such activity is generally detected via an EEG apparatus. A variant of TMS, repetitive transcranial magnetic stimulation (rTMS), has been tested as a treatment tool for various neurological conditions such as migraines, strokes, Parkinson's disease, dystonia, tinnitus, depression and auditory hallucinations.

EEG recordings performed during TMS may be affected by a motion artifact, as explained above. Further noise affecting EEG measurements in a TMS environment includes a gradient artifact produced by interference in the electrical loops due to the changes in the magnetic field. This gradient artifact present in EEG measurements during TMS is also known as a magnetic pulse artifact. More specifically, the alternating magnetic field affects magnetic flux through the loops and induces currents, thus creating a gradient artifact in the EEG measurements.

Techniques have been devised to decrease the motion artifact and/or the gradient artifact. According to one system used in the art, wires are tightly held together in bundles essentially parallel to each other. The wires may be twisted together to form the bundles. In this manner, a size of loops formed by wires belonging to the same bundle is decreased, thereby decreasing the motion artifact in EEG readings. Reduction of the loop size also reduces current induced by an alternating magnetic field. This approach enables bipolar EEG measurements with a decreased presence of motion artifacts and/or gradient artifacts.

Another known technique of the kind specified is described for example in US Patent Publication No. 2008/0306397 by Bonmassar et al. which discloses methods, systems and arrangements for obtaining EEG signals from a patient e.g., during a concurrent EEG/fMRI examination of the patient. The methods, systems and arrangements include a cap made of conductive inks with sensor positions for attaching a plurality of sensors to the patient's head. The sensors can include electrodes as well as motion sensors for improving EEG signal quality and MRI image quality in the presence of motion noise and other artifacts within the MRI environment. The electrodes may be composed of conductive inks, and can be used in high magnetic fields due to a weak interaction with the RF fields generated by the fMRI scanner.

Motion artifacts may generally be classified in two categories: Balisto-Cardio-Gram (BCG) and Non-Balisto-Cardio-Gram (NBCG). BCG artifacts are related to scalp pulsation and head movements caused by heart beats. NBCG artifacts are generated by movements which are unrelated to heart beats. Several techniques have been proposed for suppression of BCG artifacts. One such technique is based on subtraction of averaged BCG artifact from the EEG data after calculation of averaged template from subsequent BCG artifacts (Allen P. J, Polizzi G, Krakow K et al, 1998, Identification of EEG events in the MRI scanner: the problem of pulse artifact and method for its subtraction. Neuroimage 8 (3), 229-239). Another similar technique is based on weighted average (Goldman R I, Stern J M, Engel Jr. J, Cohen M S, 2002. Acquiring simultaneous EEG and functional MRI. J Clin Neurophysiol. 111, 1974-1980). A further technique, known as optimal basis function set method (Niazy R K, Beckmann G D, Iannetti J M et al, 2005, NeuroImage 28, 720-737), employs principle component analysis (PCA) to decompose the EEG data into several functions which are fitted to every heart beat artifact. Yet a further technique uses a piezoelectric sensor on skin above temporal artery (Bonmassar G, Purdion P L, Jaaskelainen I P et al, 2002. Motion and balistocardiogram artifact removal for interleaved recording of EEG and EPs during MRI. Neuroimage 16(4), 1127-1141), in order to capture the temporal characteristics of the arterial blood pulse.

GENERAL DESCRIPTION

There is a need in the art for a novel EEG measurement technique performed in the presence of a magnetic field. More specifically, there is a need for an EEG/MRI (particularly, EEG/fMRI) based measurement technique providing higher precision of EEG readings while in the MRI environment. Furthermore, there is a need for an EEG based measurement technique providing higher precision of EEG readings while in a TMS environment.

As indicated above, according to the conventional techniques EEG wires are held together or twisted together in bundles to decrease a size of electric current loops formed in wires belonging to the same bundle, thereby decreasing the motion artifact in EEG readings. This approach enables to decrease the motion artifacts and/or gradient artifacts only as long as the measurements are taken between two wires belonging to the same bundle.

As also described above, various techniques have been proposed to solve a problem associated with motion interference during measurements. However, some of these techniques are specific for BCG-type interference only, and are inefficient for NBCG interference, since they demand accurate recognition of heartbeat timing, and moreover sometimes these techniques suffers from that residual BCG artifact still remains.

Employing the of principle component analysis (PCA) or independent component analysis (ICA) (Benar C, Aghakhani Y, Wang Y et al, 2003, Quality of EEG in simultaneous EEG-fMRI for epilepsy. Clin. Neurophysiol. 114(3), 569-580; and Srivastabva G, Grottaz-Herbette S, Lau K M et al, 2005, ICA-based procedures for removing ballistocardiogram artifacts from EEG data acquired in the MRI scanner. NeuroImage 24(1), 50-60) to suppress motion artifact, might not always be an efficient technique for the components separation, and even after components separation with this technique it is often difficult to classify the components into brain signal and interference.

The employment of independent motion sensors while might be helpful for BCG and NBCG interference recognition (Masterton R A J, Abbott D F, Fleming S W, Jackson G D, 2007, Measurement and reduction of motion and ballistocardiogram artifacts from simultaneous EEG and fMRI recordings, NeuroImage 37(1), 202-211), does not provide a solution for motion associated with non-rigid parts involved in/affecting the measurements, such as non-rigid parts of an EEG electrode arrays and of motion sensors. In addition, scalp movements can be independent of BCG-generated and NBCG-generated head movements, so that the head cannot be considered as an absolute rigid body.

The present invention provides a novel technique for taking EEG measurements in presence of a magnetic field, and for processing/interpreting the EEG measured data.

The present invention provides a novel device for use in EEG measurements/monitoring in presence of a magnetic field (constant or changing), enabling more precise profiling/mapping of the EEG data. The invention enables detection of neural signals from locations extending along intersecting axes, and thus allows for the precise determination of the neural signal vector for each location. This significantly improves the interpretation of measurements and also further contributes to reduction of motion and/or gradient artifacts. This is achieved in the invention by providing an improved wiring array and a net structure formed thereby for connecting a bipolar electrodes' arrangement to an EEG monitoring device during an EEG scan. The wiring array is a net structure formed by the crossing of two groups of sampling lines. In each group at least one of the sampling lines includes at least some bundle of wires tightly held together. The sampling lines of the same group are arranged in a spaced-apart substantially parallel relationship along one axis, and those of the other group are arranged in a spaced-apart substantially parallel relationship along a second intersecting axis. Such wiring array enables the EEG monitor device to read EEG data from electrodes connected to wires belonging to the same bundle. In this manner, EEG measurements may be performed along either direction defined by the bundles belonging to crossing sampling lines, while decreasing an effect of the motion and/or gradient artifact, produced by the magnetic field produced, for example by MRI or TMS, in the EEG measurements.

Also, the present invention provides a novel technique for recognizing and suppressing motion artifacts during EEG measurements, by using a wiring array connecting an EEG electrode arrangement to an EEG monitor. The wiring array includes different sampling lines. At least one of the sampling lines includes a bundle of wires tightly held together extending along a first axis. Optionally, each of the remaining sampling lines is constituted by a single wire, and extends parallel to a second axis. The sampling lines (bundles and, if present, single wires) may be parallel, non parallel, or crossing to form a net array. The invention provides an optimal selection of the EEG electrode combinations for measurements. More specifically, a first set of bipolar EEG measurements is made between electrodes connected to wires of the same bundle; a second set of bipolar EEG measurements is made between electrodes connected to wires belonging to different sampling lines (which are preferably, but not necessarily intersecting sampling lines). Each of the neural signals measured between electrodes, both along bundles and across bundles sampling lines, is transmitted to a different channel/utility of the EEG monitor, where data indicative of each signal is generated. In this manner, both sets of measurements may be performed simultaneously.

A separation algorithm (ICA, PCA, for example) is applied to the measured data to obtain components of the measured data which are differently distributed between the channels. Since the effect of motion artifacts is larger in data corresponding to measurements between electrodes connected to different sampling lines, a value indicative of the interference signal (such as voltage or current, for example) is larger in the EEG data generated by the second measurements set, because such value is increased by the artifact. The components of the data generated by the second measurement set which sport a value which is consistently higher than the value of the corresponding components of the data generated by the first measurement set, correspond to the artifact-affected channels. The removal of such artifact-affected components from all channels will remove interference in data generated by both the first and second measurement sets. Thus, by using simultaneous measurements along and across bundles, motion artifacts can be estimated and suppressed.

While this technique has been described with reference to motion artifacts, it also provides for suppressing other artifacts as well, such as gradient artifacts. This is because also gradient artifacts affect the second set of measurements more than the first set of measurements. Moreover, the above technique is not specific for BCG or NBCG artifacts, nor does it rely on additional elements, such as a motion detector.

Another aspect of the present invention relates to a different technique for recognizing artifacts. This second technique may be used independently of the first technique described above, or in conjunction with it in order to increase its discriminative power. This second technique relies on the fact a source of electric field inside a patient's head produces electric potentials (neural signals) that are distributed between EEG electrodes according to the electrodes' positions on the scalp. Conversely, signals which are induced by movements of head and EEG cables inside the magnetic field (motion artifacts) or induced by a changing magnetic field (gradient artifacts), are dependent on the whole electric circuit (loop) configuration (head and wires) and not only on EEG electrode locations on the scalp. This feature can be used to separate neural signals from artifacts generated by the presence of the magnetic field in the following manner: when the source of the signal is inside the head, and at least three electrodes (A, B, C) are provided in the measurement system, the vector sum of the signal's gradients along the lines AB and BC is a vector along the line AC. Conversely, when the measured signal is an artifact (induced by movement of EEG electrode cables and/or of an EEG amplifier inside magnetic field and/or by a changing magnetic field), the signal's gradient along the line AC is not predictable by vector sum of the signal's gradients along the lines AB and BC, and would most probably be different.

At least some of the measured signals include a neural component generated by a source within the brain and an artifact component. Therefore, a separation algorithm (ICA, PCA, for example) is applied to the measured signals to obtain components of the measured signals. Then gradients of each component along the sides of the triangle or (parameters that are proportional to such gradients, such as weights) are determined. This may be done by selecting three weights for each component, such that each weight corresponds to a bipolar measurement along one of the sides of a triangle formed by the arrangement of the three selected electrodes. If the vector sum of two of the gradients of a signal component along first and second sides of such triangle is sufficiently close to the measured/calculated gradient along the third side, then the respective signal component is classified as a neural component originating from the brain. Otherwise, the component is classified as an artifact and rejected.

Therefore, an aspect of some embodiments of the present invention relate to a measurement device for use in an EEG measurement performed in the presence of a magnetic field, the device comprising a wiring array for connecting an electrodes arrangement to an electroencephalogram (EEG) monitoring device. The wiring array comprises a plurality of sampling lines arranged to form a first group of sampling lines and a second group of sampling lines. The sampling lines of the first group are arranged in a spaced-apart substantially parallel relationship extending along a first axis, at least some of such sampling lines being wire bundles of said first group. The sampling lines of the second group are arranged in a spaced-apart substantially parallel relationship extending along a second axis, intersecting with said first axis, such that said second group of bundles crosses said first group of bundles to form a net structure. Each of the bundles of the first group comprises a plurality of first wires for connecting to a corresponding first plurality of electrodes of said EEG electrodes arrangement. Each of the bundles of the second group comprises a plurality of second wires for connecting to a corresponding second plurality of electrodes of said EEG electrodes arrangement. The wiring array is configured and operable for transmitting a signal measured by the respective electrodes to the EEG monitoring device, enabling generation of EEG data indicative of the neural signal profile along two directions and characterized by reduced motion artifact and/or reduced gradient artifact associated with the presence of the magnetic field during the EEG measurement.

In a variant, the second axis is substantially perpendicular to said first axis.

In another variant, the net structure formed by said first group of sampling lines and said second group of sampling lines is configured for connecting said EEG monitoring device to the EEG electrodes positioned along a patient's scalp according to the International 10-20 system.

In yet another variant, the net structure formed by said first group of sampling lines and said second group of sampling lines is configured for connecting said EEG monitoring device to the EEG electrodes, at least some of said electrodes being joined to the patient's head in one of the following manners: non-invasively pasted the patient's scalp, semi-invasively joined to the patient's head epidural region, and invasively joined to the patient's head subdural region.

In yet a further variant, at least some of the sampling lines are configured for being removably connectable to the respective EEG electrodes, thereby allowing for a replacement of at least some of the EEG electrodes between scans.

Optionally, at least one of said first and second groups of sampling lines is divided into at least two subgroups, the sampling lines of the sub-groups belonging to the same group being arranged in an alternating fashion such that any two adjacent sampling lines belonging to a certain group belong to different subgroups of said certain group.

Another aspect of the present invention relates to a net structure configured for being placed on a patient's scalp in an EEG measurement performed in the presence of a magnetic field, the net structure comprising a wiring arrangement, which comprises first and second groups of sampling lines including wire bundles and extending along first and second intersecting axes respectively, each group being formed by a plurality of spaced-apart substantially parallel sampling lines transmitting EEG signals from a respective plurality of spaced-apart EEG measurement locations, thereby enabling to read EEG data from the measurement locations via the first and second groups of sampling lines, while decreasing at least one of a motion artifact and a gradient artifact generated in the EEG measurement.

According to some embodiments of the present invention, there is provided a measurement device for use in an EEG measurement performed in the presence of a magnetic field, the device comprising: a net structure configured for being placed upon a patient's scalp and comprising a plurality of EEG electrodes; and a wiring array as described above, for connecting said plurality of electrodes to an EEG monitoring device.

A further aspect of some embodiments of the present invention relates to a cap configured for being worn by a patient in an EEG measurement performed in the presence of a magnetic field, the cap carrying a wiring arrangement, which comprises first and second groups of sampling lines including wire bundles and extending along first and second intersecting axes, each group being formed by a plurality of spaced-apart substantially parallel sampling lines, each sampling line being configured for transmitting EEG signals from a respective plurality of spaced-apart EEG measurement locations, thereby enabling to read EEG data from the measurement locations via the first and second groups of sampling lines, while decreasing at least one of a motion artifact and a gradient artifact generated in the EEG measurement.

In some embodiments of the present invention, there is provided a cap configured for being worn by a patient during an EEG measurement performed in the presence of a magnetic field, the cap comprising: a plurality of EEG electrodes; and a wiring array as described above, for connecting said plurality of electrodes to an EEG monitoring device.

Optionally, the cap includes an electrically non conductive headpiece, comprising: an inner surface, configured for being fitted to the patient's head; an outer surface carrying said wiring array; and a plurality of apertures, each said aperture being configured for being traversed by a portion of one of said EEG electrodes for connecting to one of said wires.

In a variant, the headpiece is made of a stretchable material, for closely fitting the scalp of the patient.

In another variant, the headpiece comprises fasteners located on said outer surface and configured for fastening said wiring array to said headpiece.

Yet another aspect of the present invention relates to a system for simultaneous EEG and MRI scan, the system comprising: a magnetic field based device comprising at least one of an MRI scanner for imaging the patient's brain, and a TMS coil device for producing a changing magnetic field to cause activity in a brain; an EEG monitoring device; a plurality of EEG electrodes, configured for being placed at predetermined locations on a patient's scalp and for detecting a neural signal; and a wiring array as described above, for relaying said neural signals to the EEG monitoring device for analysis of said neural signal and generation of EEG data, wherein said EEG data has a reduced motion artifact owing to said net structure of the wiring array.

Optionally, the magnetic field is a magnetic field generated by MRI scanner, and the EEG data is affected by the decreased motion artifact.

In a variant, the measurements effected by the electrodes are bipolar measurements between pairs of electrodes connected to the same sampling line.

In another variant, the measurements effected by the electrodes comprise a first signal measured between a reference electrode and a first electrode, and a second signal measured between said reference electrode and a second electrode, the first and second electrode being connected to the same sampling line. The EEG data generated at the EEG monitoring device is a combination of said first and second signals and is indicative of a signal between the first and second electrode.

In a further variant, the magnetic field is a changing magnetic field generated by a Transcranial Magnetic Stimulation (TMS) coil device, and wherein said EEG data is affected by at least said decreased magnetic pulse artifact.

In yet another variant, said EEG monitoring device is associated with a control unit configured and operable for receiving the EEG data and selecting therefrom predetermined data pieces, and analyzing said data pieces for recognizing and suppressing an artifact generated in the EEG measurement.

Another aspect of some embodiments of the present invention, there is provided a method for performing an EEG measurement in the presence of a magnetic field, the method comprising: providing a magnetic field; providing a plurality of EEG electrodes joined to a patient's head; connecting said EEG electrodes to an EEG monitoring device using a wiring array comprising: a first group of sampling lines which comprise at least one, first, wire bundle and which are arranged in a spaced-apart substantially parallel relationship extending along a first axis, said at least one wire bundle of said first group comprising a plurality of first wires of different lengths for connecting to a corresponding first plurality of said electrodes; and a second group of sampling lines which comprise at least one, second, wire bundle and which are arranged in a spaced-apart substantially parallel relationship extending along a second axis, intersecting with said first axis, such that said second group of sampling lines crosses said first group of sampling lines to form a net structure, said at least one wire bundle of said second group comprising a plurality of second wires of different lengths for connecting to a corresponding second plurality of said electrodes; measuring a neural signal via said electrodes; transmitting said measurement to said monitoring device via said wiring array; and, in the monitoring device, receiving said measurement and yielding EEG data indicative of said neural signal measurement between at least one pair of electrodes connected to the same bundle of said wiring array, said EEG data having at least one of a decreased one of a motion artifact and a decreased gradient artifact.

Optionally, the above method further includes processing said EEG data to calculate an amplitude and an orientation of said neural signal.

In a variant, said detecting of said neural signal comprises detecting said neural signal between any two of said electrodes that are connected to wires belonging to one of said sampling lines.

In another variant, said measuring of said neural signal comprises measuring said neural signal between a reference electrode of said electrodes and at least some of said electrodes. The yielding of EEG data comprises combining measurements taken between said reference electrode and at least two of said electrodes connected to the same of said sampling lines, such that combined EEG data is indicative of said neural signal between said two electrodes, thereby providing said EEG data having at least one of a decreased a motion artifact and a decreased gradient artifact.

In yet another variant, the magnetic field is a constant magnetic field generated by a MRI scanner, or is a changing magnetic field generated by a TMS coil device.

In yet a further variant, the method comprises selecting from the EEG data predetermined data pieces, analyzing said data pieces and recognizing and suppressing an artifact generated in the EEG measurement.

Another aspect of some embodiments of the present invention relates to a method for use in performing EEG measurement in the presence of a magnetic field, the method comprising: providing a plurality of EEG electrodes joined to a patient's scalp; connecting said EEG electrodes to an EEG monitoring device using a wiring array comprising a plurality of sampling lines including one or more wire bundles and being arranged in a spaced-apart relationship, each wire bundle comprising a plurality of wires of different lengths for connecting to a corresponding plurality of said electrodes; measuring neural signals via said electrodes and generating EEG data indicative thereof; selecting from the EEG data predetermined data pieces, said selecting of the data pieces comprising selecting a first set of signal measurements between a first group of electrode pairs, such that each electrode of said first set of pairs is connected to the wires belonging to the same wire bundle, and selecting a second set of the signal measurements between a second group of electrode pairs, such that each electrode of said second group of pairs is connected to the wire belonging to different sampling lines; and analyzing said selected data pieces and recognizing and suppressing an artifact generated in the EEG measurement.

Optionally, said analyzing of the selected data pieces comprises: applying to said first and second sets a separation algorithm to jointly decompose both pieces of data indicative of the signal into a plurality of components; comparing an effect of at least some of said plurality of components on each of the first and second sets of measurements; and recognizing at least one specific component which has the effect on said second set of measurements that is higher than the effect on said first set of measurements, and labeling said specific component as an artifact-affected component.

In a variant, said comparing comprises: determining a first value indicative of the effect of said specific component on said first set of measurements, and a second value indicative of the effect of said specific component on said first set of measurements; calculating a relation between said first and second values; and comparing said relation to a predetermined threshold. Said recognizing comprises recognizing said specific component as an artifact-affected component, according to said comparison between said relation and said predetermined threshold.

According to another aspect of the present invention, there is provided a method for use in performing EEG measurement in the presence of a magnetic field, the method comprising: providing a plurality of EEG electrodes joined to a patient's head; connecting said EEG electrodes to an EEG monitoring device using a wiring array comprising a plurality of sampling lines. each sampling line comprising at least one wire for connecting to one electrode; measuring neural signals via said electrodes and generating EEG data indicative thereof; selecting from the EEG data predetermined data pieces, said selecting of the data pieces comprising selecting at least a set of the signal measurements between a group of electrode pairs, such that each electrode of said second group of pairs is connected to the wire belonging to different sampling lines; and analyzing said selected data pieces and recognizing and suppressing an artifact generated in the EEG measurement.

Optionally, said providing comprises connecting said EEG electrodes to said EEG monitoring device using said wiring array comprising a plurality of sampling lines including one or more wire bundles and being arranged in a spaced-apart relationship, each wire bundle comprising a plurality of wires of different lengths for connecting to a corresponding plurality of said electrodes; and said selecting comprises selecting a first set of signal measurements between a first group of electrode pairs, such that each electrode of said first set of pairs is connected to the wires belonging to the same wire bundle, and selecting a second set of the signal measurements between a second group of electrode pairs, such that each electrode of said second group of pairs is connected to the wire belonging to different sampling lines.

In a variant, said analyzing of the selected data pieces comprises: applying to said selected data set a separation algorithm to decompose said data indicative of the signal into a plurality of components; for each of at least some of said plurality of components, selecting at least three electrodes, such that said at least two of the electrodes are connected to different sampling lines; and for each of at least some of said plurality of components, analyzing gradients of said component along respective sides of a polygon formed by said electrodes.

Optionally, said analyzing comprises: for each of at least some of said plurality of components, determining a set of values, each value being indicative of a magnitude and direction of the gradient of said component along the respective side of the polygon, performing a vector sum of all but one of said values, in order to yield a predicted value corresponding to said value which is not considered in the sum, comparing said predicted value to said value not considered in the sum; and recognizing at least one specific component in which said predicted value is substantially different than said value not considered in the sum, and labeling said specific component as an artifact-affected component.

In a variant, only three electrodes are selected for each component.

The selecting of the electrodes may comprise: for each component, identifying the highest effect of said component on a bipolar measurement; determining a first pair of electrodes corresponding to said bipolar measurement, said first pair of electrodes being constituted by a first electrode and second electrode; and selecting a second and a third electrode pairs, each pair being constituted by electrodes between which bipolar measurements have been performed, said second pair being constituted by said first electrode and a third electrode, and said third pair being constituted by said second electrode and said third electrode.

Optionally, the magnetic field is generated by at least one of a MRI scanner and a TMS coil device.

In a variant, the separation algorithm comprises at least one of principle component analysis (PCA) or independent component analysis (ICA).

In another variant, the sampling lines comprise at least one group of substantially parallel sampling lines including at least two subgroups of the sampling lines, wherein the sub-groups belonging to the same group are arranged in an alternating fashion such that any two adjacent sampling lines belonging to a certain group belong to different subgroups of said certain group.

According to another aspect of the present invention, there is provided a system for use in performing an EEG measurement in the presence of a magnetic field, the system comprising: a plurality of electrodes configured for being disposed along a patient's scalp; an EEG monitor configured for receiving a plurality of signals measured between a plurality of pairs of said electrodes, and generating EEG data indicative of each said signal; a wiring array configured for connecting said plurality of electrodes to said EEG monitor, said wiring array comprising at least two bundles of wires tightly held together, each wire connecting to a corresponding electrode of said plurality of electrodes; and a control unit associated with said EEG monitor and configured and operable for: selecting from the EEG data predetermined data pieces by selecting a first set of signal measurements between a first group of electrode pairs, such that each electrode of said first set of pairs is connected to the wire belonging to the same said bundle, and selecting a second set of the signal measurements between a second group of electrode pairs, such that each electrode of said second group of pairs is connected to the wire belonging to different said bundles; and analyzing said data pieces and recognizing and suppressing an artifact generated in the EEG measurement.

Optionally, the control unit is configured and operable for analyzing the selected data pieces by: applying to said first and second sets a separation algorithm to jointly decompose both pieces of data indicative of the signal into a plurality of components; comparing an effect of at least some of said plurality of components on each of the first and second sets of measurements; and recognizing at least one specific component which has the effect on said second set of measurements that is higher than the effect on said first set of measurements, and labeling said specific component as an artifact-affected component.

Another aspect of some embodiments of the present invention relates to a system for use in performing an EEG measurement in the presence of a magnetic field, the system comprising: a plurality of electrodes configured for being disposed on a patient's head; an EEG monitor configured for receiving a plurality of signals measured between a plurality of pairs of said electrodes, and generating EEG data indicative of each said signal; a wiring array configured for connecting said plurality of electrodes to said EEG monitor, said wiring array comprising a plurality of sampling lines, each sampling line comprising at least one wire connecting said EEG monitor to one or more electrodes; and a control unit associated with said EEG monitor and configured and operable for: selecting from the EEG data predetermined data pieces by selecting at least a set of the signal measurements between a group of electrode pairs, such that each electrode of said group of pairs is connected to a wire belonging to different said sampling lines; and analyzing said data pieces and recognizing and suppressing an artifact generated in the EEG measurement.

Optionally, said wiring array comprises a plurality of sampling lines including one or more wire bundles and being arranged in a spaced-apart relationship, each wire bundle comprising a plurality of wires of different lengths for connecting to a corresponding plurality of said electrodes; and said control unit is configured for selecting a first set of signal measurements between a first group of electrode pairs, such that each electrode of said first set of pairs is connected to the wires belonging to the same wire bundle, and selecting a second set of the signal measurements between a second group of electrode pairs, such that each electrode of said second group of pairs is connected to the wire belonging to different sampling lines.

Optionally, the control unit is configured and operable for analyzing the selected data pieces by: applying to said selected data a separation algorithm to decompose said data indicative of the signal into a plurality of components; for each of at least some of said plurality of components, selecting at least three of electrodes, such that said at least two of the electrodes are connected to different sampling lines; and for each of at least some of said plurality of components, analyzing gradients of said component along respective sides of a polygon formed by said electrodes.

In another variant, the control unit is configured and operable for analyzing said gradients by: for each of at least some of said plurality of components, determining a set of values, each value being indicative of a magnitude and direction of the gradient of said component along the respective side of the polygon, performing a vector sum of all but one of said values, in order to yield a predicted value corresponding to said value which is not considered in the sum, comparing said predicted value to said value not considered in the sum; and recognizing at least one specific component in which said predicted value is substantially different than said value not considered in the sum, and labeling said specific component as an artifact-affected component.

Optionally, only three electrodes are selected for each component.

In a variant, the magnetic field is generated by at least one of a MRI scanner and a TMS coil device.

In another variant, the separation algorithm comprises at least one of principle component analysis (PCA) and independent component analysis (ICA).

The control unit may be integral with said EEG monitor, or may be part of a computing device connected to said EEG monitor.

Another aspect of some embodiments of the present invention relates to a control system for data analysis EEG measurements performed in the presence of a magnetic field, the controls system comprising an EEG monitor for receiving signals from multiple spaced-apart electrodes arranged along at least two sampling lines and generating EEG data, each said sampling line comprising one or more wires connecting to one or more electrodes, and a control unit for: receiving said EEG data; selecting from said EEG data predetermined data pieces corresponding to at least measurements taken by a group of electrode pairs, such that each electrode of said second group of pairs is connected to the wire belonging to different said bundles; and analyzing the selected data pieces for recognizing an artifact thereby enabling suppression thereof.

Optionally, said wiring array comprises a plurality of sampling lines including one or more wire bundles and being arranged in a spaced-apart relationship, each wire bundle comprising a plurality of wires of different lengths for connecting to a corresponding plurality of said electrodes; and said control system is configured for selecting from the EEG data predetermined data pieces by selecting a first set of signal measurements between a first group of electrode pairs, such that each electrode of said first set of pairs is connected to the wire belonging to the same wire bundle, and selecting a second set of the signal measurements between a second group of electrode pairs, such that each electrode of said second group of pairs is connected to the wire belonging to different said sampling lines.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

In order to understand the invention and to see how it may be carried out in practice, embodiments will now be described, by way of non-limiting example only, with reference to the accompanying drawings.

The drawings are provided for purposes of illustration only and merely depict typical or example embodiments of the invention. These drawings are provided to facilitate understanding of the invention and shall not be considered limiting of the breadth, scope, or applicability of the invention. It should be noted that for clarity and ease of illustration these drawings are not necessarily made to scale.

FIG. 1 is a schematic illustration of an example of a portion of a wiring array in a device of the present invention for use in a EEG measurements in the presence of a magnetic field;

FIG. 2 more specifically illustrates an example of a bundle of wires connected to a plurality of EEG electrodes, suitable for use in some embodiments of the present invention;

Reference is now made to FIGS. 14a-14d, which illustrate graphical representations of EEG measurements performed on a test subject as well as the results produced by application of the artifact suppressing techniques of methods of FIGS. 9 and 10 to the measured EEG data.

DETAILED DESCRIPTION OF EMBODIMENTS

Figure 3A:
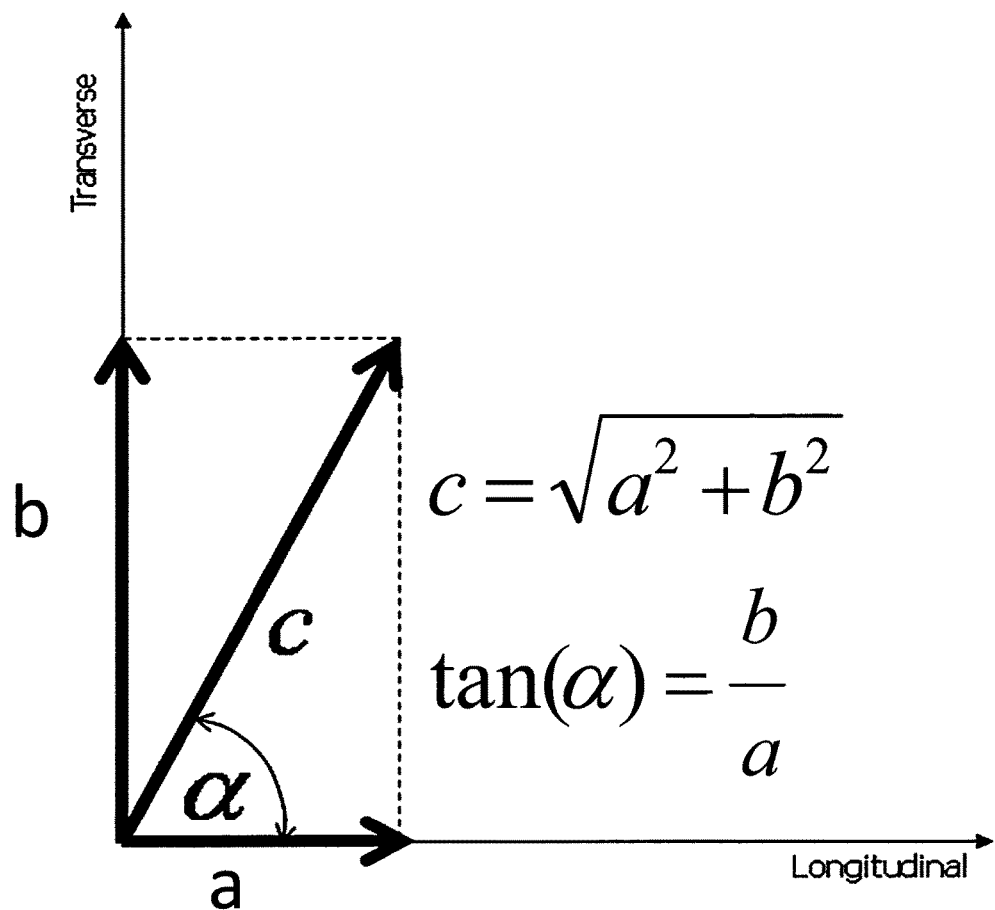
FIGS. 3a and 3b illustrate the general principles used in mapping/profiling (reconstruction of amplitude and orientation) a neural signal generated by EEG measurements performed using the wiring array of the present invention, e.g. that of FIG. 1.

The present invention is in the field of medical devices, and relates to a device for use in combined measurements/monitoring of electro-biological signal in presence of a magnetic field. Particularly, some embodiments of the present invention relate to, but are not restricted to, electroencephalogram (EEG) during magnetic resonance imaging (MRI), particularly functional MRI (fMRI), or during Transcranial Magnetic Stimulation (TMS).

The device of the present invention includes a novel configuration of a wiring array for connecting a bipolar electrodes' arrangement to an EEG monitoring device, for use in a EEG scans performed in the presence of a magnetic field. The wiring array may be used, for example, in simultaneous EEG and MRI (particularly EEG and fMRI) scans, and in EEG scans during TMS. The wiring array includes two groups of wire bundles extending along two intersecting lines (axes), and crossing each other to form a net structure. It should be understood that for the purposes of this patent application the term "line" or "axis" should not be limited to a straight line, but rather should be interpreted broadly to cover a curve extending along a curved surface.

Each group of bundles includes an arrangement of spaced-apart wire bundles. Each wire bundle includes a plurality of wires held tightly together (or twisted together) for connecting to a plurality of EEG electrodes. Because the wires of each bundle are held tightly together (or twisted together), the size of loops of electric current created by two wires of the same bundle, when connected to two electrodes, is decreased. The wiring array of such two groups of wire bundles enables EEG measurements with a decreased effect from motion and/or gradient artifacts to be performed along two directions defined by the two groups of wire bundles.

The first and second groups of wire bundles are preferably substantially perpendicular to each other, i.e. extend along first and second substantially perpendicular axes respectively. Neural electrical activity of any orientation will have a considerable gradient along the direction of at least one of the perpendicular bundles, and is therefore easily and precisely detectable. Even when the direction of the neural signal forms a 45 degree angle with each of the bundles, each bundle picks up a signal attenuated by only a factor of $1/\sqrt{2}$, about equal to 0.71. The wiring array of the present invention can thus advantageously be used with a plurality of electrodes arranged with high density, for example, when 64 or more electrodes are used in an EEG scan. In such a case, the wiring array enables an accurate mapping (reconstruction of amplitude and orientation) of any neural signal by simple trigonometric computations.

Also, the wiring array of the present invention provides for reducing the motion and/or gradient artifact in EEG readings before such readings are processed and/or combined with a signal generated by an external sensor, such as a motion detector. In this manner, accuracy of data obtained by the processing and/or combination of EEG readings with a signal generated by the external sensor is increased. In a variant, the need for the use of the external sensor is obviated altogether. In a similar fashion, owing to the fact that the motion and/or gradient artifact in the EEG readings is reduced by the presence of the two-dimensional wiring array, a need for suppressing the motion and/or gradient artifacts by complicated processing of the EEG signals is diminished, and in some cases even obviated.

The wiring array of the present invention may be placed directly on a patient's scalp, or may be part of (integral with) an EEG cap designed to be worn by the patient.

The following is the description of various examples of the invention. To facilitate understanding, the same reference numbers are used for identifying elements that are common for all the examples of the invention.

Referring now to FIG. 1, there is schematically exemplified a part of the device of the present invention including a portion of a wiring array 100. The wiring array 100 is designed for connecting an electrodes' arrangement to an EEG monitoring device for use in concurrent EEG measurements in the presence of a magnetic field, such as the magnetic field generated in MRI (and fMRI) scans or in TMS.

The wiring array 100 includes a plurality of sampling lines which in the present examples are constituted by wire bundles, and includes two groups G1 and G2 of such wire bundles. Each group includes a plurality of wire bundles arranged in a spaced apart and substantially parallel fashion. As shown in the present example, the first group G1 includes wire bundles 102, 104, 106, and 108, and the second group G2 includes wire bundles 110, 112, and 114. It should be understood, although not specifically shown here, that each wire bundle includes wires that are tightly held together, or optionally twisted together. This is described more specifically below with reference to FIG. 2.

The wire bundles are designed for connecting respective EEG electrodes to an EEG monitoring device. The wire bundle 102 includes wires for connecting electrodes 116 and 118 to the EEG monitoring device (not shown). Similarly, the wire bundle 110 includes wires for connecting electrodes 120, 122, and 124 to the EEG monitoring device.

Bipolar EEG measurements may be taken between any two electrodes connected to wires belonging to the same wire bundle, for example between the electrodes 116 and 118, or between electrodes 120 and 124. As explained above, measurement taken between electrodes connected to wires of the same bundle are characterized by a reduced motion and/or gradient artifact because the wires are tightly held together and the size of the electric current loops between the pairs of electrodes is reduced. Optionally, the bipolar EEG measurements are taken between pairs of adjacent electrodes, such as the electrodes 120 and 122, or the electrodes 122 and 124. Bipolar EEG measurement taken between non adjacent pairs, such the electrodes 120 and 124, may be affected by motion and/or gradient artifacts, because the loop size defined by wires connecting the non adjacent electrode pairs is larger than the loop size defined by wires connecting adjacent electrode pairs. However, the measurement between non adjacent electrode pairs connected to the same bundle may still be characterized by a lower artifact effect compared to measurement without the proposed bundles.

Optionally, the EEG recording is referential, and is used to produce a virtual bipolar signal. For this purpose, a first signal is measured between a reference electrode and a first electrode, and a second signal is measured between the reference electrode and a second electrode. The first and second signals are combined to yield a combination signal indicative of a signal that would have been yielded if the measurement had been performed between the first and second electrodes. This is generally done by subtracting the first signal from the second signal (or vice versa). This process is called virtual bipolar montage. When the first and second electrodes are connected to wires of the same bundle, artifacts of similar amplitudes are present in the first signal and second signal. The subtraction described above, therefore, produces a decreased artifact in a combined signal.

The wire array 100 enables EEG measurements characterized by decreased motion and/or gradient artifacts to be performed along two axes, along which the first and second groups' wire bundles extend. As indicated above, the axis is not necessarily straight and is practically not when the wiring array is configured for placement on a patient's scalp, but the projection of wire bundles' of the same group onto the same plane would result in substantially parallel straight lines extending along the common axis.

Optionally, the first and second axes of the arrangement of respectively the first group of wire bundles and the second group of wire bundles are perpendicular to each other. As described above, with this configuration, neural electrical activity of any orientation will necessarily have a considerable gradient along the direction of at least one of the perpendicular bundles, and is therefore easily detectable. The use of such two-dimensional wiring array is also advantageous when a high density of electrodes is present, which is preferred to increase the spatial resolution of measurements.

In a variant, the wiring array is manufactured according to specific measurements, for connecting the EEG monitoring device to the EEG electrodes positioned along a patient's scalp according to a desired configuration, such as any International System, for example the International 10-20 system. In another variant, at least some of the wires of the array are designed for being removably connectable to the respective electrodes. In this manner electrodes may be replaced between scans. This is advantageous when an electrode turns defective, and also allows the wiring array to be used a plurality of times. Also, this enables the electrodes' set, which when in use is to be in contact with the patient's scalp, to be disposable.

FIG. 2 shows more specifically an exemplary bundle 110 of wires connected to a plurality of EEG electrodes. The wire bundle 110 includes a plurality of wires of different lengths, for connecting the same EEG monitoring device to a plurality of electrodes at different locations on the scalp. The wires 202, 204 and 206 are held tightly together, in order to decrease the size of loops formed between the wires, and are electrically isolated from each other. In a preferred embodiment, the wires are held tightly together by being twisted together. The wires 202, 204 and 206 exit the bundle 110 at different locations along the bundle to connect to electrode 120, 122 and 124 respectively.

Figure 3B:
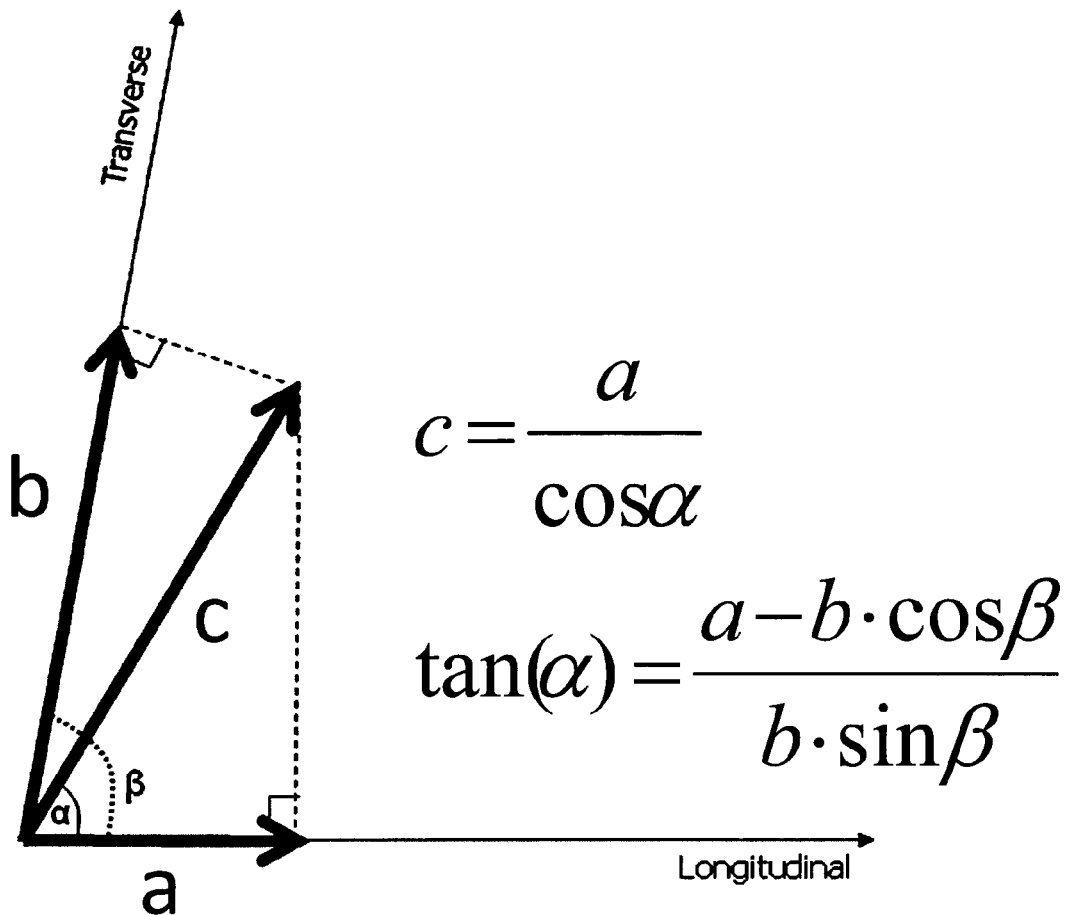

FIGS. 3a and 3b show the principles of mapping/profiling (determination of the amplitude and direction) of a neural signal generated by EEG measurements performed using the wiring array of the present invention (e.g. that of FIG. 1). Here, FIG. 3a, corresponds to a specific example when an angle between crossing wire bundles is 90 degrees (perpendicular first and second axes), and FIG. 3b corresponds to more general situation for any angle β between crossing wire bundles (i.e. intersecting first and second axes).

A neural signal having an amplitude c and an orientation (direction) a with respect to a longitudinal axis is produced in a patient's brain. The neural signal has a first gradient having an amplitude a along the longitudinal axis, for example the axis defined by the wires' group G2, and a second gradient having an amplitude b along a transverse axis, for example the axis defined by the group G1. The amplitude a is detected by a bipolar (real or virtual) measurement between two electrodes connected to one of the bundles of group G2, for example, electrodes 116 and 118. Similarly, the amplitude b is detected by a bipolar (real or virtual) measurement between two electrodes connected to one of the bundles of group G1 and proximal to the electrodes 116 and 118, for example electrodes 120 and 122.

If the first and second axes defined by groups G2 and G1 are perpendicular to each other (FIG. 3a), the amplitude c of the neural signal is calculated via equation 1, and the orientation a of the neural signal is calculated via equation 2.

$$c = \sqrt{a^2 + b^2}$$ Equation 1

$$\tan(\alpha) = \frac{b}{a}$$ Equation 2

If the axes defined by groups G2 and G1 are characterized by any angle β between each other (FIG. 3b), the amplitude c and orientation a of the neural signal are calculated via equations 3 and 4, respectively.

$$c = \frac{a}{\cos \alpha}$$ Equation 3

$$\tan(\alpha) = \frac{a - b \cdot \cos \beta}{b \cdot \sin \beta}$$ Equation 4

Figure 4:
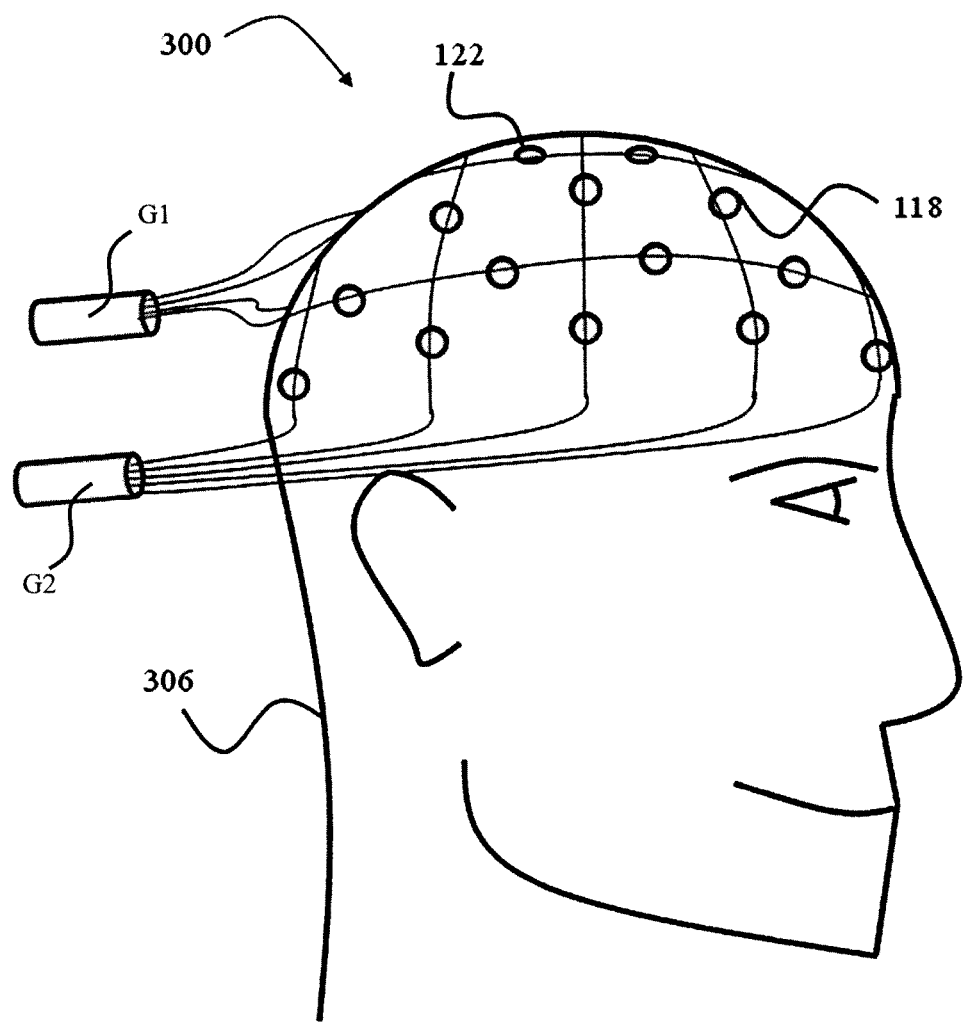
FIG. 4 is a schematic drawing illustrating a net structure formed by crossing wire bundles, according to some embodiments of the present invention.

Reference is made to FIG. 4 showing schematically a net structure 300 formed by the above-described wiring array 100 and designed for being placed on a patient's scalp during an EEG scan performed in the presence of a magnetic field, and for leading EEG signals from electrodes to an EEG monitoring device. The net structure 300 is thus formed by two intersecting groups G1 and G2 of spaced-apart wire bundles. The net structure 300 connects an EEG monitoring device (not shown) to a plurality of EEG electrodes (such as the electrodes 122 and 118, for example) located at predetermined measurement locations on the scalp of a patient 306. Optionally, the net structure 300 is rigid or semi-rigid, in order to on the one hand maintain a desired shape, and on the other hand to enable the net structure 300 to fit the scalp of the patient 306. Alternatively, the net structure 300 is flexible and assumes the desired shape only when the net structure is worn by the patient 306. As indicated above, the net structure 300 may be removably connectable to the electrodes, or alternatively may be integral with the electrodes. The net structure 300 is connectable to various kinds of electrodes, such as non-invasive electrodes pasted on the scalp, to intracranial electrodes (e.g. a subdural electrodes grid), or to semi-invasive (e.g. epidural peg electrodes). Any type of scalp EEG electrodes or intracranial or semi-invasive electrodes may be included to the electrode array, and the wires related to such electrodes can be organized in bundles corresponding to intersecting sampling lines to form the net array 300.

Figure 5:
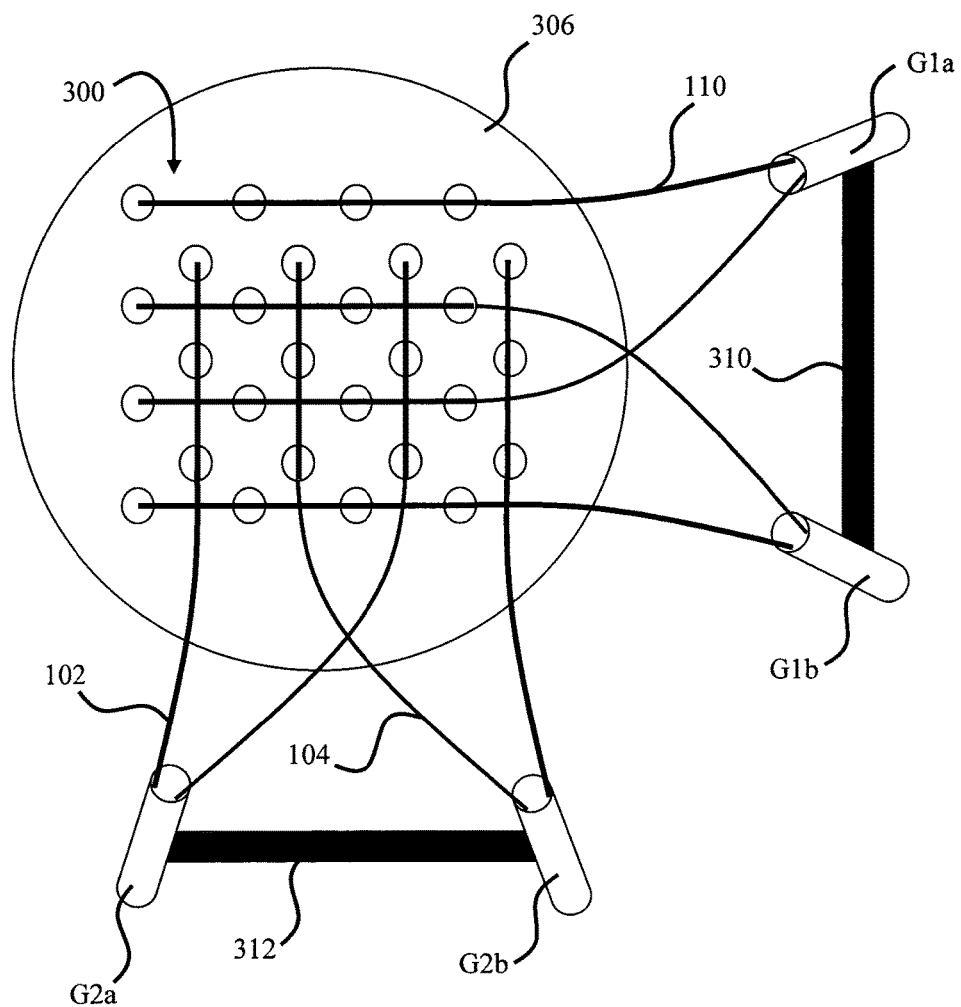
FIG. 5 is a schematic drawing illustrating an example of a possible set of the wiring array of FIG. 4.

Referring now to FIG. 5, an example is illustrated of a possible set up of the net structure of a wiring array of FIG. 4

In the net structure array 300, the groups G1 and G2 are divided into sub-groups G1a and G1b, and G2a and G2b, respectively. It should be understood that there may be any number of sub-groups for each group, and not necessarily the same number for both groups. Sub-groups belonging to the same group are separated by a relatively large distance. Furthermore, adjacent bundles belonging to the same group belong to different subgroups. In other words, the sampling lines of different sub-groups of the same group are arranged in an alternating fashion. For example, the bundles 102 and 104 are adjacent bundles belonging to the same group G2. However, the bundle 102 belongs to the subgroup G2a, while the bundle 104 belongs to the subgroup G2b. In this manner, adjacent bundles are separated by a relatively large distance between each other. The separation between the subgroups G1a and G1b is implemented via a first bundle holder 310, which firmly holds the subgroups G1a and G1b at a desired distance from each other. Similarly, the separation between the subgroups G2a and G2b is implemented via a second bundle holder 312. The bundle holders 310 and 312 are preferably chosen to be non-magnetic, so that their presence neither generates a further magnetic field nor is affected by the magnetic field in order not to affect measurements between electrodes.

The above-described setup of the net structure 300 ensures that while the electromagnetic induction loops/circuits formed by wires in the same bundle are small, the electromagnetic induction loops formed by wires in adjacent bundle are relatively large. Such a feature may be advantageous when the net structure 300 is used in the measurement of an EEG signal, and the EEG signal is analyzed/processed via an artifact recognition/suppression technique which relies on the fact that artifacts in measurements performed between electrodes that belong to different bundles (i.e. measurement across bundles) are typically larger than artifacts in measurements performed between electrodes in the same bundles (i.e. measurement along bundles). By increasing the electromagnetic induction loops between adjacent bundles, the artifacts in measurements across the bundles are increased, while the artifacts in measurements along the bundles are left unchanged. In this manner, a relation between measurements across the bundles and measurements along the bundles is significantly greater when an artifact is present, and therefore the chance of identifying artifacts via the above artifact recognition/suppression technique is increased. Examples of the above artifact recognition/suppression technique include a virtual-motion-sensor (VMS) technique (described in detail in FIG. 9) and an estimated-versus-measured (EVM) technique (described in detail in FIG. 10).

It should be noted that the use of the above arrangement of sampling lines, i.e. division into alternatingly arranged sub-groups of sampling lines, actually does not require that all the sampling lines be wire bundles. It would generally sufficient if only some of the sampling lines are constituted by the wire bundle.

Figure 6:
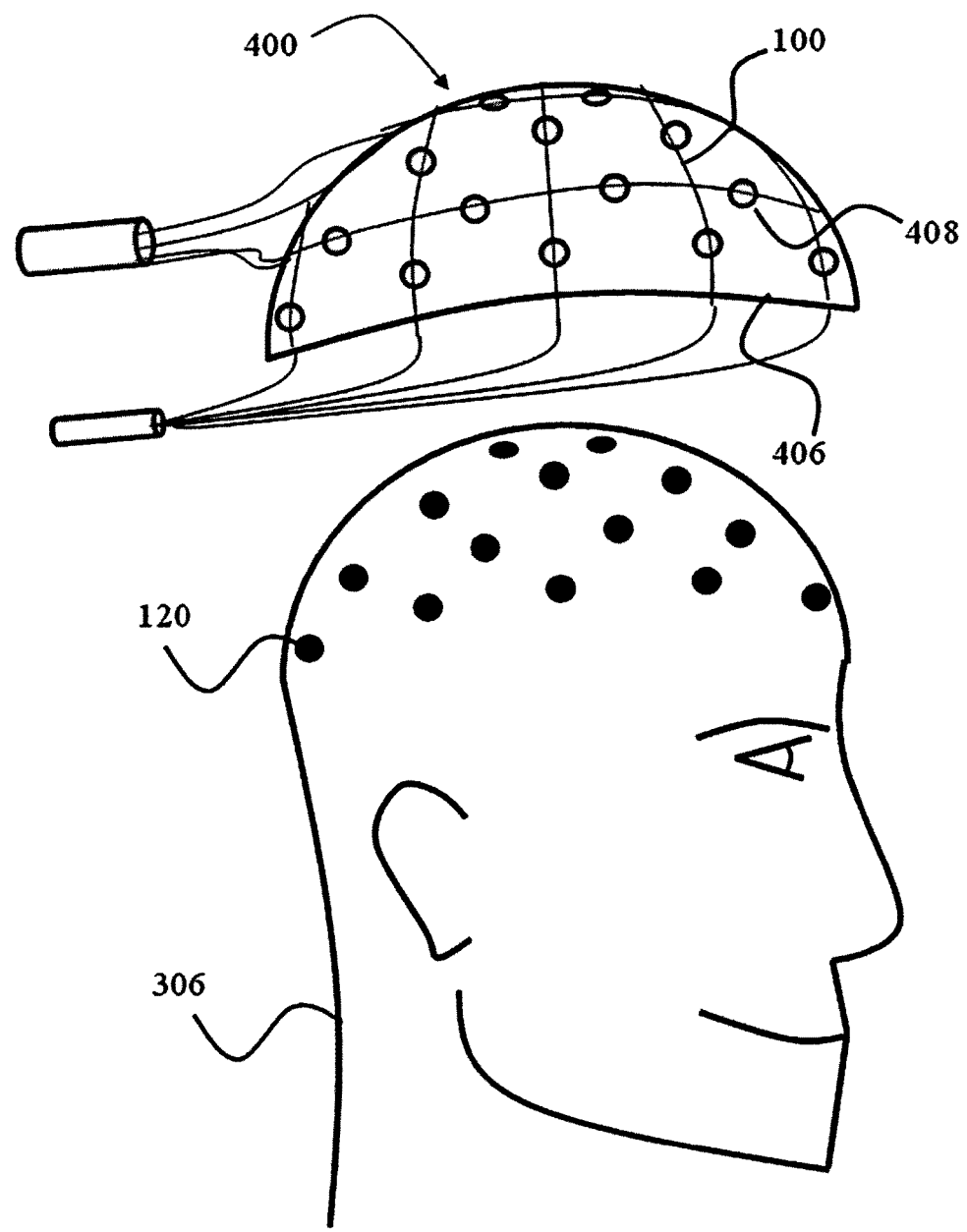
FIG. 6 is a schematic drawing illustrating a cap including the net structure of FIG. 4 designed for being worn by a patient during an EEG scan performed in the presence of a magnetic field.

FIG. 6 is a schematic drawing illustrating a cap 400 designed for being worn by a patient during an EEG scan performed in the presence of a magnetic field. The cap 400 includes a wiring array, such as the wiring array 100 described in FIG. 1 above, configured for leading EEG signals from a plurality of electrodes (such as the electrode 120) located on the patient's scalp to an EEG monitoring device. The cap 400 is configured for being worn by a patient 306, in a manner that enables the wiring array incorporated in the cap to connect an EEG monitoring device to a plurality of electrodes located on the patient's scalp.

In a variant, the electrodes are placed on the patient's scalp separately from the cap, and the cap 400 with the wiring array when worn by the patient 306, allows for connecting the wiring array of the cap 400 to the electrodes. With this configuration (i.e. electrodes' arrangement is separate from the cap), the cap 400 may include an electrically non conductive headpiece 406, which sports an inner surface designed for being fitted to the patient's head and an outer surface designed for connecting the wiring array to said headpiece 406. The latter further includes a plurality of apertures, generally 408, for being traversed by a portion of the EEG electrodes for connecting to the wires of the wiring array. The wiring array may be glued to the outer surface of the cap 400, or secured to the cap 400, for example via fasteners located on the outer surface of the cap 400.

In yet another variant, the electrodes are initially connected to the wiring array of the cap 400 (e.g. are integral with the wiring array or connectable thereto), and the entire system formed by the cap 400 carrying the wiring array and the electrodes is put on the patient's scalp for measurements.

Optionally, the cap 400 is made of a stretchable material and carries a sufficiently flexible net of the wiring array, for closely fitting the scalp of the patient. This improves a securing of the cap 400 to the patient's scalp and limits a movement of the cap 400 with respect to the patient. In this manner, motion artifacts generated by a motion of the cap 400 independent of the patient are reduced.

Figure 7:
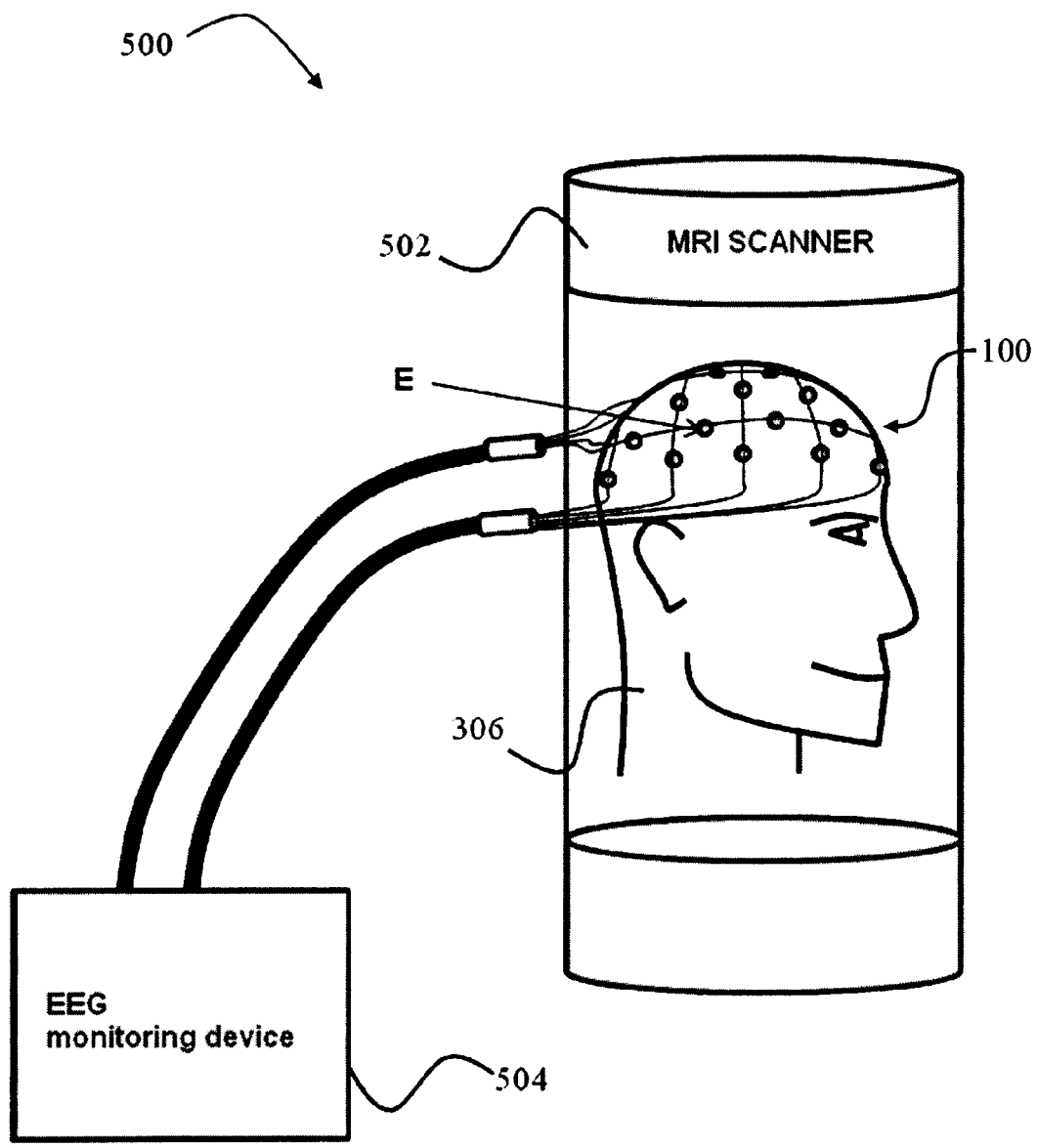
FIG. 7 is a schematic drawing illustrating a system for simultaneous EEG and MRI scans, utilizing the wiring array (net structure) of the invention.

Reference is now made to FIG. 7 which is a schematic drawing illustrating a system 500 for simultaneous EEG and MRI scans, using a wiring array of the present invention. The system 500 includes an MRI scanner 502 for imaging the patient's brain, an EEG monitoring device 504, a plurality of EEG electrodes, generally at E, designed for being placed at predetermined locations on the scalp of a patient 306 and for detecting neural signal signals, and a wiring array 100, as described above in reference to FIG. 1, for relaying the neural signals to the EEG monitoring device 504 for analyzing the signals and generating EEG data. The MRI scanner 502 may be, for example, an fMRI scanner.

The EEG data taken simultaneously with MRI scans is affected by a decreased presence of motion artifacts, due to the presence of the wiring array 100, as explained above. Furthermore, due to the net structure of the wiring array, the neural signals are detected along two directions, facilitating neural signal detection and interpretation with high precision. The provision of the two-dimensional wiring array enables the EEG monitoring device to perform an accurate reconstruction of any neural signal vector (amplitude and orientation of any neural signal) by simple trigonometric computations, as explained above. The wiring array is applied to the patient 306 either directly, as described with reference to the net structure 300 of FIG. 4, or by using a cap, as described above, with reference to FIG. 6.

In a variant, instead of the MRI scanner 502, a TMS coil device is present, to generate a changing (optionally fluctuating) magnetic field. The signal to noise ratio of the EEG measurements during TMS (due to eliminating or at least significantly reducing a contribution of motion related as well as gradient-artifact related components in the measured signal) and the interpretation of the measured EEG data are improved due to the use of the wiring array 100, as explained above.

Figure 8:
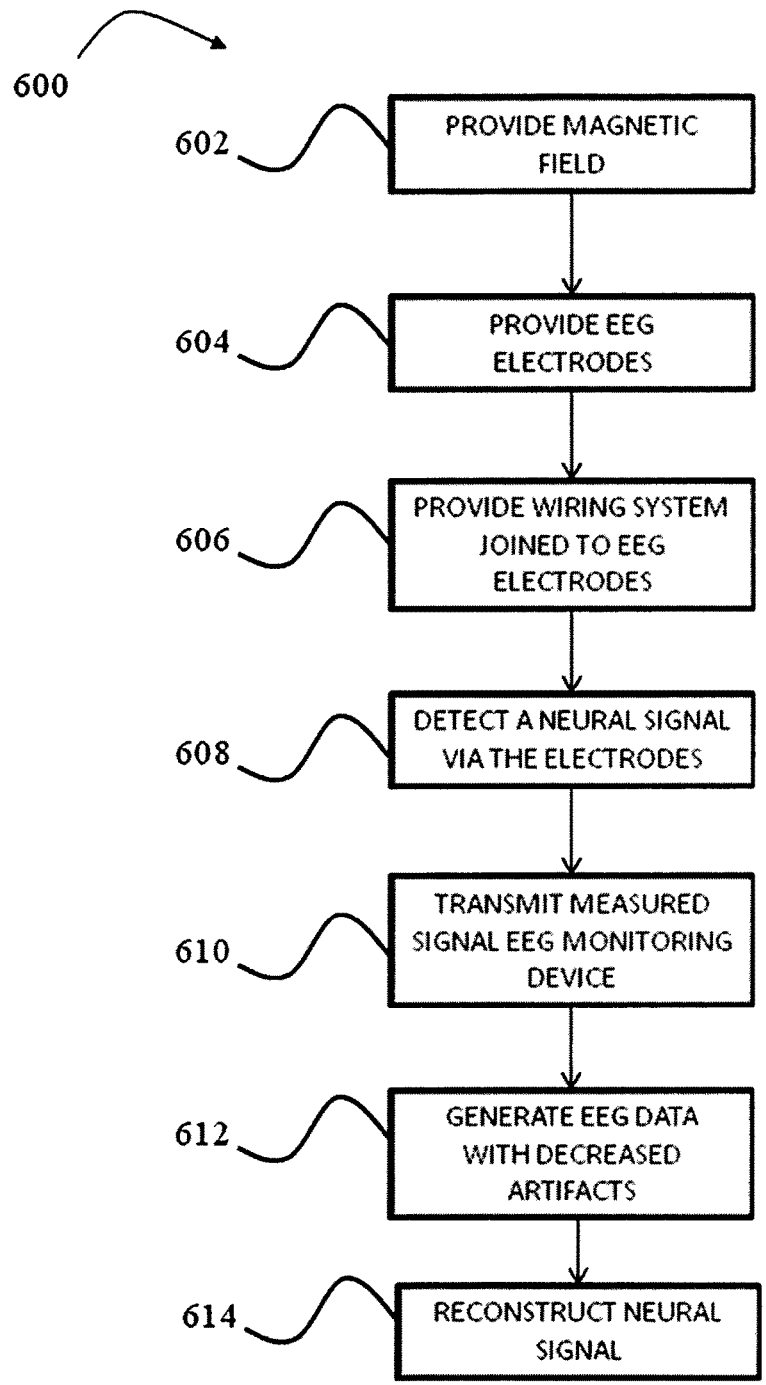
FIG. 8 is a flowchart illustrating a method for performing an EEG measurement in the presence of a magnetic field, according to some embodiments of the present invention.

Referring now to FIG. 8, a flowchart 600 is shown illustrating a method for performing an EEG measurement in the presence of a magnetic field.

Initially, a magnetic field is provided (step 602) and EEG electrodes joined to a patient's scalp are provided (step 604). The magnetic field may be constant or varying, such as a magnetic field provided by an operation of an MRI scanner (for example a fMRI or MRS scanner); the magnetic field may be varying (or fluctuating), such as the magnetic field provided by a TMS coil device. The electrodes may be disposed in a desired configuration, for example according to the International 10-20 system. A wiring array (or net structure) is placed on the patient's scalp for connecting the EEG electrodes to an EEG monitoring device. The wiring array can be placed in a separate step (step 606) or together with the placement of electrodes in case the wiring array and the electrodes are initially configured into an integral device. The wiring array is generally similar to an array as described in FIG. 1, and may be placed upon a patient's scalp either directly, as shown in FIG. 4, or with the aid of a cap, as shown in FIG. 6.

At 608, a signal is measured by the electrodes. The measurement may be bipolar or referential, as explained above in the description of FIG. 1. If a bipolar measurement is performed between two electrodes connected to the same bundle, the measurement is affected by a decreased motion and/or gradient artifact, as explained above. If a referential measurement is performed, virtual bipolar montage is performed (usually in the EEG monitor) to yield EEG data indicative of the neural signal between electrode pairs belonging to the same bundle, such that the EEG data is affected by a decreased motion and/or gradient artifact.

At 610, the EEG measurement is transmitted via the wiring array to an EEG monitoring device, and EEG data is generated (step 612).

The EEG data can be processed in order to reconstruct an amplitude and orientation of the detected neural signal (step 614).

Figure 9:
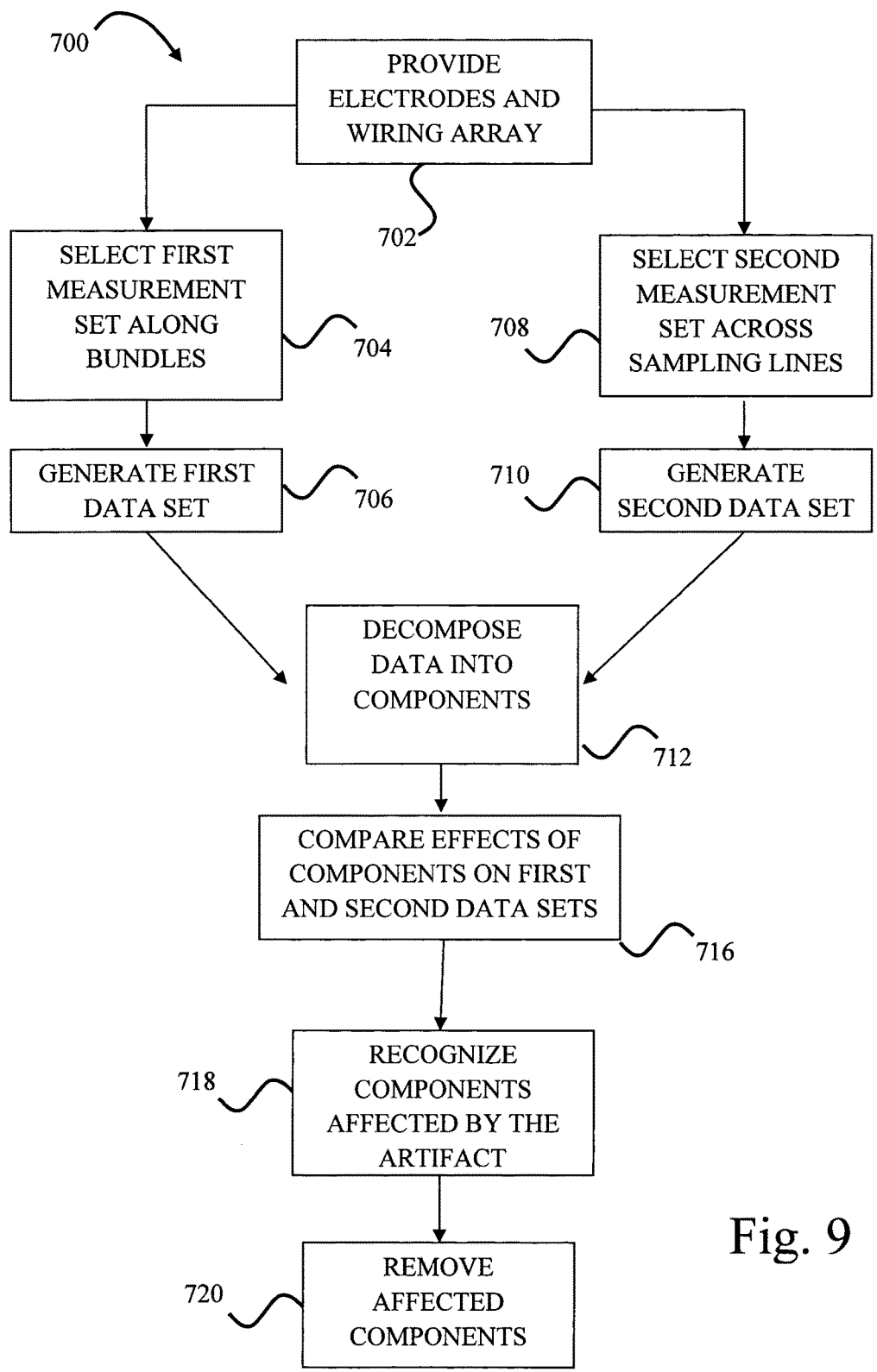
FIG. 9 is a flowchart illustrating an example of a method of the present invention for recognizing and suppressing an artifact generated in an EEG measurement in the presence of a magnetic field.

Referring now to FIG. 9, there is shown a flowchart 700 exemplifying a method of the invention for recognizing and suppressing an artifact (e.g. motion artifact and/or an gradient artifact) generated in an EEG measurement in the presence of a magnetic field. It should be noted that this method provides for effective EEG measurement using either one of the wiring arrays of FIGS. 1, 4 and 12. This technique of the invention actually presents a so-called "virtual motion sensing" (VMS), and is capable of detecting and suppressing both BCG and NBCG interference related to any motion, i.e. rigid body and non-rigid body motion. EEG electrodes, a wiring array, and magnetic field are provided (step 702). The electrodes are disposed along a patient's scalp according to a desired configuration, for example according to the International 10-20 system. The wiring array includes different sampling lines, at least one of which is a bundle of wires tightly held together; the remaining sampling lines may include a single wire. The sampling lines may be arranged to be parallel to each other, non parallel to each other, or crossing to form a net array (as shown in FIG. 1 for example, or as either one of bundle groups $G_1$ or $G_2$ of FIG. 1, and the wire bundle may be configured as shown in FIG. 2 for example). The EEG electrodes are connected to an EEG monitoring device via the wiring array, and the patient is introduced into a device which provides the magnetic field (such as an MRI scanner, or a TMS coil device, for example).

Then, the EEG measurement session is performed in the presence of the magnetic field. In this connection, it should be understood that for the purposes of this embodiment of the invention, two sets of measured signals are to be collected from selected sets of electrodes. Thus, first and second sets of bipolar EEG measurements are substantially simultaneously performed (steps 704, 708). The first set of measurements includes bipolar measurements performed only between pairs of electrodes connected to the same bundle (measurements along bundles). It should be noted that the first measurement set is not limited to a single bundle. Indeed, the measurements may be performed along different bundles, but only between electrodes connected to the same bundle. The second set of measurements includes bipolar EEG measurements performed only between pairs of electrodes connected to sampling lines (measurements across sampling lines). The so obtained first and second sets of measured signals are transmitted to different channels of an EEG monitor via the wiring array, and corresponding first and second sets of EEG data indicative of the measured signals are generated (steps 706 and 710).

Both the first and the second sets of EEG data are decomposed into a plurality of components, according to a common separation algorithm (step 712). The separation algorithm may employ, for example, principle component analysis (PCA) and/or independent component analysis (ICA).

When using ICA, we assume that we observe n linear mixtures of n independent components:

$$x_i = w_{i1}s_1 + w_{i2}s_2 + \ldots + w_{in}s_n, \text{ for all } i \quad \text{Equation 5}$$

In this equation, it was assumed that each mixture $x_i$ as well as each independent component $s_j$ are random variables and $x_i(t)$ and $s_j(t)$ are samples of these random variables changing in time. Therefore, $x_i(t_1)$ is a sample of the variable $x_i$ at a time point $t_1$. Similarly, $s_j(t_1)$ is a sample of the component $s_j$ at a time point $t_1$.

A vector x is a vector whose elements are the mixtures $x_1 \ldots x_n$. A vector s is a vector with the components $s_1, \ldots, s_n$. A matrix W is the matrix containing the elements $w_{ij}$. The model can now be written:

$$x = Ws \quad \text{Equation 6}$$

The above can be expanded to $$X = WS \quad \text{Equation 7}$$

where X is an m×n matrix, W is an n×n matrix, and S is an m×n matrix, as follows:

$$X = \begin{bmatrix} x_1(t1) & x_1(t2) & x_1(t3) & x_1(t4) & \ldots & x_1(tn) \\ x_1(t1) & x_2(t2) & x_2(t3) & x_2(t4) & \ldots & x_2(tn) \\ \ldots & \ldots & \ldots & \ldots & \ldots & \ldots \\ \ldots & \ldots & \ldots & \ldots & \ldots & \ldots \\ x_m(t1) & x_m(t2) & x_m(t3) & x_m(t4) & \ldots & x_m(tn) \end{bmatrix} \quad \text{Equation 8}$$

$$S = \begin{bmatrix} s_1(t1) & s_1(t2) & s_1(t3) & s_1(t4) & \ldots & s_1(tn) \\ s_2(t1) & s_2(t2) & s_2(t3) & s_2(t4) & \ldots & s_2(tn) \\ \ldots & \ldots & \ldots & \ldots & \ldots & \ldots \\ \ldots & \ldots & \ldots & \ldots & \ldots & \ldots \\ s_m(t1) & s_m(t2) & s_m(t3) & s_m(t4) & \ldots & s_m(tn) \end{bmatrix} \quad \text{Equation 9}$$

$$W = \begin{bmatrix} w_{1,1} & w_{2,1} & \ldots & w_{n,1} \\ w_{1,2} & w_{2,2} & \ddots & w_{n,2} \\ \vdots & \vdots & \ddots & \vdots \\ w_{1,n} & w_{2,n} & \ldots & w_{n,n} \end{bmatrix} \quad \text{Equation 10}$$

The aim of ICA is to determine both the matrix W and the independent components s, while knowing only the measured variables x.

The ICA can be applied to the data generated at 706 and 710. In this case, X is the basic data matrix entering the analysis where the rows corresponds to specific electrode pairs between which measurements are taken and the columns correspond to time points. An element $x_i(t_k)$ of the matrix X is a data point generated by a measurement between an electrode pair i at time $t_k$. S is the component matrix, where each row represents a specific component and each column represents a specific time point. Each component $s_j(t_k)$ is a certain electrical signal generated at a time point $t_k$ in a certain area of the patient's body, and affects each $x_i(t_k)$ in different fashion. The manner in which $s_j(t_k)$ affects $x_i(t_k)$ depends on a number of parameters, such as the distance between the body part and the electrode pair, the type of tissues that are located between the body part and the electrode pair, etc. The effect of $s_j(t_k)$ on $x_i(t_k)$ is quantified by the weight element $w_{ij}$ of the matrix W.

Every column of the matrix W represents a list of weights which is related to one component (row of matrix S); every row of matrix W corresponds to one specific electrode pair between which measurements are taken (row of matrix X).

As for the PCA technique, it is mathematically defined as an orthogonal linear transformation that transforms the data to a new coordinate system such that the greatest variance by any projection of the data comes to lie on the first coordinate (called the first principal component), the second greatest variance on the second coordinate, and so on.

Let us define a data matrix, X, with zero empirical mean, where each of the n rows represents a different signal, and each of the m columns gives a particular time point of measurement.

The singular value decomposition of X is $X = W\Sigma V^T$, where the m×m matrix W is the matrix of eigenvectors of $XX^{-1}$, the matrix $\Sigma$ is an m×n rectangular diagonal matrix with nonnegative real numbers on the diagonal, and the matrix V is n×n.

The PCA transformation that preserves dimensionality (that is, gives the same number of principal components as original variables) is then given by:

$$Y^T = X^T W = V\Sigma^T \quad \text{Equation 11}$$

The basic matrix X which enters the analysis is an m×n matrix as shown above in equation 8, where m is the number of selected electrode pairs and n is the number of time-points. Each row of X corresponds to a certain electrode pair and each column of X corresponds to a certain time point. The matrix Y corresponds to the component matrix S of equation 9. The matrix W is the weight matrix as shown in equation 10. As above, every column of W represents a list of weights which is related to a certain component (i.e to a row of matrix Y); every row of W corresponds to a specific electrode pair between which measurements are taken (i.e. to a row of matrix X).

Each component is associated with a value which is indicative of its contribution on a signal measured between a certain pair of electrodes (and therefore on EEG data generated by the measurement). In ICA and PCA, such a value is the weight (i.e. an element $w_{ij}$ of the matrix W). Because the artifact affects the second set of measurements (across sampling lines) more than the first set of measurements (along bundles), it is expected that the value associated with the effect of one or more components on one or more pieces of data of the second set will be significantly higher than any value associated with the effect of the same components on any piece of data of the first set. The effects of the components on the first data set and the second data set are compared (step 716), and a signal component affected by an artifact is recognized (step 718), namely the specific component whose effect is significantly higher on the second data set than on the first data set. Such recognized components are the components that are affected or generated by the artifact. It should be noted that the recognized components affect both the first and second sets of data, even though the first data set is less affected. Then, the components affected by the artifact are removed both from the first data set and the second data set (step 720).

In ICA and PCA, the comparison and recognition of the artifact is performed as follows. For each component, the maximal absolute value of the element $w_{ij}$ of the matrix W is found. This is done by identifying the element $w_{MAX1}$ having the maximal absolute value at each column of the matrix W, since each column of W corresponds to a different component. For any given column, if $w_{MAX1}$ corresponds to a piece of data generated by a measurement along bundles (i.e. $w_{MAX1}$ is a matrix element on a row corresponding to a pair of electrodes connected to the same bundle), such component affects measurements along bundles (i.e. measurements of the first set) more than measurements across bundles (i.e. measurements of the second set). Therefore, the component corresponding to $w_{MAX1}$ is deemed unaffected by the artifact.

If $w_{MAX1}$ corresponds to a piece of data generated by a measurement across sampling lines, a maximal weight ($w_{MAX2}$) is identified, such that $w_{MAX2}$ corresponds to the same component and to a piece of data generated by a measurement along bundles. A relation between the absolute values of $w_{MAX1}$ and $w_{MAX2}$ is found, and compared to a predetermined threshold. If the relation is above or below the threshold (depending on the nature of the relation), i.e. if the absolute value of $w_{MAX1}$ is significantly higher than the absolute value of $w_{MAX2}$, then the component corresponding to $w_{MAX1}$ and $w_{MAX2}$ is recognized as an artifact-affected or artifact-generated component and is therefore removed. Otherwise, the component is retained. According to a non-limiting example, the relation between $w_{MAX1}$ and $w_{MAX2}$ is the ratio R, where $$R = \frac{|w_{MAX2}|}{|w_{MAX1}|} \qquad \text{Equation 12}$$

R can assume a value between 0 and 1. If R is lower than a predetermined threshold, the component is removed. If R is higher than the predetermined threshold, the component is retained.

This comparison and recognition process is performed for each column of the matrix W, and each component corresponding to the given column is either removed or retained, as described above. After such process, a corrected signal can be recomposed using only the retained components. The corrected signal is a signal which is significantly unaffected by the artifact.

The selection of the threshold that differentiates artifacts from neural components defines whether the VMS technique is strict or permissive. A strict VMS technique ensures that most of the artifacts are detected and removed, and therefore greatly reduces artifact-generated noise. However, it can also mistakenly identify components generated by brain as artifacts, and thereby delete data that may contain important information. One the other hand, a permissive VMS technique ensures that most neural components are recognized as such and retained. However, the application of a permissive VMS technique on EEG measured data may lead to mistakenly retain artifact-affected or artifact-generated components, adding noise to the reconstructed corrected signal.

According to a non-limiting example, tests performed by the inventors have determined that a possible permissive VMS technique may be achieved by recognizing as artifacts such components in which the absolute value of maximal weight across bundles is more than twice higher than the absolute value of maximal weight across bundles (i.e. if R<0.5). In contrast, in a possible strict VMS technique, components recognized as artifacts are components in which $w_{MAX1}$ and $w_{MAX2}$ correspond to pieces of data generated by measurements across bundles.

Figure 10:
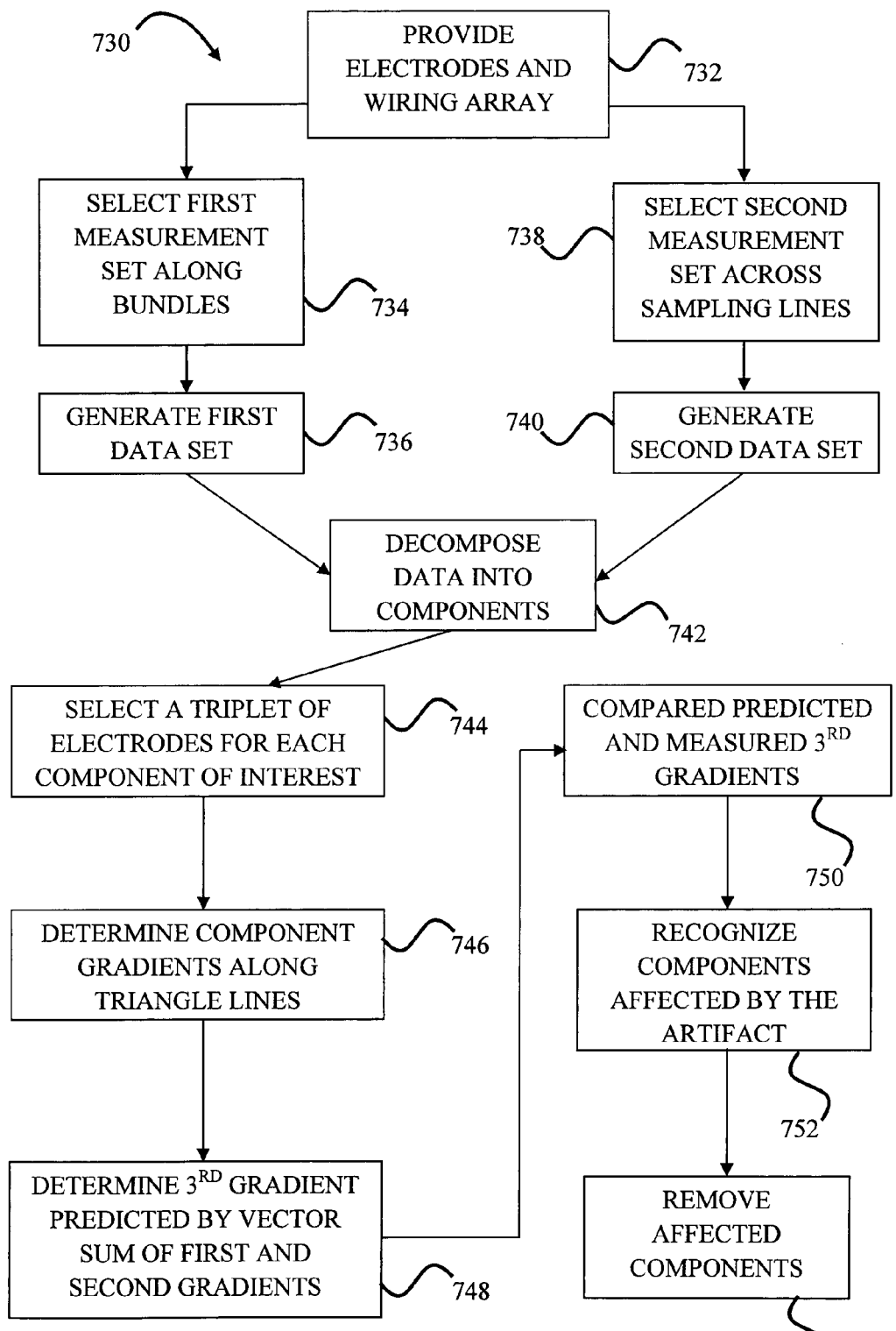
FIG. 10 is a flowchart illustrating an example of a method of the present invention, in which an artifact generated in an EEG measurement in the presence of a magnetic field is recognized and suppressed, by using considerations regarding the geometrical configuration of three electrodes.

Referring now to FIG. 10, a flow chart 730 exemplifies another (second) method for recognizing and suppressing an artifact (e.g. motion artifact and/or an gradient artifact) generated in an EEG measurement in the presence of a magnetic field. The method 730 is based on the fact that a source of electric field inside a patient's head produces electric potentials (neural signals) that are predictably distributed between EEG electrodes according to the electrodes' positions on the scalp. Conversely, signals induced by movements of head and EEG cables inside magnetic field (motion artifacts) or by a changing magnetic field (gradient artifacts) are dependent on the whole electric loop configuration (head and wires) and not only on EEG electrode locations on the scalp, and are therefore not predictably distributed over the head's surface. This feature can be used to separate neural signals from artifacts generated by the presence of the magnetic field. It should be noted, however, that the method 730 is more effective when the distances between electrodes A, B, and C are substantially smaller than the circumference of the head. This is because the head is a volume conductor has an irregular shape, and the homogeneity of conductor surface and conductor volume is larger when the electrodes A, B, and C are close to one another (in the same region). In this manner, it can be ensured that a neural signal propagating through the head toward the three electrodes is affected by the very similar volume and/or surface characteristics of the head. This, in turn leads to an increase in the predictability of the neural signal measured between one pair of the electrodes based on the neural signal measured between the two remaining electrode pairs. The method 730 of the invention will be hereafter referred to as an estimated-versus-measured (EVM) technique, and is capable of detecting and suppressing both BCG and NBCG interference related to any motion.

In step 732, an electrode array and a wiring array are provided, such that at least some measurements can be performed between electrodes not connected to the same sampling lines. Optionally, the electrode array also includes one or more bundles (as described, for example, in FIG. 2) to enable measurements between electrodes connected to the same bundle. At 738, measurements across sampling lines are selected, and at 740, a data set indicative of such measurements across sampling lines is generated (in a manner similar to steps 708 and 710 of FIG. 9). Optionally, but not necessarily, if one or more bundles are present in the wiring array provided in step 732, then measurements along bundles are selected at 734 and a data set indicative of such measurements along bundles are is generated (in a manner similar to steps 704 and 706 of FIG. 9). At 742, the full data set (whether it comprises only data indicative of measurements across bundles, along bundle, or both) is decomposed into components, similarly to the step 712 of FIG. 9. Following the decomposition into components of step 742, a triplet of electrodes (named, for example A, B, and C) is selected for one or more component of the measured signals at 744. In each triplet, at least one of the electrodes is connected to a sampling line to which the other two are not connected. For example, this may be achieved when all three electrodes are connected to three different sampling lines or when two of the electrodes are connected to wires of the same bundle while the third electrode is connected to a different sampling line. In a preferred embodiment, a triplet corresponding to a specific component is chosen by identifying the highest effect of the specific component on a bipolar measurement, and determining a first pair of electrodes (for example A and B) corresponding to such bipolar measurement. After the first pair has been found, two more adjacent electrode pairs are selected (pair BC and pair AC), such that a bipolar measurement has been performed in steps 734 and/or 738 between the electrodes corresponding to both pairs. In this manner, a triangle ABC is formed between the electrode triplet. The selection of the pair corresponding to the component's maximal effect is especially advantageous in ICA or PCA, where components typically approximate the signals generated by physical independent sources, when such component values are at or near their maximal values. Conversely, at or near their minimal values, the ICA or PCA components may not correspond to any physical source at a given location, and are rather spurious signals artificially created by the mathematical operations of ICA or PCA.

If the components have been determined via ICA or PCA, then the maximal effect of a specific component corresponds to the element $w_{ij}$ (weight) having the maximal absolute value on the column of matrix W which corresponds to specific component. The row to which the element $w_{ij}$ belongs is used in order to determined the first pair of electrodes.

Following the selection of the electrode triplet, for each of the components of interest, an analysis is performed on the gradients of each component along respective sides of the triangle formed by said electrodes. Steps 746-754 described below describe in detail this analysis of gradients.

At 746, the component gradients along the lines of the triangle defined by the triple of electrodes or values indicative of (e.g. proportional to) such component gradients are identified. If the components were determined by ICA or PCA, the values indicative of such component gradients are the weights corresponding to the three electrode pairs.

At 748, a vector sum of two gradients of the component along two of the triangle's sides is performed, in order to predicted the component's gradient along the triangle's third side. Alternatively, the vector sum of two values indicative of such two gradients is performed, in order to predict the third value indicative of the component's gradient along the triangle's third side. At 750, the predicted component (or value indicative thereof) is compared to the component's gradient along the triangle's third side determined during the decomposition step 742 (or to the value indicative of the third component, as determined during the decomposition step 742). As explained above, if the source of the component is originated inside the head, the vector sum of the component's gradients along the lines AB and BC is a vector along the line AC; conversely, if the component is an artifact (induced by movement of EEG electrode cables and/or of an EEG amplifier inside magnetic field and/or by a changing magnetic field), the component's gradient along the line AC does not correspond to vector sum of the component's gradients along the lines AB and BC. Thus the comparison between the third gradient predicted at 748 and calculated at 742 enables the identification of components affected or generated by an artifact, at 752. This may be done, for example, by determining a relation (such as a ration or a difference, for example) between the predicted third gradient and the calculated third gradient, and comparing the relation to a threshold value. The component is therefore deemed to correspond to a physical source within the brain or to an artifact according to the result of the comparison to the threshold value. At 754, the components affected or generated by an artifact are removed, while the components deemed to be generated by the brain are retained. After step 754, a corrected signal can be recomposed using only the retained components. The corrected signal is a signal which is significantly unaffected by the artifact.

It should be noted that even though, the steps 744 to 754 relate to using measurements between a triplet of electrodes for identifying artifacts, the present invention is not limited to such feature. Rather, any number N of electrodes may be used for each component, as long as N>2 and as long as at least two of the electrodes are connected to the same bundle while at least one of the electrodes is connected to a different sampling line. In such case, the estimated component (or value indicative thereof) is found by a sum of N−1 vectors extending along the sides of the N-sided polygon formed by the N electrodes. The estimated component (or value indicative thereof) and is then compared to the component (or value indicative thereof) determined during the decomposition step 742 in order to establish whether the component is of neural origin or an artifact.

It should be noted that though the EVM technique described in the method 730 may be applied to identify and suppress artifacts by itself, the EVM technique may be performed in conjunction to another artifact identification technique, in order to increase the discriminative power such technique. For example, the steps 744 to 752 of the method 730 may be added between the steps 718 and 720 of the VSM method 700 of FIG. 9. In this manner, at least some of the components that are deemed to be affected or generated by an artifact in the method 700 can be further analyzed in order to avoid mistakenly classifying components generated by physical portion of the brain as artifact-affected or artifact-generated. The addition of such additional steps to the method 700 may also classify some components the source which cannot be classified with certainty after the analysis of the method 700. Similarly, the VSM (method 700) technique may be used after the EVM technique (method 730), in order to increase the EVM technique's discriminative power.

The method of flowchart 730 is preferably used in a system which includes a wiring array having at least one bundle to which a series of electrodes are connected and at least one sampling line which is connected to an electrode which is not connected to the bundle. This is because the artifacts are generated by all parts of the electric loop: namely, (i) the section of head between electrodes, (ii) the wires, and (iii) an amplifier (if present). When wires are close one to another, then the portion of artifact generated the section of head between electrodes is larger than the portions of artifact generated by the wires. Therefore the artifact generated within the section of the head may distributed between EEG electrodes according to the electrodes' positions on the scalp. This leads to the fact that such interference will still fit geometrical model, according to which the vector sum of the component's gradients (weights) along two sides of the triangle is equal to a vector having a direction parallel to the third side of the triangle and the magnitude of the component's gradient along the third side of the triangle. Using a net-like array of intersecting bundles array guarantees that at least one side of the triangle is defined by two electrodes not belonging to the same bundle. In this manner, a larger portion of artifact related noise is generated by the wires (rather than the head) and such noise is easy to identify since it does not obey the above-mentioned geometrical model.

Moreover, a further advantage may be attained by performing the method of flowchart 730 in a system which includes a wiring array having a net-like structure formed by two intersecting groups of spaced-apart sampling lines (which may be all or include some wire bundles, as described above in FIGS. 1-2, and FIGS. 4 to 7), as such a wiring array assists to optimal ICA or PCA components discrimination. This is because if the bundles extended parallel to a single axis, then a neural activity producing a neural signal having a gradient that is mostly in the direction of across bundles may be sampled with poor signal to noise ratio. This may lead to wrong decomposition into components, which can result in an erroneous identification of such neural signal as noise.

Figure 11:
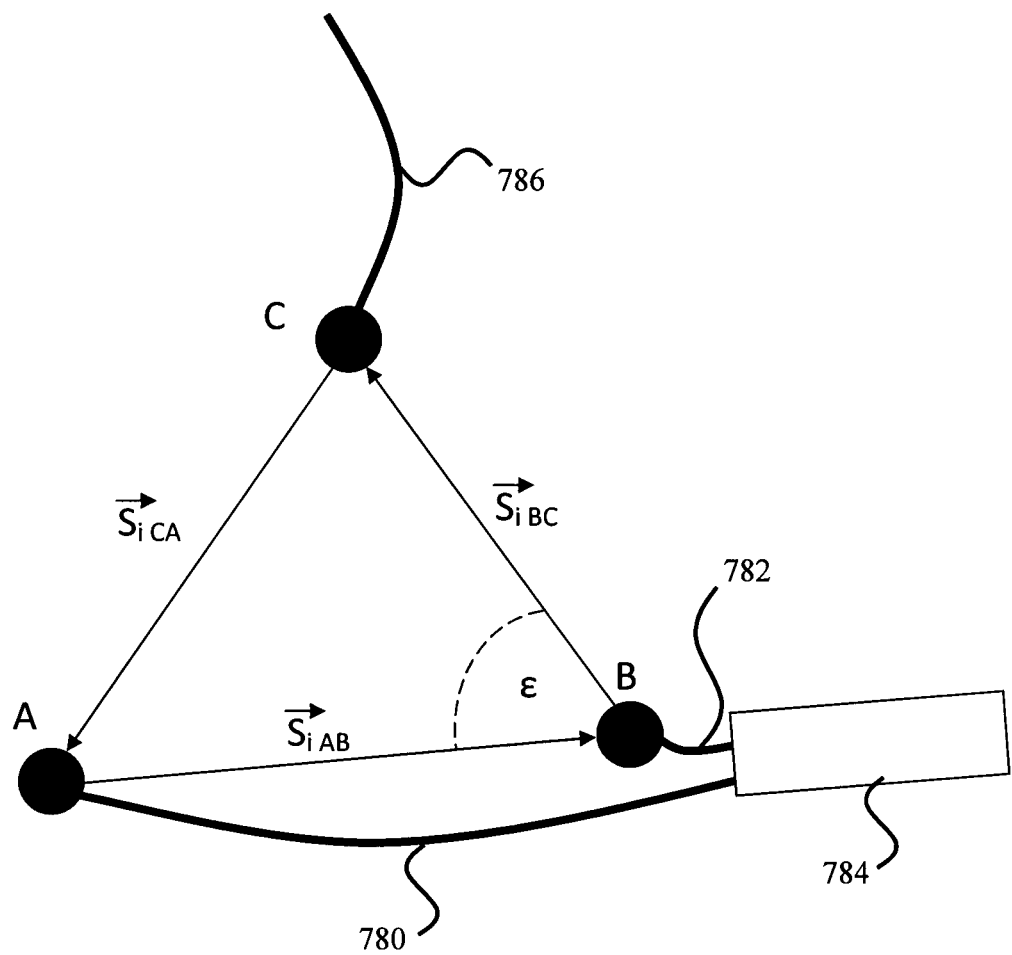
FIG. 11 illustrates an example of how the method illustrated in FIG. 9 may be applied to recognize an artifact.

Referring now to FIG. 11, an example is provided, explaining one way to apply some steps of the method 730 in FIG. 10 in order to recognize an artifact.

Three electrodes A, B, and C constitute or are part of an electrode array used for measure a plurality of signals. The electrode A and B are respectively connected to the wires 780 and 782, both wires, which may, for example, belong to a single bundle 784. The loop created by the wires 780 and 782 is therefore relatively small. Optionally, the electrodes A and B are adjacent electrodes and are connected to adjacent wires, such that the electrical loop created by the wires is even smaller. The electrode C is connected to a wire 786, which belongs to a sampling line forming a relatively large loop with the bundle 784. It should be noted that for the purposes of the EVM technique, the electrodes A and B need not be connected to the same bundle. It is, however, important that at least one of the electrode pairs (A-B, B-C, and C-A) be constituted by electrodes connected to different sampling lines. After the measured signals are decomposed into a plurality of components (see, for example, step 712 in FIG. 9, or step 742 in FIG. 10), a certain component $s_i$ is analyzed by using the electrodes A, B, and C. The component $s_i$ is calculated by using measured EEG data obtained while the EEG electrodes were within a magnetic field (e.g. generated by an MRI or MRS scanner, or a TMS device) (see, for example, steps 704, 706, 708, and 710 in FIG. 9).

A component $s_i$ has a gradient $\vec{s}_{iAB}$ in the direction from the electrode A to the electrode B, a gradient $\vec{s}_{iBC}$ in the direction from the electrode B to the electrode C, and a gradient $\vec{s}_{iCA}$ in the direction from the electrode C to the electrode A. AB, BC, and AC are the distances between the electrodes A and B, B and C, and A and C respectively. The angle $\epsilon$ is the angle between AB and BC.

Therefore, $$AC^2 = AB^2 + BC^2 - 2AB \cdot BC \cdot \cos(\epsilon) \qquad \text{Equation 13}$$

$$\cos(\epsilon) = (AB^2 + BC^2 - AC^2)/2AB \cdot BC \qquad \text{Equation 14}$$

Then the magnitude $s_{i\,CA\,EST}$ of the diagonal gradient $\vec{s}_{iCA}$ estimated by the vector sum between the gradients $\vec{s}_{iAB}$ and $\vec{s}_{iBC}$ is:

$$s_{i\,CA\,EST} = [s_{i\,AB}^2 + s_{i\,BC}^2 - 2s_{i\,AB} \cdot s_{i\,BC} \cdot \cos(\epsilon)]^{1/2} \qquad \text{Equation 15}$$

where $s_{i\,AB}$ and $s_{i\,BC}$ are the magnitudes of the gradients of the component $s_i$ between the electrodes A and B, and B and C, respectively.

A ratio T between $s_{i\,CA\,EST}$ and $s_{i\,CA}$ is defined as $$T = s_{i\,CA\,EST}/s_{i\,CA} \qquad \text{Equation 16}$$

where $s_{i\,CA}$ is the magnitude of gradient of the component s between the electrodes C and A.

When T is close to 1, the component $s_i$ can be classified as a neural signal originating within the head of the patient or test subject. If T is far from 1, the component is classified as a motion or interference artifact originating from cables or amplifier. Optionally, T is compared to a predetermined threshold in order to classify the component s. The choice of such predetermined threshold defined whether the EVM technique is strict or permissive. A strict EVM technique can efficiently recognize and suppress most artifacts, but may also mistakenly suppress neural signals. A permissive EVM retains more of the neural signals, but may also retain more of the artifacts, compared to strict EVM. According to a non-limiting example, tests performed by the inventors have determined that a possible permissive EVM technique may be achieved by recognizing as neural signals those components that satisfy the condition $0.5 < T < 2$. A possible strict EVM technique may be achieved by recognizing as neural signals those components that satisfy the condition $0.75 < T < 1.5$.

The above geometrical analysis of the component $s_i$ can be performed only if the distances AB, BC, and CA along the head's surface and the angle $\epsilon$ can be measured or calculated to a sufficient degree of accuracy. It should be noted that the head is not ideal sphere. Therefore, if the distances between electrodes are comparable with the head's circumference, an accurate measurement/calculation of the distances AB, BC, and CA and of the angle E should take into account both the changes in the head's curvature and the electrode distances along the head's surface. It is therefore preferable to keep the distances AB, BC, and CA substantially smaller than the head's circumference, in order to easily measure or calculate such distances.

Sometimes, it may be difficult to accurately measure or calculate the distances AB, BC, and CA and the angle $\epsilon$. This may be, for example, because at least one of the electrodes is within the patient's or test subject's head, as is the case in intercranial EEG. In such cases, geometrical information about the electrodes configuration used in the system (e.g. on the scalp and/or in the head) can be obtained via measurement of neural signals outside a magnetic field—provided that the same electrode array is used (or virtually recalculated via a different EEG array), and that effect of interference outside the magnetic field is substantially lower than the neural signal.

To infer the geometrical information about the electrodes' configuration, a neural signal x is measured outside the magnetic field. $x_{AB}$, $x_{BC}$ and $x_{CA}$ are gradients of the signal x along AB, BC and CA, respectively, measured outside the scanner.

$$x_{CA}^2 = x_{AB}^2 + x_{BC}^2 - 2x_{AB} \cdot x_{BC} \cos(\epsilon) \quad \text{Equation 17}$$

Therefore, $\cos(\epsilon)$ can be calculated by:

$$\cos(\epsilon) = (x_{AB}^2 + x_{BC}^2 - x_{CA}^2)/2x_{AB} x_{BC} \quad \text{Equation 18}$$

Once $\cos(\epsilon)$ is known, then the electrode array can be used for EEG measurements in the presence of a magnetic field. As above, signals are measured and decomposed into components. The component $s_i$ has gradients $\vec{s}_{ii\ AB}$, $\vec{s}_{ii\ BC}$, and $\vec{s}_{ii\ CA}$. Using equations 18 and 15, the magnitude $s_{i\ CA\ EST}$ of the diagonal gradient $\vec{s}_{ii\ CA}$ estimated by the vector sum between the gradients $\vec{s}_{ii\ AB}$ and $\vec{s}_{ii\ BC}$ is estimated. In this manner a ratio between $s_{i\ CA\ EST}$ and $s_{i\ CA}$ in the presence of magnetic field can be found, according to equation 16, in order to determined whether the signal s is a neural signal or an artifact.

Figure 12:
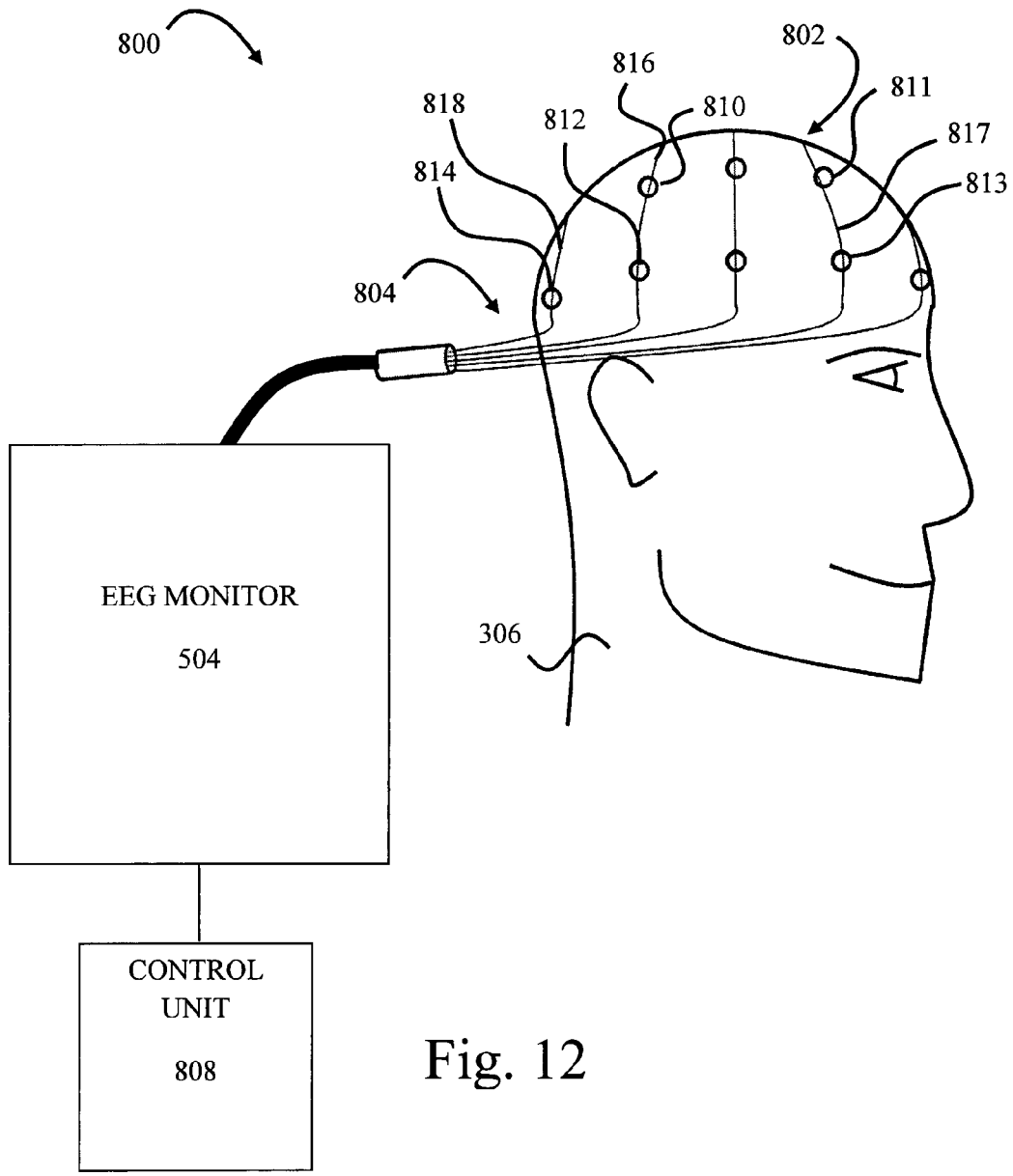
FIG. 12 is a schematic drawing illustrating an example of a system of the present invention for simultaneous EEG and MRI scans, capable of recognizing and suppressing motion artifact generated in an EEG measurement in the presence of a magnetic field.

Referring now to FIG. 12, there is schematically shown a system 800 of the present invention, for optimizing EEG measurements by recognizing and suppressing an artifact generated in the EEG measurement in the presence of a magnetic field.

The system 800 includes an electrode arrangement 802, a wiring array 804, and an EEG monitor 504. The latter is associated with a control unit 808. The control unit 808 is either a utility integral with the EEG monitor 504, or a separate unit connected to the EEG monitor 504 via wires or wireless signal transmission. The control unit includes inter alia a processing utility configured and operable for receiving and processing the EEG data from the EEG monitor 504.

In the electrode arrangement 802, a plurality of electrodes, five such electrodes 810, 811, 812, 813, and 814 being shown in the present example, are disposed along a scalp of a patient 306 according to a certain configuration, for example according to the International 10-20 system. The wiring array 804 includes different bundles (816, 817, and 818, for example) of wires tightly held together, for example as shown in FIG. 2.

The bundles may be arranged along substantially parallel axes or intersecting axes, and can thus be parallel, non parallel, or crossing. It should be understood that in this embodiment, the wiring array may or may not be formed of two groups of bundles extending along substantially perpendicular axes (as in the embodiment of FIG. 1), but may include substantially parallel bundles. However, the use of crossing bundles arrangement, e.g. a two-group net structure similar to that of FIG. 1, would even more improve the motion artifact reduction. This is because the presence of crossing bundles enables a comparison of EEG measurements performed along and across bundles between the crossing (non-parallel) bundle groups. This is particularly advantageous in cases in which the neural component of a signal (brain electric field gradient) has an orientation substantially perpendicular to one group of bundles. In such cases, if measurements were performed using a single group of non-crossing bundles, the values (for example weights) corresponding to the effect of the components on pieces of data generated by measurements across bundles would be consistently higher than the values corresponding to the effect of the same components on data pieces generated by measurements along bundles, because of the orientation of the neural signal and not necessarily because of an artifact. Therefore, even components unaffected by the interference would seem to affect the measurements across the bundles more than they affect the measurements along bundles, and would therefore be erroneously recognized as affected by an artifact and removed from the data.

In contrast, using a net structure of crossing bundles (for example, perpendicular bundle groups) enables measurements across and along bundles to be performed in two directions (across and along the first bundle group, and across and along the second bundle group). Components substantially unaffected by an artifact would greatly affect both the measurements across bundles in the group perpendicular to the neural signal and the measurements along bundles in the group not perpendicular (for example parallel) to the neural signal in about the same manner, because of the direction of the neural signal. On the other hand, components affected by an artifact would greatly affect measurements across bundles in the group perpendicular to the neural signal, but would have a lesser effect on measurements along bundles in the group not perpendicular (for example parallel) to the neural signal. Therefore, the comparison of the maximal effects of components on data generated by measurements along and across bundles in two directions is used for recognizing the artifact-affected components.

Thus, the electrodes are connected to the EEG monitor 504 via the wiring array 804. The EEG monitor 504 is designed for receiving the neural signals measured between electrode pairs and generating EEG measured data indicative thereof. The EEG monitor is capable of simultaneous reading of the measured data from multiple electrodes (electrode pairs). To this end, the EEG monitor may include a plurality of signal receiving channels, each for receiving a signal measured between a different pair of electrodes. The output of the EEG monitor 504 is thus indicative of a plurality of signals each corresponding to the measurement between a respective pair of electrodes.

The control unit 808 receives the measured data and selects appropriate data pieces for processing. The selected data pieces correspond to first and second sets of bipolar EEG measurements. The first set of bipolar EEG measurements includes measurements between at least one pair of electrodes connected to the same bundle. These may be for example the electrodes 810 and 812 connected to wires belonging to the same bundle 816, and/or the electrodes 811 and 813 connected to wires belonging to the same bundle 817. The second set of bipolar EEG measurements includes measurements performed only between electrodes of at least one pair connected to different bundles. For example, these may be the electrodes 810 and 814, and/or 812 and 813.

The control unit 808 is designed and operable for the above described selection of the measured data pieces and for processing the selected data. The processing includes decomposing each data piece (presenting differential measurements, i.e. by at least one pair of electrodes) into a plurality of components as shown in step 712 of FIG. 8. The processing may further include comparing the effect of the components on the first data set and on the second data set, and recognizing the artifact-affected signal components, satisfying a predetermined condition as described above with reference to steps 716 and 718 of FIG. 8. Additionally, or alternatively, the processing utility of the control unit 808 may include software modules configured for comparing gradients of components of measured signals to the estimates of said gradients obtained using geometrical information regarding the geometrical distribution of electrodes on and/or in the head of a patient or test subject, and recognizing the artifact-affected signal components, satisfying a predetermined condition as explained with reference to steps 744 to 752 of FIG. 10. Then the processor utility of the control unit operates for subtracting each artifact-affected component from the corresponding piece of data and generating corrected EEG data (unaffected by the artifact or having significantly reduced artifact component), as described above, with reference to step 720 of FIG. 9 and/or step 754 of FIG. 10. The control unit 808 may be preprogrammed with a certain separation algorithm, or is preferably preprogrammed with multiple algorithms of the kind specified and enables selection (by user or automatically) of a desired (optimal) separation algorithm. The control unit 808 may be programmable by a user, enabling the user to create the user's custom separation algorithm.

While various embodiments of the present invention have been described above, it should be understood that they have been presented by way of example only, and not of limitation. Those skilled in the art will readily appreciate that various modifications and changes can be applied to the embodiments of the invention as hereinbefore described without departing from its scope defined in and by the appended claims.

The following are some specific but not limiting examples of using various embodiments and aspects of the present invention as delineated hereinabove for EEG measurements using external to body and/or implanted electrodes' arrangement.

Reference is now made to FIGS. 13*a*-13*f*, illustrating graphical representations of simultaneous EEG and fMRI measurements performed on a test subject, as well as graphical representations illustrating results yielded by the application of the VMS technique of FIG. 9 on the EEG measured data.

A basic prototype of the electrode and wiring array was built. A first group of electrodes consisted of thirty electrodes connected to nine wire bundles extending parallel to a longitudinal axis, a reference electrode, and a ground electrode connected to one amplifier. A second group of electrodes consisted of thirty electrodes connected to nine wire bundles extending parallel to a transverse axis, a reference electrode, and a ground electrode connected to one amplifier connected to a second amplifier. Labels of electrodes correspond to labels of standard 10-20 montage except electrodes Tp9 and Tp10 of transverse bundle, which were located on the forehead, above the eyebrows. Reference and ground electrodes were located at FCz and AFz respectively. All wires were made of non magnetic metal. The noise reduction method of FIG. 9 was implemented in MATLAB. EEG and FMRI data was analyzed in MATLAB.

Figure 13A:
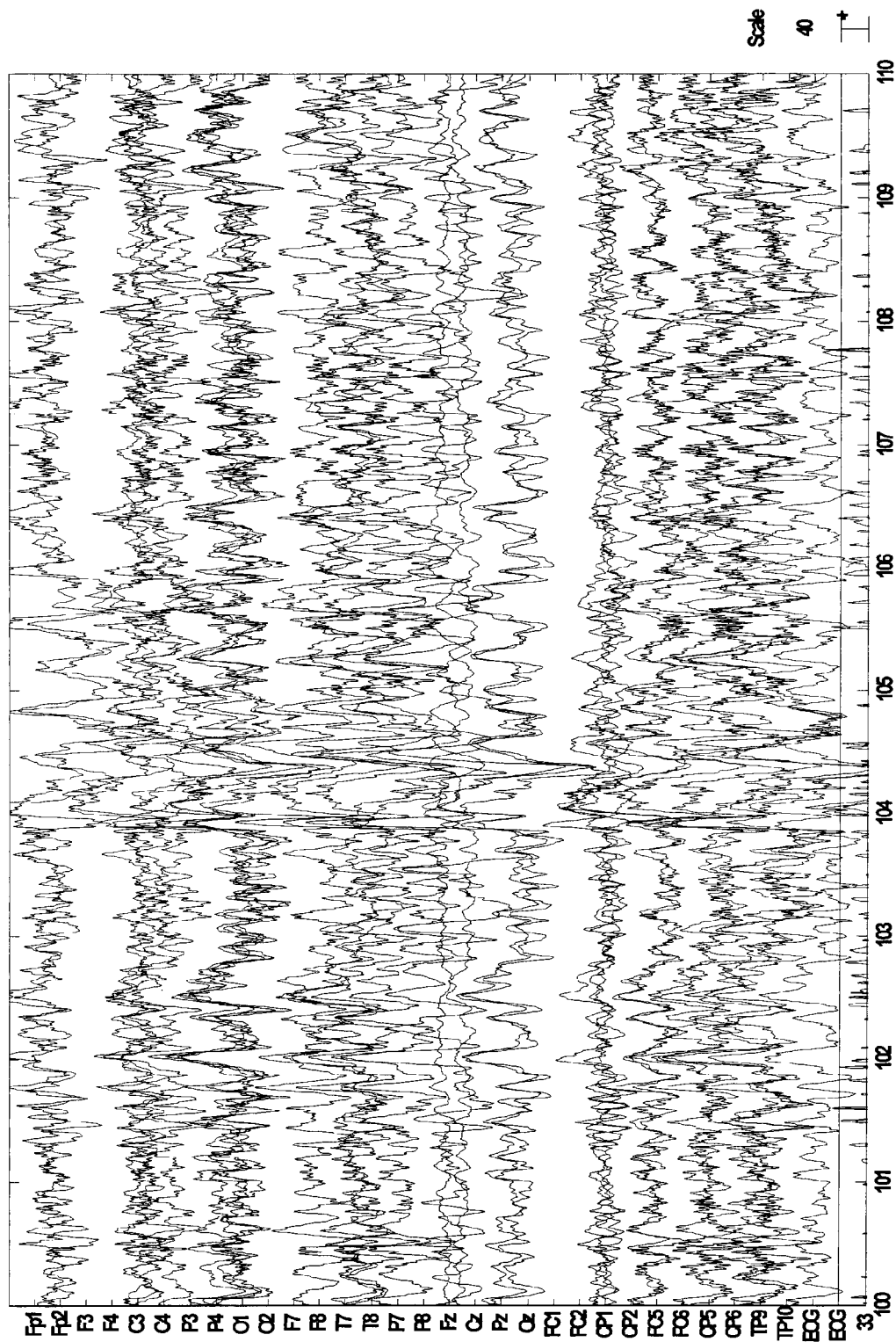
FIGS. 13a-13f illustrate graphical representations of simultaneous EEG and fMRI measurements performed on a test subject, as well as graphical representations illustrating results yielded by the application of the artifact suppressing technique of FIG. 9 on the EEG measured data.

A subject with epilepsy was scanned in simultaneous EEG-fMRI using the prototype electrode array. The subjects had epileptic activity during the scan. Results show that the use of the electrode array and the VMS noise suppression method 700 of FIG. 9 significantly reduces artifacts induced by movement inside magnetic field, and allows detecting epileptic activity occurring in a deep source (e.g., located deep inside fissure, sulcus, insula or basal brain areas) (as demonstrated by corresponding fMRI activity) and characterized by low amplitude (i.e. low magnitude of EEG signal), that cannot be seen with state of the art technology (see FIG. 13*a*, for EEG with state of the art cleaning approach, and FIG. 13*b* for EEG with the developed noise suppression method). EEG activity detection also enabled the identification of the focus of activity using the fMRI (FIG. 13*l*). The results obtained for the patient were in most cases correlated with epileptogenic zone location hypothesis. The below results suggest that the developed technology can be used effectively and reliably to identify focal epileptic activity and location of its origin in the brain.

Figure 13B:
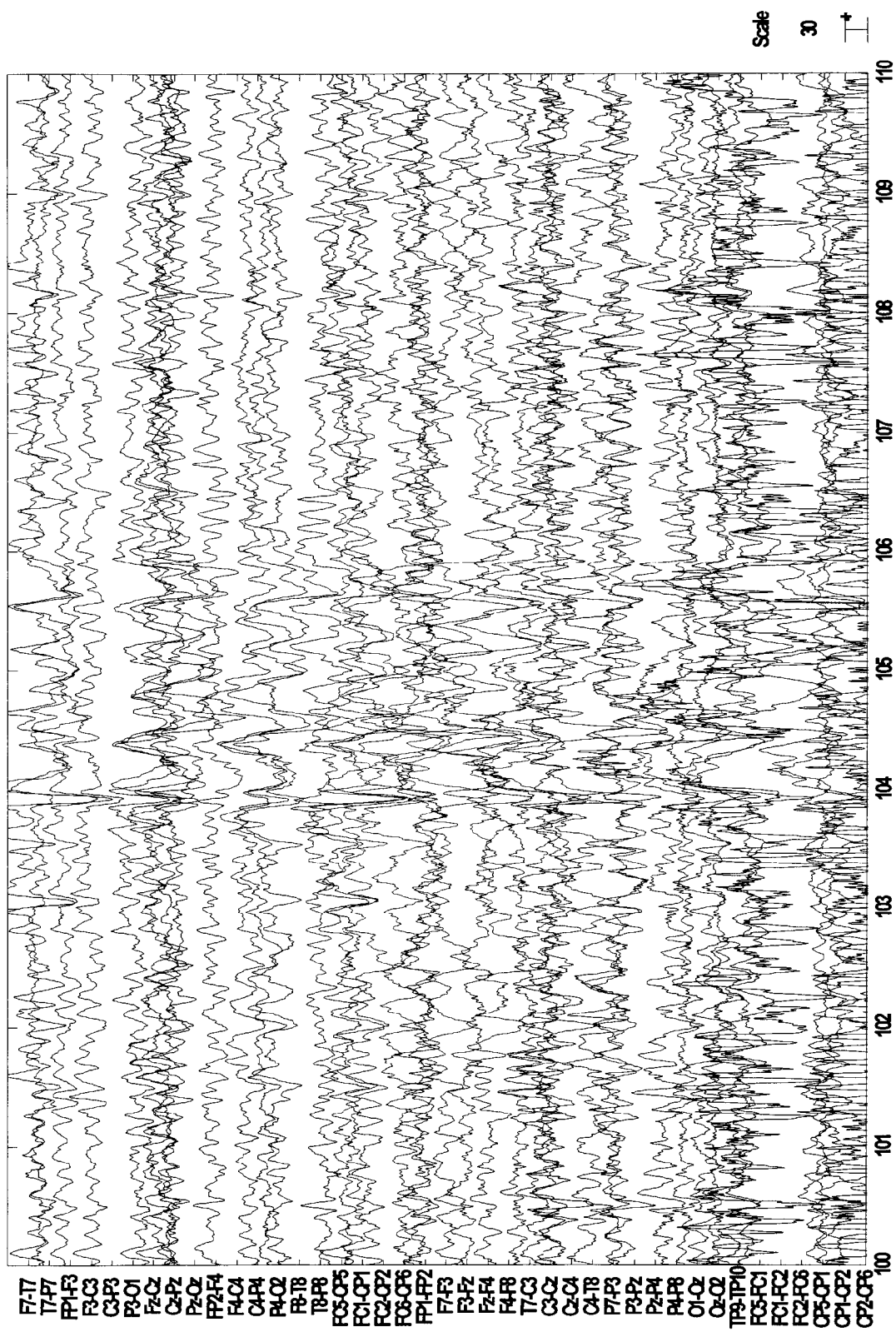
Figure 13C:
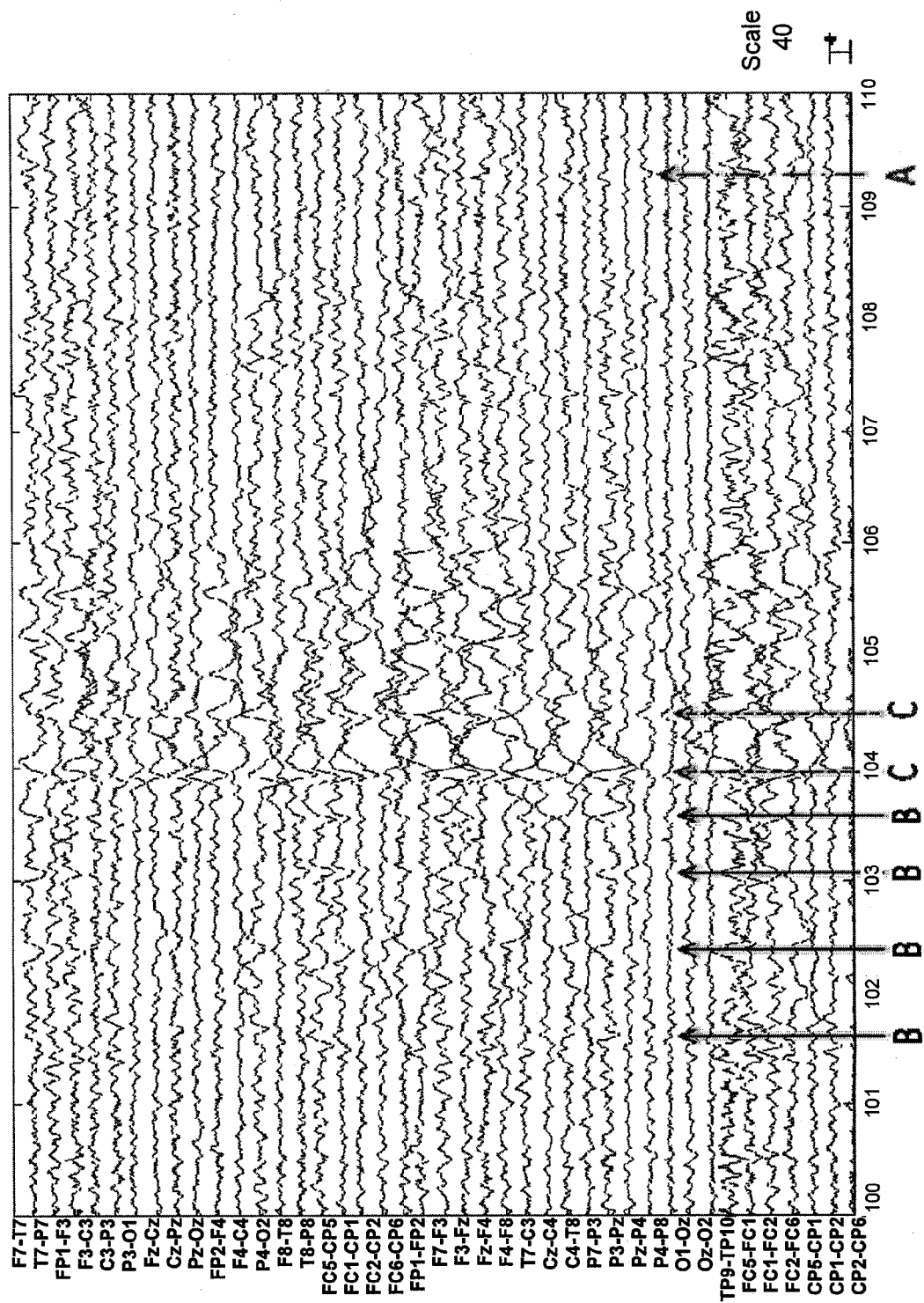
Figure 13D:
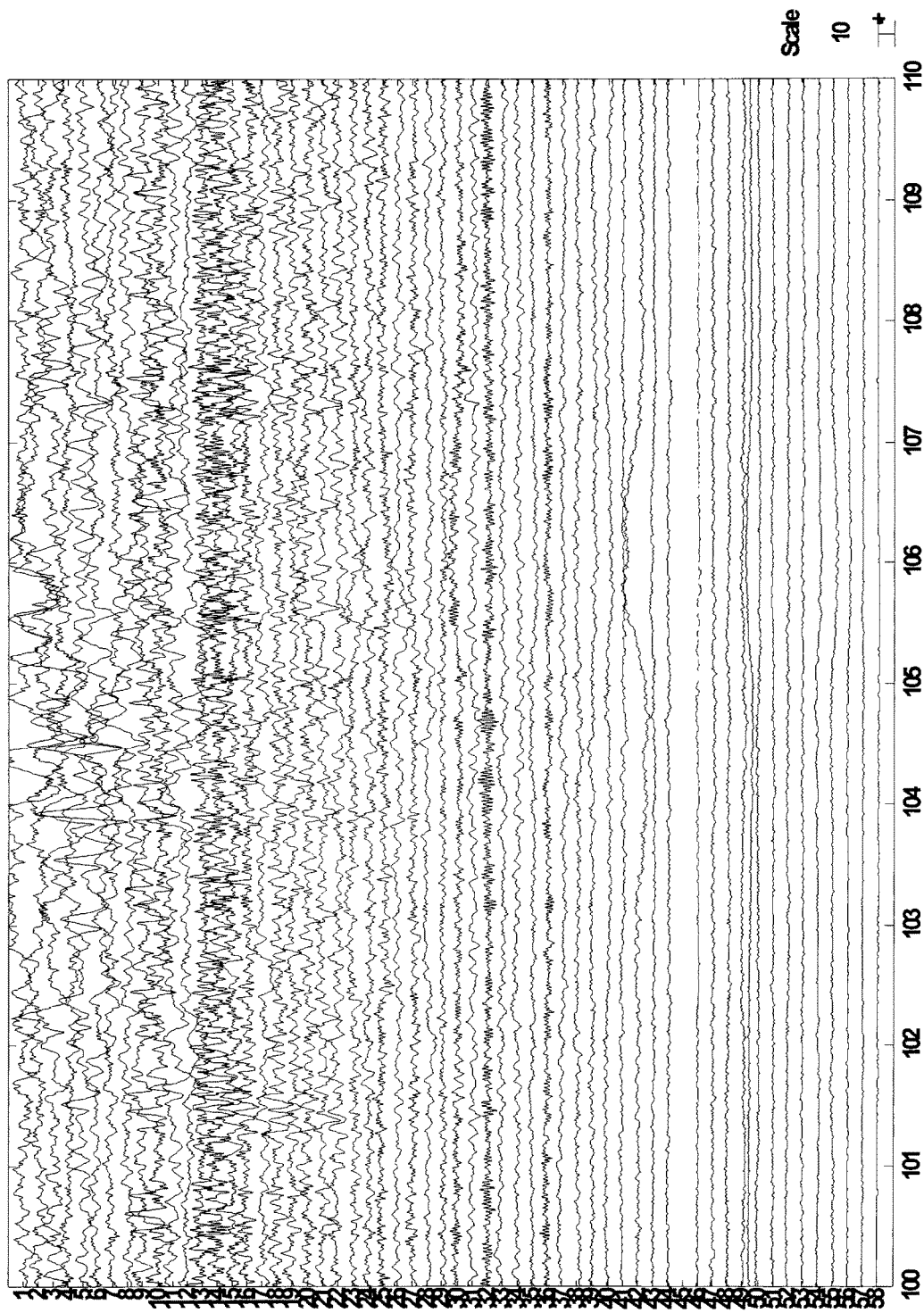
Figure 13E:
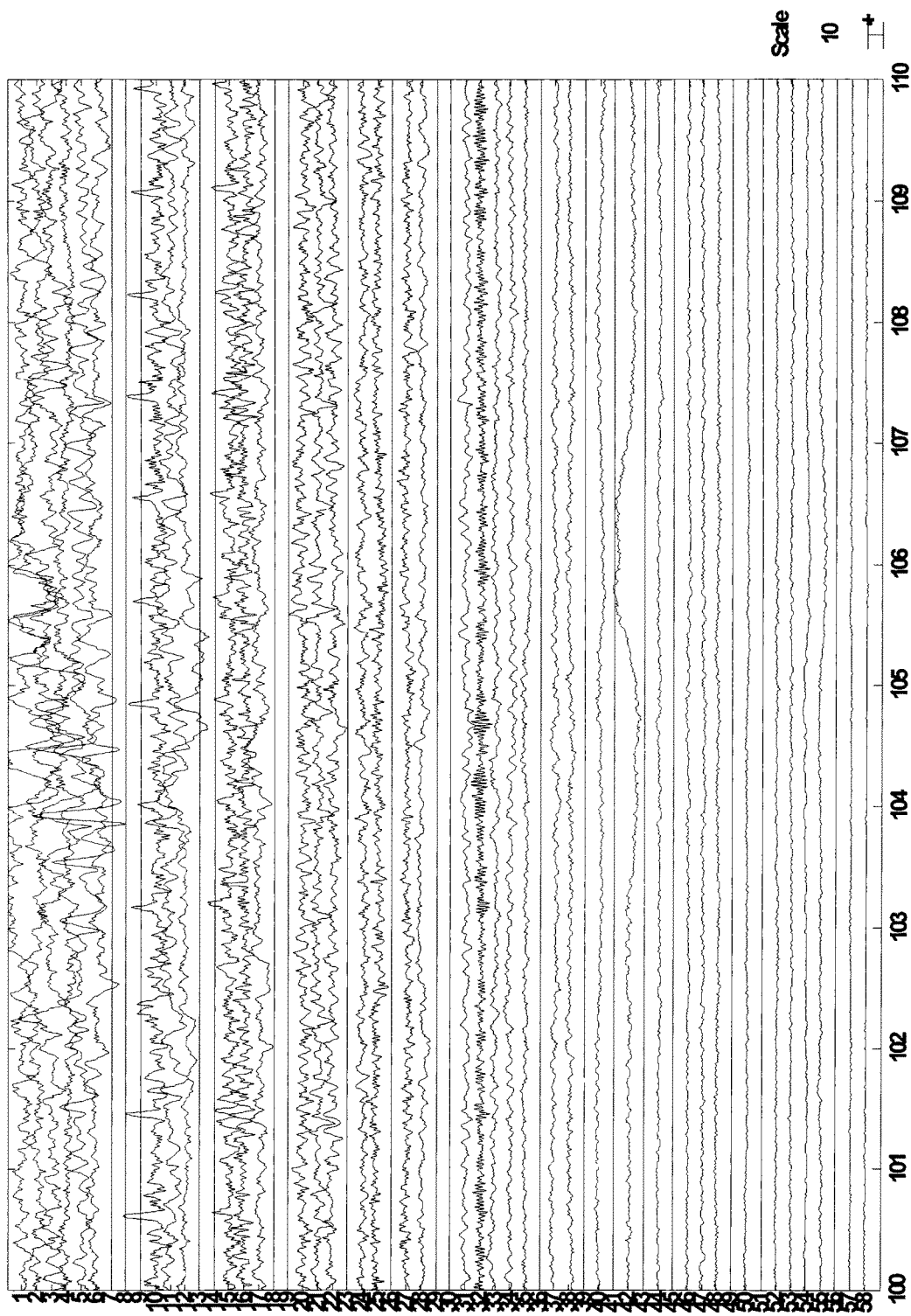
Figure 13F:
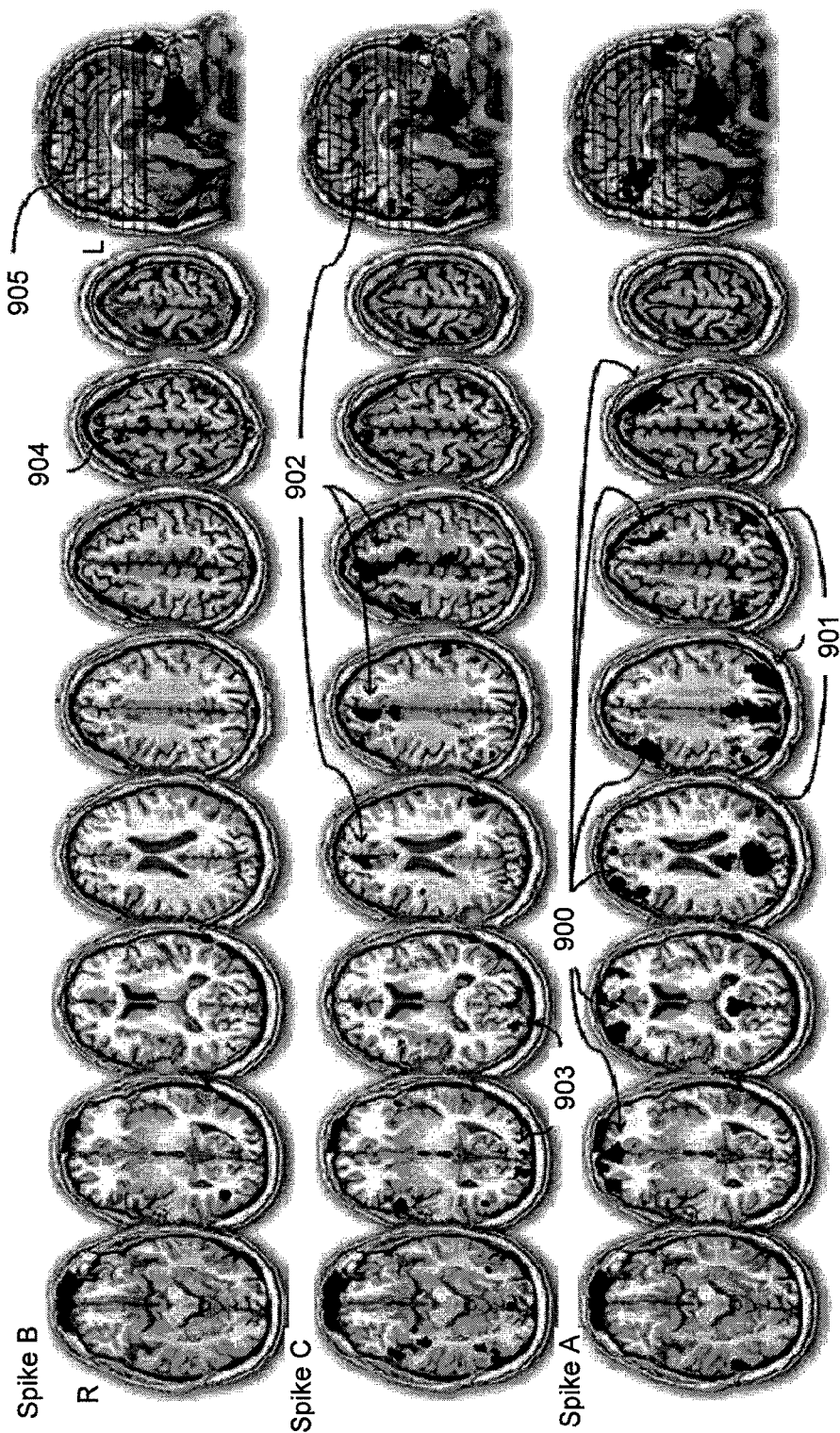

With reference to the tested subject, the semiology of the patient's seizures is vague head feeling followed by clonic left hand movements, usually without loss consciousness. Sometimes disorientation appears later. In referential EEG montage without an artifact suppressing technique, epileptic spikes were hard to detect (FIG. 13*a*). After application of the VMS technique of FIG. 9, three types of spikes were recognized in the EEG data (FIG. 13*c*). Type C was most prominent and distributed, and was the only type of spike that could be easily seen when referential montage was converted to a virtual bipolar montage, even before artifact suppression (FIG. 13*b*). As can be seen in FIG. 13*f*, which illustrates fMRI scans at different depths in the subject's brain, the type C spike is correlated with blood-oxygen-level dependent (BOLD) deactivation in bilateral, frontal, more right than left regions of the brain (the BOLD deactivation being identified by fMRI scans). Deactivation also appeared in parieto-occipital midline region.

Type A spike was according to EEG a focal, right frontal spike, mainly with transverse EEG gradient. This spike appeared mostly after type C bursts. The BOLD correlates of type A spikes include deactivation in right and left dorso lateral frontal regions 900, bilateral parietal and mesial occipito-parietal regions 901, as can be seen in FIG. 13*f*. These patterns correspond to default mode network activity, therefore they are not specific. Spike C correlates of BOLD activity include activation patterns in right frontal dorso-lateal and mesial 902 regions as well as occipital regions 903.

Type B spike was often independent, or appeared before type C bursts. Its transverse EEG gradient was mainly central. Its longitudinal gradient was mainly fronto-central. As can be seen in FIG. 13*f*, the type B spike correlated with BOLD activation in right superior frontal and dorso-lateral regions 904 with extension to the mesial surface 905. Resulting fMRI activation pattern corresponded well to the semiology of patient's seizures which were short and started by unclear head sensation, progressed to left hand clonic movements with some disorientation. More specifically, activation in right frontal mesial regions (905 and 902) close to singulate girus correspond to vague head feeling while right dorso-lateal activation (904) and right frontal mesial region activation close to SMA corresponds to clonic left hand movements.

Figure 14A:
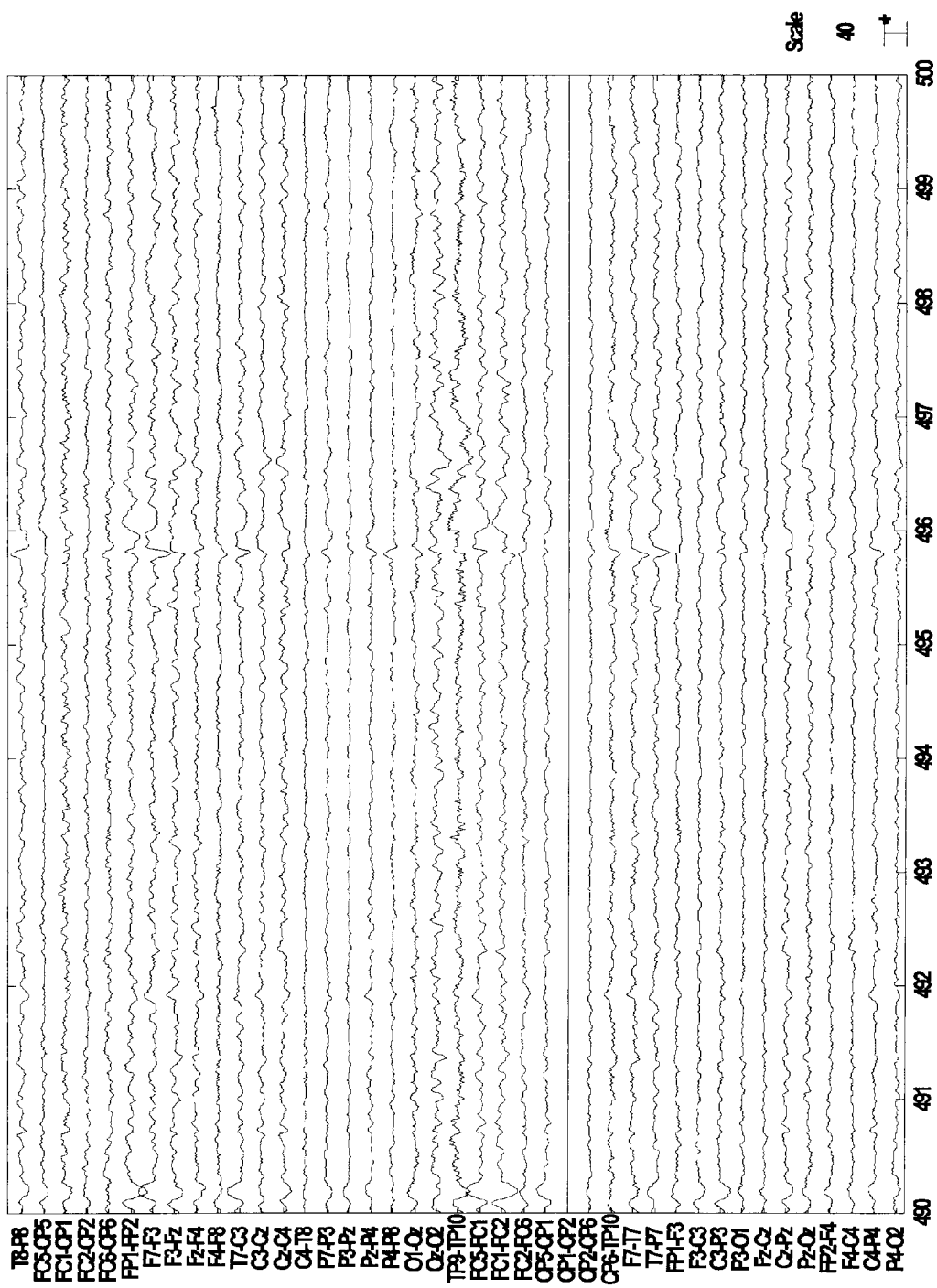

FIG. 14*a* shows a representation of an EEG signal of a test subject over time as detected by a plurality of electrode pairs. The EEG signal shown in FIG. 14*a* has been decomposed into components via ICA, and recomposed after identification and removal of components that were deemed to be artifacts according to the VMS technique described in FIG. 9. The removed components were deemed to be artifacts, since their effect was significantly higher measurement across bundles than they were on measurements along bundles. A small epileptic spike is observable just before 496 seconds of recording.

Figure 14B:
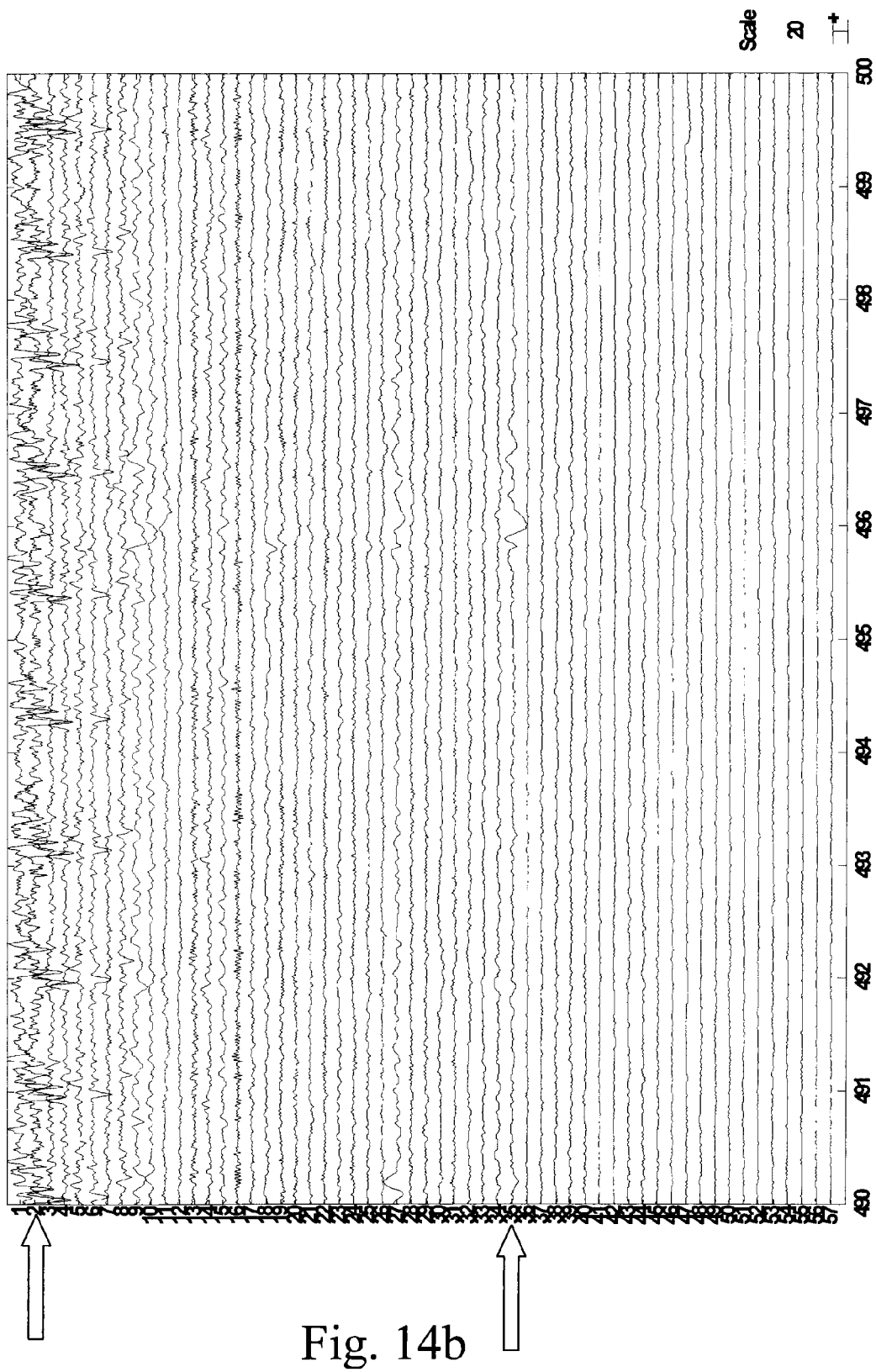
Figure 14C:
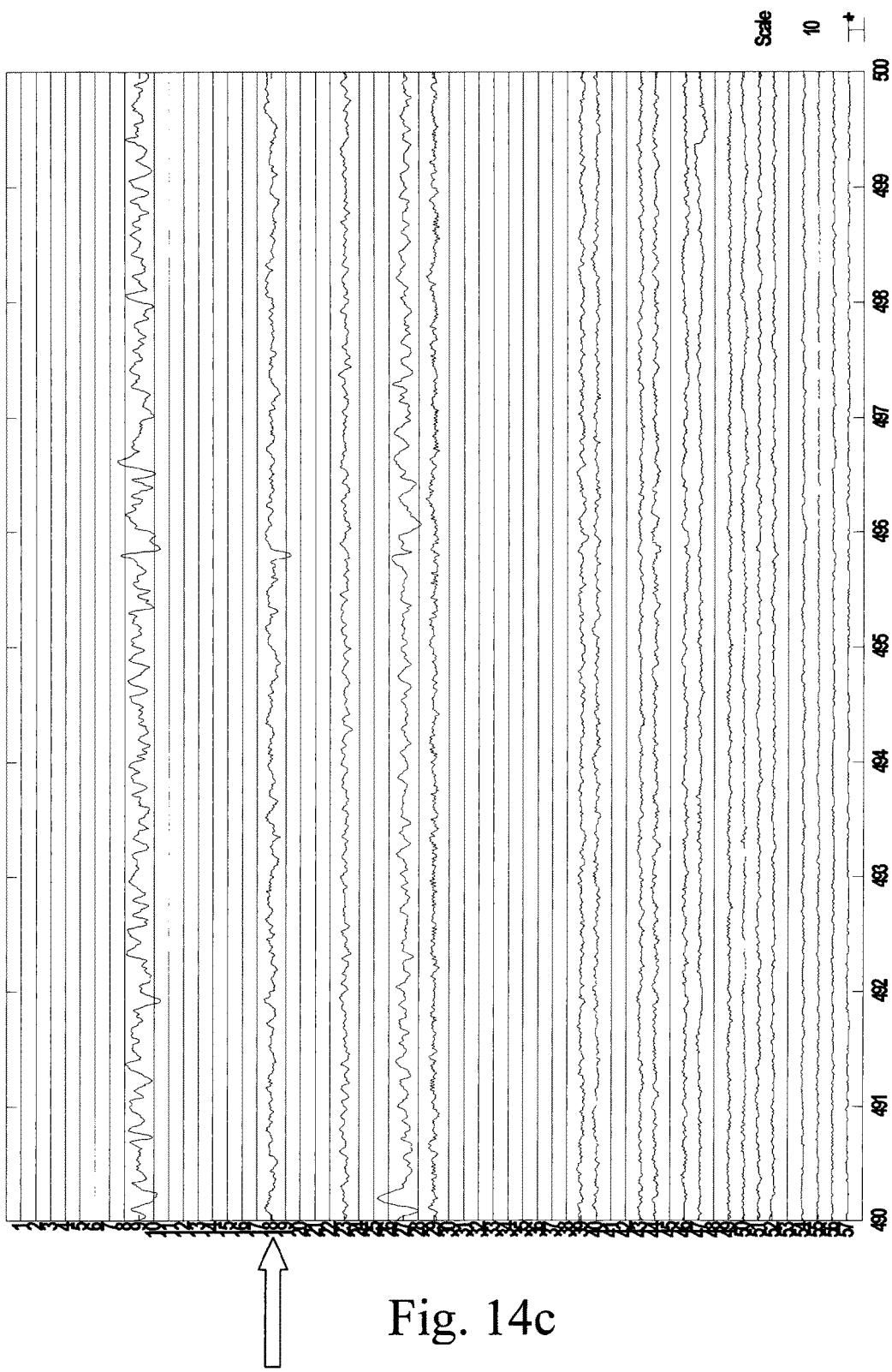

FIG. 14b illustrates the ICA components of the EEG measured data before artifact removal. FIG. 14c shows the ICA components of the EEG measured data after artifact suppression, i.e. after zeroing the noise components that have highest weights on measurements across bundles and retaining the components related to brain signal.

In FIG. 14b, component No. 2 (marked with an arrow) is a cardiobalistic noise component that was removed accordingly by artifact suppression. The following geometrical considerations were then used according to the EVM technique of FIG. 10, in order to determine whether the removal of component No. 2 was justified.

First of all, a suitable electrode triplet was selected (step 744 of FIG. 10). To do this, the electrode pair in which the measurement was most strongly affected by component No. 2 was identified as the pair including the electrodes C3 and P3 (bipolar channel C3-P3). Adjacent bipolar channels forming a triangle were identified as the P3-Cp1 Cp1 and Cp1-C3 channels. Weights associated with component No. 2, termed, were identified along the three electrode pairs (step 746 of FIG. 10), where $w_1$ was the weight corresponding to the C3-P3 channel, $w_2$ was the weight corresponding to the P3-Cp1 channel, and $w_3$ was the weight corresponding to the Cp1-C3 channel. $D_1$ was the distance between the electrodes C3 and P3. $D_2$ was the distance between the electrodes P3 and Cp1. $D_3$ was the distance between the electrodes C3 and Cp1. The sign of the weights depended on the direction of measurement.

$D_1$=40 mm $w_1$=2.7

$D_2$=30 mm $w_2$=2.13

$D_3$=38 mm $w_3$=0.58

According to equation 14:

$\cos(\alpha) = (D_1^2 + D_2^2 - D_3^2)/2 D_1 D_2 = 0.44$

According to equation 15, the gradient along the Cp1-C3 line predicted by a vector sum of the gradient along the C3-P3 line and the gradient along the P3-Cp1 line was calculated (step 748 of FIG. 10)

$s_{i\ 3\ EST} = [s_{i\ 1}^2 + s_{i\ 2}^2 - 2 s_{i\ 1} \cdot s_{i\ 2} \cdot \cos(\alpha)]^{1/2}$ where $s_{i\ 3\ EST}$ is the estimated gradient of the component No 2 along the line connecting the electrodes C3 and Cp1; $s_{i\ 1}$ is the gradient of the component No 2 along the line connecting the electrodes C3 and P3; and $s_{i\ 2}$ is the gradient of the component No 2 along the line connecting the electrodes P3 and Cp1.

However, keeping in mind that:

$s_{i\ 3\ EST} = w_{3\ EST} s$ $s_{i\ 1} = w_1 s$ $s_{i\ 2} = w_2 s$ where s is the value of component No 2, equation 15 can be rewritten as:

$w_{3\ EST} = \sqrt{w_1^2 + w_2^2 - 2\cos\alpha \cdot w_1 w_2} = 4.11$

Therefore a comparison between the estimated gradient (weight) of the component No 2 along the line connecting the electrodes C3 and Cp1 and the gradient of the component No 2 along the line connecting the electrodes C3 and Cp1 calculated from the measured EEG data was performed (step 750 of FIG. 10) by calculating a ratio T, according to equation 18:

$T = (s_{i\ 3\ EST}/s_{i\ 3}) = w_{3\ EST}/w_3 \approx 8$

The estimated weight of component No. 2 was much larger than the weight calculated from the measured EEG data. Hence it was concluded that component No. 2 did not obey geometrical considerations and justifiably identified as an artifact (step 752 of FIG. 10) and rejected (step 754 of FIG. 10).

Component No. 18 (marked with an arrow in FIG. 14c) was preserved by the VMS technique of FIG. 9. Hence it is probably a brain signal component. A geometrical analysis analogous to that performed above with reference to component No. 2 was also performed for component No. 18.

Figure 15A:
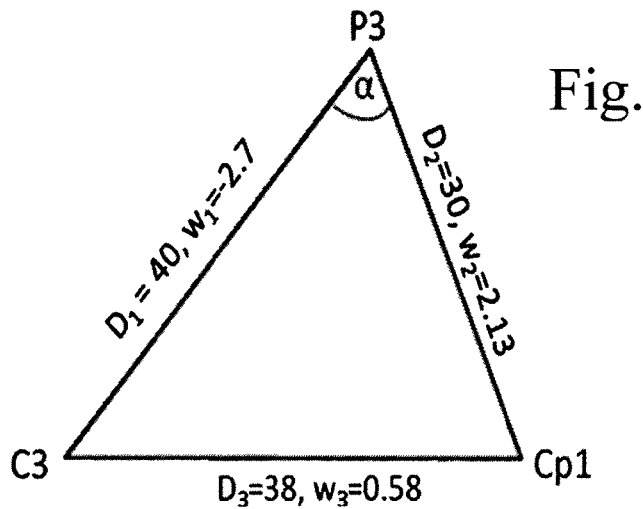
FIGS. 15a-15c illustrate the geometrical analysis of three signal components present in the measured data of FIGS. 14a-14d.
Figure 15B:
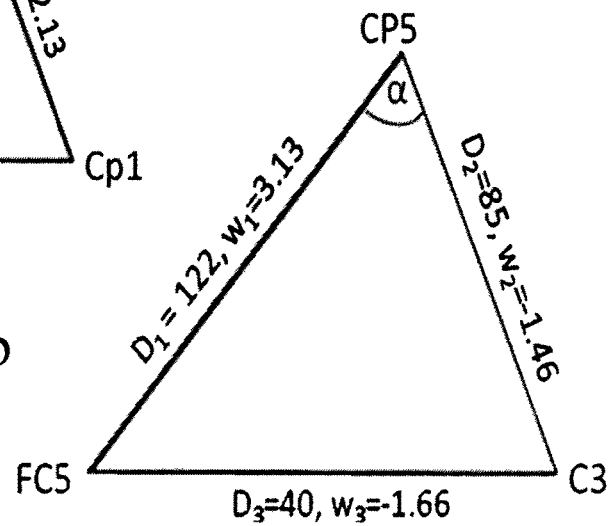
Figure 15C:
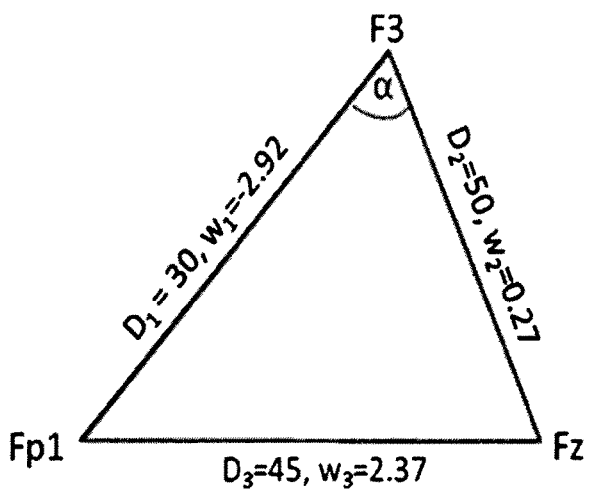

The highest weight of component No. 18 belonged to the bipolar channel FC5-CP5. Adjacent channels forming a triangle are CP5-C3 and C3-FC5. According to the data showed in FIG. 15b, it was found that $\cos(\alpha)$=0.98, $w_{3\ EST}$=1.72, and T≈1. The estimated weight of component No. 18 along the C3-FC5 line was therefore very close to the weight of component No. 18 along the C3-FC5 line calculated from the measured EEG data. Hence we can conclude that component No. 18 represented a neural signal and was justifiably retained.

Component No. 35 (marked with an arrow in FIG. 14b) was removed by the VMS technique of FIG. 9. However, a behavior in time of component No. 35 reveals that component No. 35 may have contained some of the spike signal seen in 496 sec. It was therefore postulated that component No. 35 was mistakenly removed.

A geometrical analysis of component No. 35 was therefore performed according to the EVM technique of FIG. 10. The highest weight of component No. 35 belonged to the bipolar channel Fp1-C3. Adjacent channels forming a triangle are F3-Fz and Fz-Fp1.

Figure 14D:
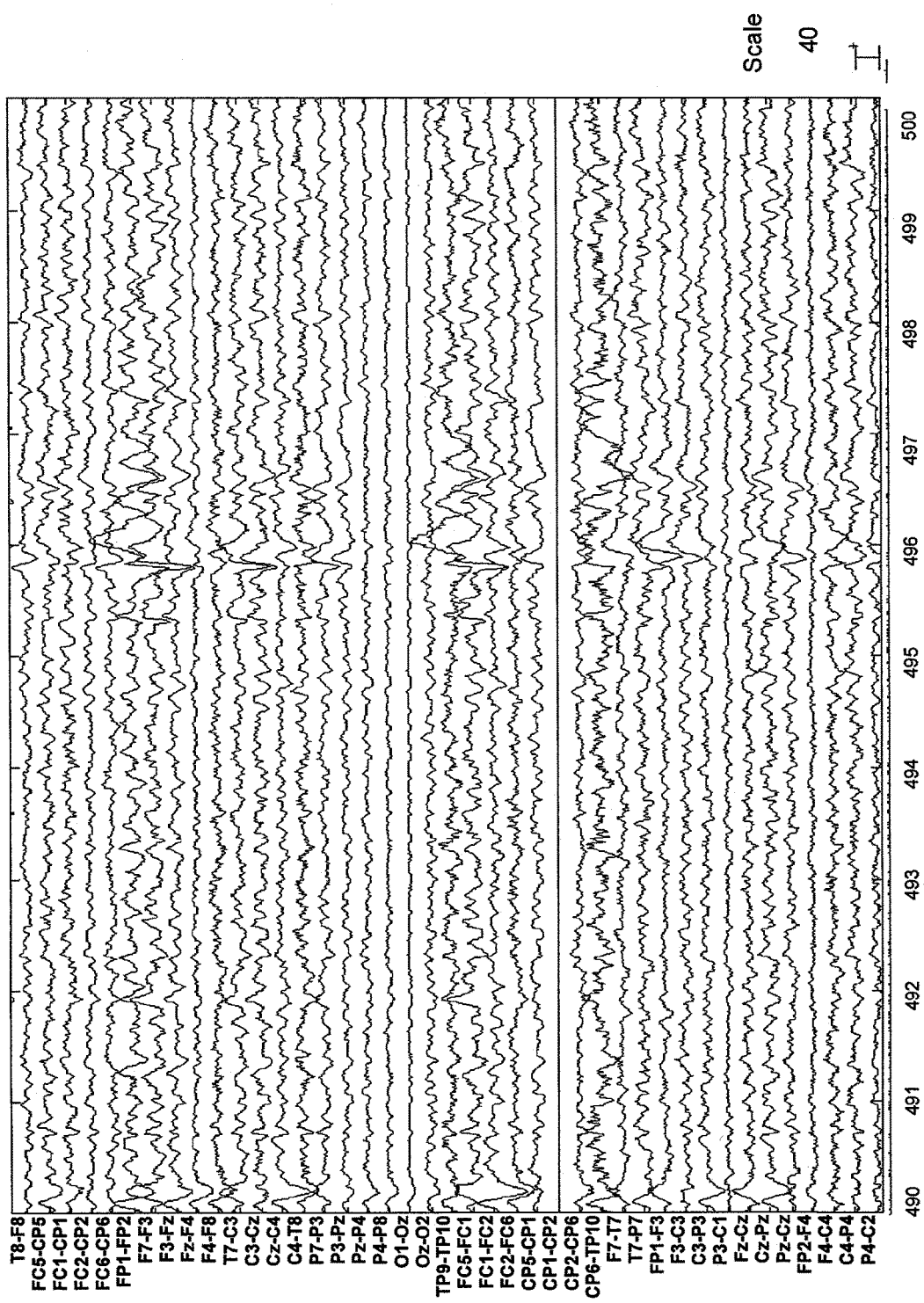

According to the data showed in FIG. 14b, it was found that $\cos(\alpha)$=0.45, $w_{3\ EST}$=3.05, and T≈1.2. The estimated weight of component No. 35 along the Fz-Fp1 line was therefore very close to the weight of component No. 35 along the Fz-Fp1 line calculated from the measured EEG data. Therefore, it was appropriate to suspect that most of component No. 35 is generated by brain activity rather than by an artifact. Hence this component might have been incorrectly removed by the VSM technique of FIG. 9 with too strict a threshold. Adding component No. 35 back into the reconstruction of the EEG data (FIG. 14d), increased the amplitude of the epileptic spike just before 496 seconds, and allows a clearer identification of the epileptic spike, as well as the recognition of additional details of spiking waveforms relating to the epileptic spike that may have been lost is the geometric analysis of the EVM technique had not been performed. Examples of such details may include, for example, a large negative amplitude spike followed by a larger amplitude wave shape seen in frontal electrodes, for example Fp1-Fp2, FC5-FC1. Additional revealed details are slow wave activity seen just before and immediately after the spike.

Figure 16A:
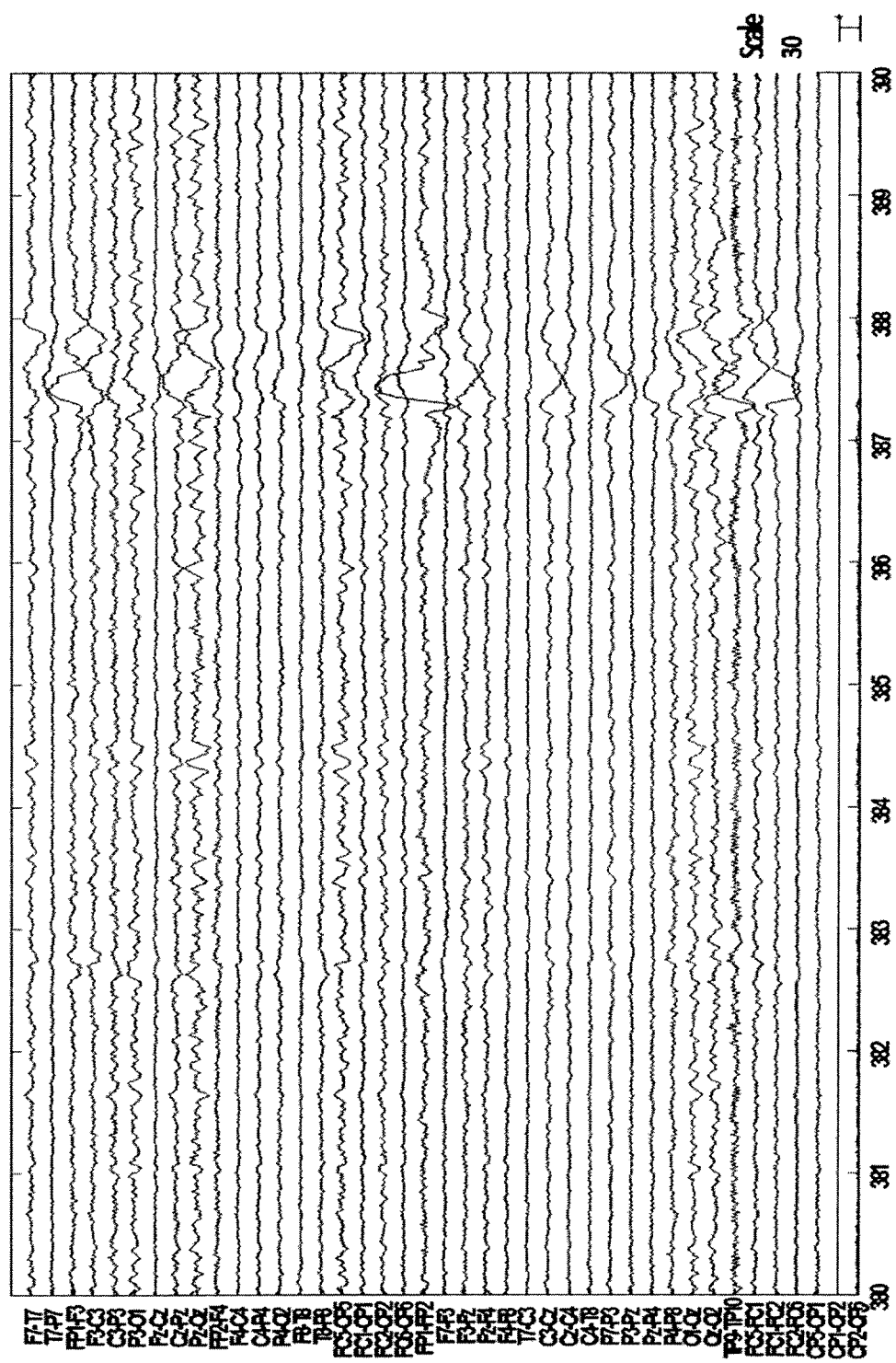
FIGS. 16a-16d illustrate calculated data resulting from the application of the technique of FIG. 9 or of the technique of FIG. 10, in either a strict and permissive mode of such techniques, on EEG measurement data.
Figure 16B:
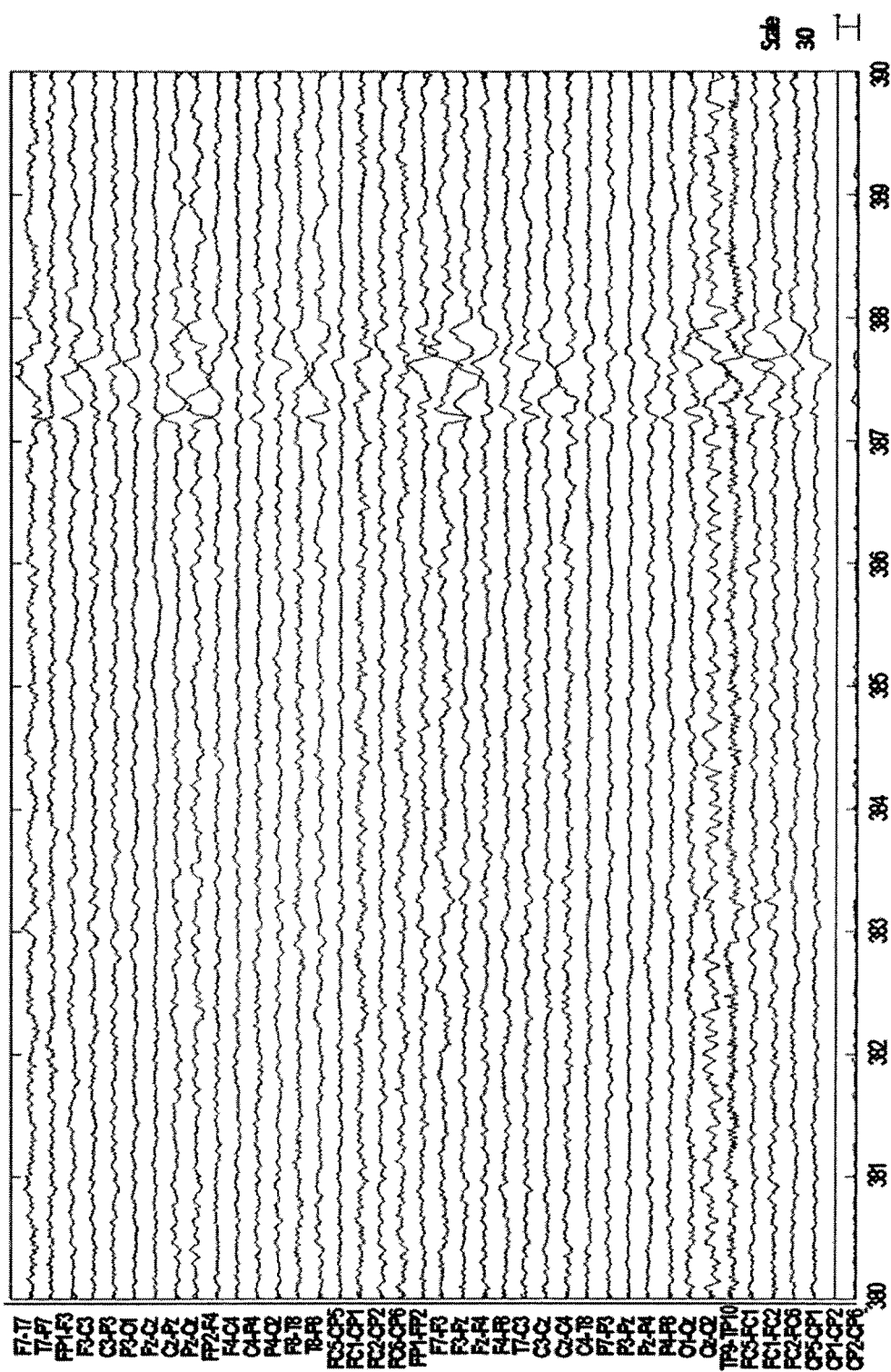
Figure 16C:
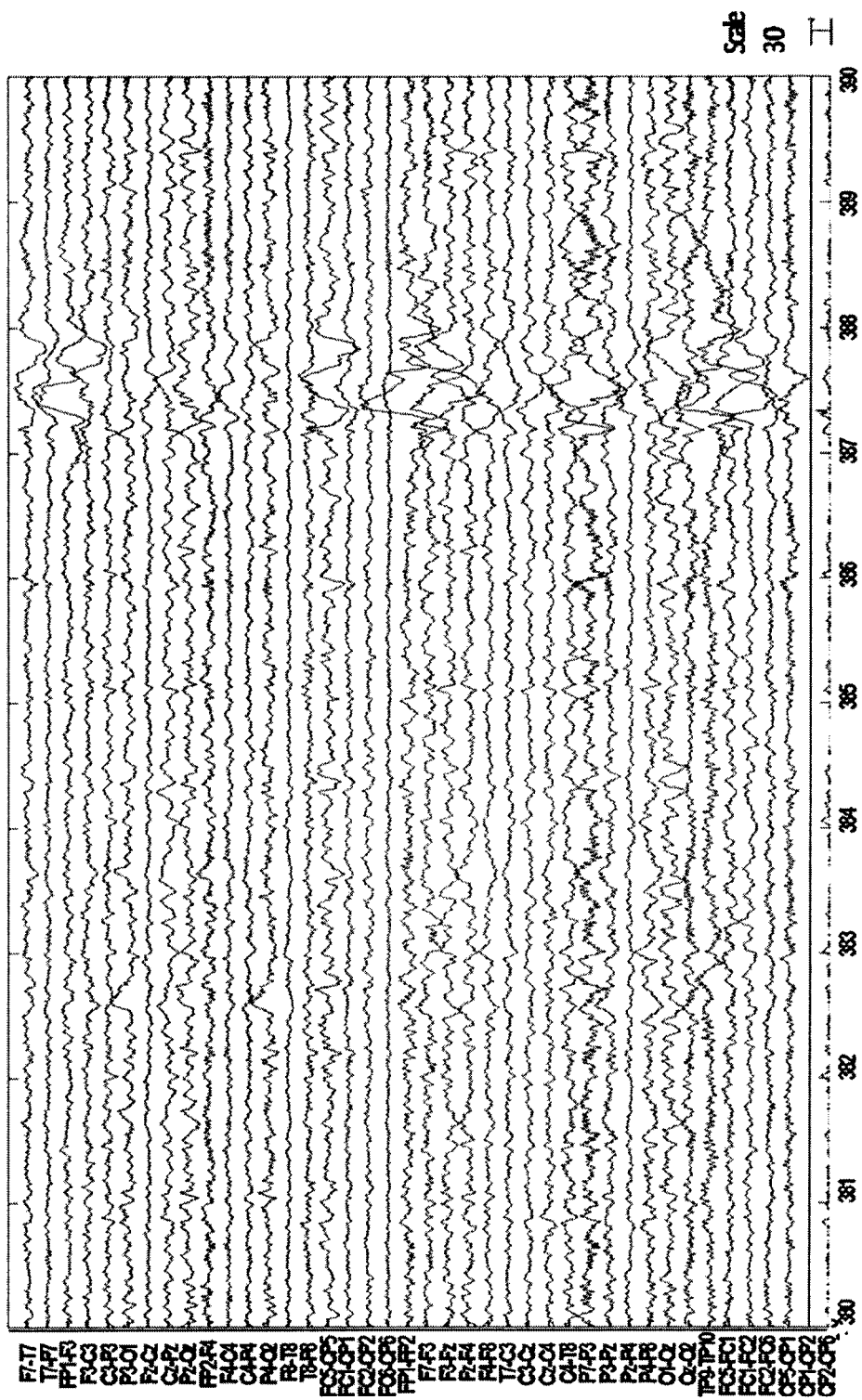
Figure 16D:
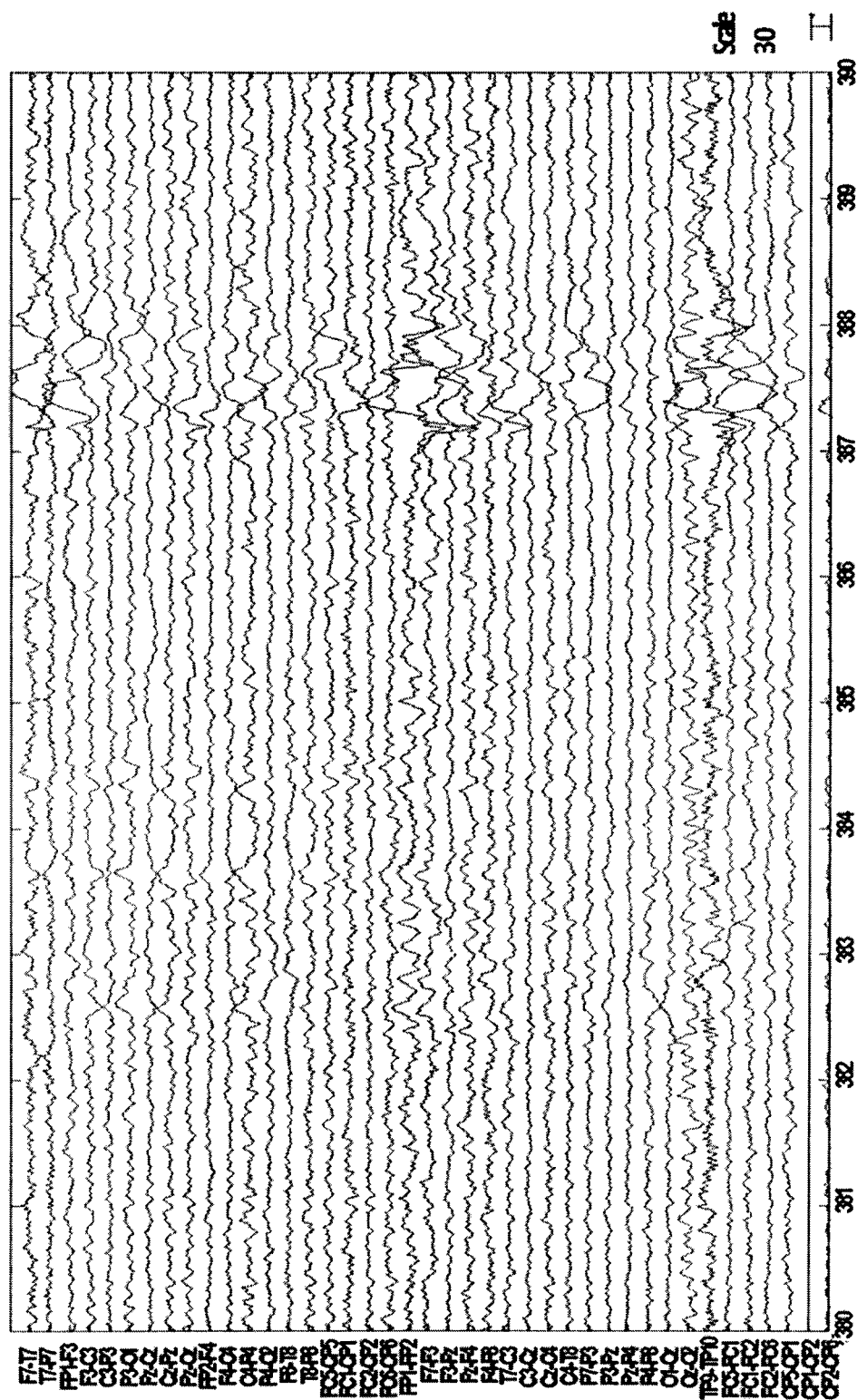
Figure 17A:
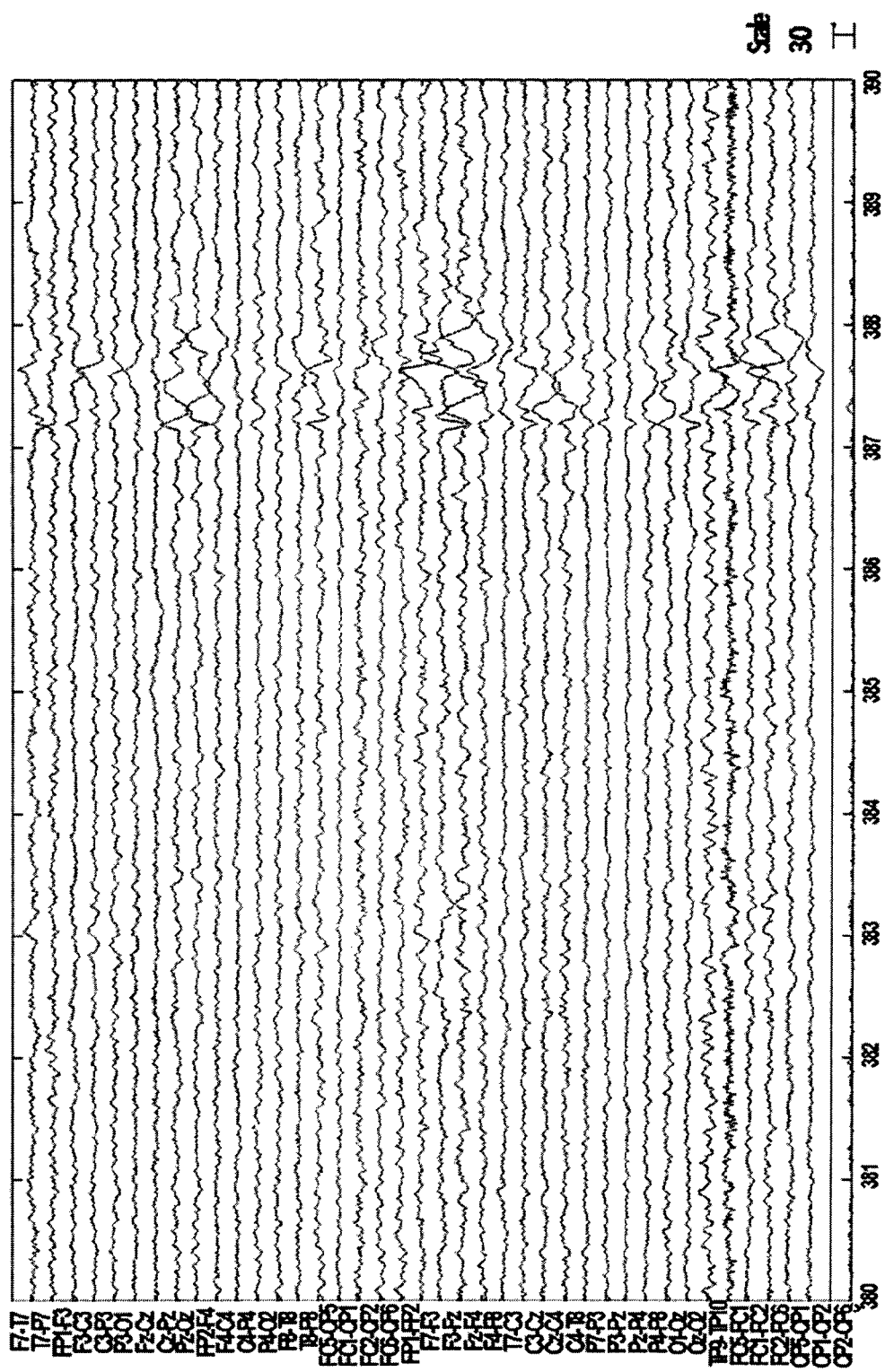
FIGS. 17a-17b illustrate calculated data resulting from the application on EEG measured data of an artifact suppression technique constituted by the technique of FIG. 9 in a strict mode thereof and the technique of FIG. 10 in either a strict and permissive mode.
Figure 17B:
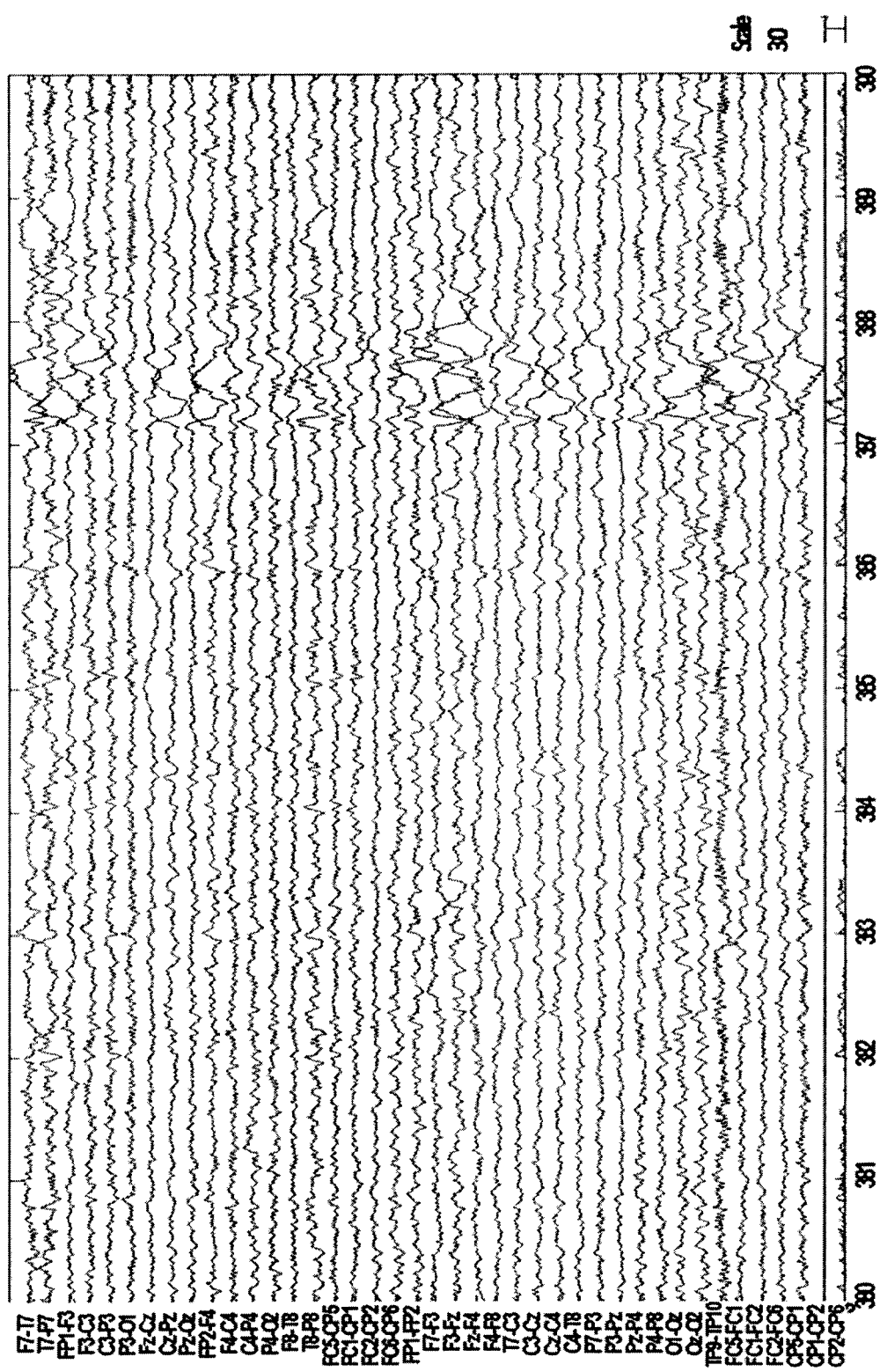

Referring now to FIGS. 16a-16d and FIGS. 17a-17b, FIG. 16a illustrates a corrected EEG signal reconstructed after the application of a strict EVM technique on measured EEG data (components in which 0.75<T<1.5 are recognized as artifacts, as explained above, with reference to FIG. 10); FIG. 16b illustrates a corrected EEG signal reconstructed after the application of a strict VMS technique on measured EEG data (components in which $w_{MAX1}$ and $w_{MAX2}$ correspond to pieces of data generated by measurements across bundles are recognized as artifacts, as explained above, with reference to FIG. 9); FIG. 16c illustrates a corrected EEG signal reconstructed after the application of a permissive EVM technique on measured EEG data (components in which 0.5<T<2 are recognized as artifacts, as explained above, with reference to FIG. 10); and FIG. 16*d* illustrates a corrected EEG signal reconstructed after the application of a permissive VMS (components in which R<0.5 are recognized as artifacts, as explained above, with reference to FIG. 9) technique on measured EEG data. FIG. 17*a* illustrates a corrected EEG signal reconstructed after the application on EEG measured data of an artifact suppression technique constituted by a strict VMS technique and a strict EVM technique. FIG. 17*b* illustrates a corrected EEG signal reconstructed after the application on EEG measured data of an artifact suppression technique constituted by a strict VMS technique and a permissive EVM technique.

In the figures, epileptic spike activity is seen near 387 second. It can be seen that the application of strict of strict EVM (FIG. 16*a*) and strict VMS (FIG. 16*b*) led to good noise suppression, but also some epileptic signal was lost. Permissive EVM (FIG. 16*c*) and permissive VMS (FIG. 16*d*) led to more complete epileptic signal reconstruction, but also some nose was retained in the data. The combination of VMS and EVM (FIGS. 17*a*-17*b*) led to compromise results with satisfactory noise suppression and satisfactory epileptic signal reconstruction. More specifically, FIG. 17*b* demonstrates more details of epileptic signal than FIG. 17*a*. For example, in FIG. 17*a*, the signal measured between the electrodes T8 and P8 practically lacks any indication of an epileptic signal, while in FIG. 17*b* a clear sharp wave is detected between the same electrodes T8 and P8. The same is true for electrode pair FP1-FP2. It can also be noticed that there is little difference in noise between FIGS. 17*a* and 17*b*. Therefore, by select in the strictness/permissiveness of VSM and EVM, the combination of VSM and EVM can be tailored such that components having a neural origin are retained while most artifacts are rejected.

The invention claimed is:

1. A measurement device for use in an electroencephalogram (EEG) measurement performed in the presence of a magnetic field, the measurement device comprising a wiring array for connecting an electrodes arrangement comprising a plurality of EEG electrodes to an EEG monitor comprising a control unit being configured and operable to analyze neural signals received from said electrodes arrangement and generate EEG data, wherein:

the wiring array comprises a plurality of sampling lines arranged to form a first group of sampling lines arranged in a spaced-apart substantially parallel relationship extending along a first axis, at least some of said first group of sampling lines being a first group of wire bundles each comprising a plurality of first wires for connecting to a corresponding first plurality of electrodes, of said electrodes arrangement, extending along said first axis; and a second group of sampling lines arranged in a spaced-apart substantially parallel relationship extending along a second axis, at least some of said second group of sampling lines being a second group of wire bundles each comprising a plurality of second wires for connecting to a corresponding second plurality of electrodes, of said electrodes arrangement, extending along said second axis; wherein said first group of wire bundles intersects with said second group of wire bundles over an area of measurement locations when said wiring array is placed on a patient's scalp, the wiring array being configured and operable for simultaneously transmitting to the EEG monitor, first and second sets of EEG measurements obtained by electrodes of said electrodes arrangement being located in said area of measurement locations when said wiring array is placed on the patient's scalp, the first set being obtained along at least one sampling line of said first group of sampling lines and the second set being obtained across at least two different sampling lines of said second group of sampling lines, thereby enabling generation of EEG data characterized by at least one of a reduced motion artifact and a reduced gradient artifact associated with the presence of the magnetic field during the EEG measurement.

2. The measurement device of claim 1, wherein said second axis is substantially perpendicular to said first axis.

3. The measurement device of claim 1, wherein the wiring array is in the form of a net structure that is (a) configured for connecting said EEG monitor to the electrodes arrangement, wherein the electrodes of the electrodes arrangement are capable of being positioned along a patient's scalp according to the International 10-20 system; or (b) configured for connecting said EEG monitor to the electrodes arrangement, wherein at least some electrodes of the electrodes arrangement are capable of being joined to the patient's head in one of the following manners: non-invasively placed on the patient's scalp, semi-invasively joined to the patient's head epidural region, and invasively joined to the patient's head subdural region.

4. The measurement device of claim 1, wherein at least some of the sampling lines are configured for being removably connectable to the electrodes, thereby allowing for a replacement of at least some of the electrodes between scans.

5. The measurement device of claim 1, wherein at least one of said first and second groups of sampling lines comprises at least two sub-groups, wherein sampling lines of the at least two sub-groups are arranged in an alternating fashion such that any two adjacent sampling lines belonging to said first or second group belong respectively to different sub-groups of said first or second group.

6. The measurement device of claim 1, further comprising:

at least one of an MRI scanner for imaging the patient's brain or a Transcranial Magnetic Stimulation (TMS) coil device configured and operable to produce a changing magnetic field to cause activity in the patient's brain;

an EEG monitor comprising a control unit; and an electrodes arrangement;

said wiring array being connected between the EEG monitor and the electrodes, said electrodes being configured for being placed at predetermined locations on the patient's scalp and for detecting a neural signal when placed on the patient's scalp; and said wiring array being thereby configured for relaying said neural signals to the EEG monitor for analysis of said neural signal and generation of EEG data.

7. The measurement device of claim 6, having one of the following configurations: (i) at least one of said sampling lines is configured to connect to a pair of electrodes of said electrodes arrangement; and (ii) the electrode arrangement comprises a reference electrode, a first electrode configured to obtain a first bipolar measurement with the reference electrode, and a second electrode configured to obtain a second bipolar measurement with the reference electrode, the first and second electrodes being both connected to one of the sampling lines, said EEG data generated at the EEG monitor being a combination of said first and second bipolar measurements and being indicative of a signal between the first and second electrodes.

8. The measurement device of claim 6, wherein the measurement device comprises the TMS coil device and the magnetic field is a changing magnetic field generated by the TMS coil device.

9. The device of claim 6, wherein said control unit is configured and operable for receiving the EEG data and selecting therefrom data pieces, and analyzing said data pieces for recognizing and suppressing at least one of a motion artifact and gradient artifact.

10. The measurement device of claim 9, wherein said selecting of said data pieces comprises selecting a first sub-set of measurements from said first set of measurements between a first group of electrode pairs of said first plurality of electrodes, and selecting a second sub-set of measurements from said second set of measurements between a second group of electrode pairs of said second plurality of electrodes.

11. The measurement device of claim 10, wherein said control unit is configured and operable for analyzing the selected data pieces by:
applying to said first and second sub-sets a separation algorithm to jointly decompose the selected data pieces of the first and second sub-sets of signal measurements into a plurality of components;
comparing an effect of at least some of said plurality of components on each of the first and second sub-sets of measurements; and
recognizing at least one specific component which has an effect on said second sub-set of measurements that is larger than the effect on said first sub-set of measurements, and labeling said at least one specific component as an artifact-affected component.

12. The measurement device of claim 9, wherein the selecting of said data pieces comprises selecting at least a set of signal measurements between a group of electrode pairs of at least one of said first and second plurality of electrodes.

13. The device of claim 12, wherein:
the control unit is configured and operable to select the set of signal measurements by selecting a first sub-set of signal measurements from said first set of measurements obtained between a first group of electrode pairs of said first plurality of electrodes, and by selecting a second sub-set of the signal measurements from said second set of measurements obtained between a second group of electrode pairs of said second plurality of electrodes.

14. The measurement device of claim 1, further comprising the EEG monitor comprising the control unit, wherein said control unit is configured and operable to compare said first and second sets of EEG measurements to separate EEG data indicative of neural signals from EEG data indicative of at least one of a motion artifact and a gradient artifact.

15. A net structure configured for being placed on a patient's scalp in an electroencephalogram (EEG) measurement performed in the presence of a magnetic field, the net structure comprising a wiring arrangement, which comprises first and second groups of sampling lines including first and second wire bundles and extending along first and second axes respectively, the first and second wire bundles intersecting over an area of measurement locations when placed on the patient's scalp, each group comprising a plurality of spaced-apart substantially parallel sampling lines configured for transmitting EEG signals from a respective plurality of spaced-apart EEG measurement locations, to read EEG data from the measurement locations via the first and second groups of sampling lines, while decreasing at least one of a motion artifact and a gradient artifact generated in the EEG measurement.

16. A cap configured for being worn by a patient in an electroencephalogram (EEG) measurement performed in the presence of a magnetic field, the cap carrying a wiring arrangement, which comprises first and second groups of sampling lines including first and second wire bundles respectively, and extending along first and second axes, the first and second wire bundles intersecting over an area of measurement when placed on a patient's scalp, each group comprising a plurality of spaced-apart substantially parallel sampling lines, each sampling line being configured for transmitting EEG signals from a respective plurality of spaced-apart EEG measurement locations, to simultaneously read EEG data from the measurement locations along one or more of the first wire bundles and across at least two of the second wire bundles, thereby decreasing at least one of a motion artifact and a gradient artifact generated in the EEG measurement.

17. A cap configured for being worn by a patient during an electroencephalogram (EEG) measurement performed in the presence of a magnetic field, the cap comprising the measurement device of claim 1.

18. The cap of claim 17, further comprising:
an electrically non-conductive headpiece, comprising:
an inner surface, configured for being fitted to the patient's head;
an outer surface carrying said wiring array; and
a plurality of apertures, each said aperture being configured for being traversed by a portion of one of said electrodes for connecting to one of said wires.

19. The cap of claim 18, wherein said headpiece comprises fasteners located on said outer surface and configured for fastening said wiring array to said headpiece.

20. The cap of claim 18, wherein said headpiece is made of a stretchable material, for closely fitting the scalp of the patient.

21. A method for performing an electroencephalogram (EEG) measurement in the presence of a magnetic field, the method comprising:
providing an electrode arrangement comprising a plurality of EEG electrodes, capable of being joined to a patient's head;
providing an EEG monitor comprising a control unit being configured and operable to analyze neural signals received from said electrodes arrangement and generate EEG data;
connecting said plurality of EEG electrodes to the EEG monitor, using a wiring array comprising: a first group of sampling lines arranged in a spaced-apart substantially parallel relationship extending along a first axis, at least some of said first group of sampling lines being a first group of wire bundles, each of said first group of wire bundles comprising a plurality of first wires for connecting to a corresponding first plurality of electrodes of said plurality of EEG electrodes; and a second group of sampling lines arranged in a spaced-apart substantially parallel relationship extending along a second axis, at least some of said second group of sampling lines being a second group of wire bundles, each of said second group of wire bundles comprising a plurality of second wires for connecting to a corresponding second plurality of electrodes, of said plurality of EEG electrodes, extending along said second axis; wherein said second group of wire bundles intersects with said first group of wire bundles to form a net structure over an area of measurement locations on the patient's head;

measuring simultaneously first and second neural signals using electrodes located in said area of measurement locations, the first neural signal being obtained along one or more sampling lines of said first group and the second neural signal being obtained across different sampling lines of said second group;

transmitting said first and second neural signals to said EEG monitor via said wiring array; and analyzing said first and second neural signals and yielding EEG data being characterized by at least one of a reduced motion artifact and a reduced gradient artifact.

22. The method of claim 21, comprising:
processing said EEG data to calculate an amplitude and an orientation of said neural signals.

23. The method of claim 21, wherein said measuring of said first neural signal comprises measuring between a reference electrode and one or more electrodes of said first plurality of electrodes.

24. The method of claim 23, wherein said measuring of each of said first and second neural signals comprises measuring the neural signal between the reference electrode and at least some of said electrodes of said electrodes arrangement; and wherein said yielding of EEG data comprises combining data indicative of two measurements taken between said reference electrode and respectively a first and a second electrode of said first plurality of electrodes being connected to the same sampling line to thereby provide combined EEG data, such that said combined EEG data is indicative of a neural signal between said first and second electrodes.

25. The method of claim 21, wherein said magnetic field is a constant magnetic field generated by a magnetic resonance imaging scanner, or a changing magnetic field generated by a transcranial magnetic stimulation coil device.

26. The method of claim 21, further comprising selecting from the EEG data, data pieces, analyzing the selected data pieces and recognizing and suppressing at least one of a motion artifact and a gradient artifact generated in the EEG measurement.

27. The method of claim 26, wherein:
said analyzing of the selected data pieces comprises:
applying to said first and second neural signals a separation algorithm to jointly decompose said selected data pieces into a plurality of components;
comparing an effect of at least some of said plurality of components on each of the first and second neural signals; and
recognizing at least one specific component from said plurality of components which has an effect on said second neural signal that is larger than an effect on said first neural signal, and labeling said at least one specific component as a motion artifact-affected component or a gradient artifact-affected component.

28. The method of claim 27, wherein:
said comparing comprises:
determining a first value indicative of the effect of said at least one specific component on said first neural signal, and a second value indicative of the effect of said at least one specific component on said second neural signal;
calculating a relation between said first and second values; and
comparing said relation to a predetermined threshold; and wherein
said recognizing at least one specific component comprises identifying said at least one specific component as one of the motion artifact-affected component or the gradient artifact-affected component, according to said comparison between said relation and said predetermined threshold.

29. The method of claim 26, wherein:
said analyzing of the selected data pieces comprises:
applying to said selected data pieces a separation algorithm to decompose said data into a plurality of components;
for each of at least some of said plurality of components, selecting at least three electrodes from said first or second plurality of electrodes, such that two of said at least three electrodes are connected to different sampling lines; and
for each of at least some of said plurality of components, calculating gradients of each component along respective sides of a polygon defined by said electrodes and analyzing said gradients.

30. The method of claim 21, comprising:
positioning at least one of said first and second groups of sampling lines such that the at least one of said first and second groups of sampling lines comprises at least two sub-groups of the sampling lines,
wherein sampling lines of the sub-groups are positioned in an alternating fashion such that any two adjacent sampling lines belonging to said first or second group belong respectively to different sub-groups of said first or second group.

* * * * *